United States Patent [19] [11] 4,139,540
Heeres [45] Feb. 13, 1979

[54] 2-ARYL-2-HALOMETHYL-4-ALKENYL-1,3-DIOXOLANES

[75] Inventor: Jan Heeres, Vosselaar, Belgium

[73] Assignee: Janssen Pharmaceutica N.V., Beerse, Belgium

[21] Appl. No.: 774,290

[22] Filed: Mar. 4, 1977

Related U.S. Application Data

[60] Continuation-in-part of Ser. No. 710,994, Aug. 2, 1976, abandoned, which is a division of Ser. No. 619,863, Oct. 6, 1975, abandoned, which is a continuation-in-part of Ser. No. 544,157, Jan. 27, 1975, Pat. No. 3,936,470.

[51] Int. Cl.² ............................................. C07D 317/10
[52] U.S. Cl. .......................... 260/340.9 R; 260/329 R; 260/332.5; 260/348.11; 260/348.25; 260/671 A; 548/336
[58] Field of Search ................................. 260/340.9 R

[56] References Cited
U.S. PATENT DOCUMENTS 3,055,766  9/1962  Reinhardt ...................... 260/340.9 R Primary Examiner—Ethel G. Love
Attorney, Agent, or Firm—Salvatore R. Conte

[57] ABSTRACT

Novel compounds denoted as 2-aryl-2-halomethyl-4-alkenyl-1,3-dioxolanes used as intermediates in making 1-(2-Ar-4-R-1,3-dioxolan-2-ylmethyl)imidazoles, useful as antifungal and antibacterial agents.

2 Claims, No Drawings

2-ARYL-2-HALOMETHYL-4-ALKENYL-1,3-DIOXOLANES

CROSS-REFERENCE TO RELATED APPLICATIONS

This is a continuation-in-part of our copending application Ser. No. 710,994, filed Aug. 2, 1976, now abandoned; which in turn is a Division of Ser. No. 619,863, filed Oct. 6, 1975, now abandoned; which in turn is a continuation-in-part, Ser. No. 544,157, filed Jan. 27, 1975, issued as U.S. Pat. No. 3,936,470.

PRIOR ART

In U.S. Pat. Nos. 3,575,999 and 3,717,655 are described some 1-(2-aryl-1,3-dioxolan-2-ylmethyl-)imidazoles. The compounds of the present invention differ from the foregoing essentially by the nature of the R-substituent, present in the 4-position of the dioxolane group.

DESCRIPTION OF THE INVENTION

The invention relates to novel imidazole derivatives having the formula:

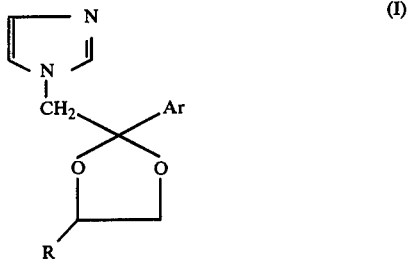

and the therapeutically acceptable acid addition salts thereof, wherein:

Ar is a member selected from the group consisting of phenyl, substituted phenyl, thienyl, halothienyl and naphthyl, and wherein said substituted phenyl is phenyl having from 1 to 3 substituents independently selected from the group consisting of halo, loweralkyl, loweralkyloxy, nitro and cyano; and R is a member selected from the group consisting of alkyl having from 2 to about 10 carbon atoms, alkyloxymethyl wherein the alkylgroup has from 1 to about 10 carbon atoms, alkenyl, alkenyloxymethyl, wherein said alkenyl has from 2 to about 10 carbon atoms, hydroxymethyl, 2-propynyloxymethyl, halomethyl, aryl, arylloweralkyl, aryloxymethyl, arylthiomethyl and arylmethoxymethyl, wherein said aryl is a member selected from the group consisting of phenyl, substituted phenyl, naphthyl, and mono- and di-halonaphthyl and wherein said substituted phenyl is phenyl having from 1 to 3 substituents independently selected from the group consisting of halo, loweralkyl, loweralkyloxy, cyano, nitro, phenyl, phenylmethyl, benzoyl, halobenzoyl, loweralkylcarbonyl, loweralkyloxycarbonyl and trifluoromethyl, provided that when more than one substituents are present only one thereof may be selected from the group consisting of phenyl, phenylmethyl, benzoyl and halobenzoyl.

More particularly "alkyl" as used in the definition of R is meant to include straight and branch chained hydrocarbon radicals having from 2 to about 10 carbon atoms, such as, for example, ethyl, propyl, 1-methylethyl, 1,1-dimethylethyl, butyl, pentyl, hexyl, heptyl, octyl, decyl and the like alkyls; "alkyl" as used in the definition of alkyloxymethyl is meant to include straight and branch chained hydrocarbon radicals having from 1 to about 10 carbon atoms, such as, for example, methyl and the alkyls mentioned herebefore; "loweralkyl" as used herein has the meaning of a straight or branch chained alkyl radical having from 1 to about 6 carbon atoms, such as, for example, methyl, ethyl, propyl, 1-methylethyl, 1,1-dimethylethyl, butyl, pentyl, hexyl and the like alkyls; "alkenyl" as used herein refers to straight and branch chained alkenyl radicals having from 2 to about 10 carbon atoms, such as, for example, ethenyl, 2-propenyl, 2-butenyl, 3-butenyl, 2-pentenyl, 2-hexenyl, 2-decenyl and the like alkenyls; and the term "halo" is generic to halogens of atomic weight less than 127, i.e., fluoro, chloro, bromo and iodo.

The compounds of formula (I) are conveniently prepared by reacting imidazole (II) with an appropriate reactive ester of formula (III) wherein Ar and R are as previously defined and wherein W is a reactive ester function, such as, for example, halo, 4-methylbenzenesulfonate, methylsulfonate and the like. Preferred reactive esters are halides and more particularly bromides and chlorides.

In one method of conducting the reaction between imidazole and (III), imidazole is first transformed into a metal salt thereof by treatment with an appropriate metallating agent such as, for example, a metal alkoxide, e.g., sodium- or potassium methanolate, or a metal hydride such as sodium hydride. The thus obtained metal salt is then reacted with (III) in an appropriate organic solvent, such as, for example, dimethylformamide or dimethylacetamide. A small amount of a metal iodide, such as sodium or potassium iodide may advantageously be added to promote the reaction, especially when the reactive ester is a chloride or bromide.

Alternatively, the reaction of imidazole with the reactive ester (III) may also be carried out without previous salt formation, by bringing the reactants into contact with each other in an appropriate organic solvent such as, for example, dimethylformamide or dimethylacetamide. In these circumstances it is appropriate to use an excess of imidazole or to add to the reaction mixture an appropriate base such as, for example, sodium or potassium carbonate or bicarbonate in order to bind the acid which is liberated during the course of the reaction. The use of an excess of imidazole is however preferred. Further it is advantageous to conduct the reaction in the presence of a metal iodide such as, for example, sodium or potassium iodide.

In each of the above procedures, somewhat elevated temperatures may be employed to enhance the rate of the reaction and most conveniently the reactions are carried out at the reflux temperature of the reaction mixture.

In these and the following preparations the reaction products may be isolated from the medium and, if necessary, further purified according to methodologies generally known in the art, such as, for example, extraction, trituration, crystallization, chromatography, etc..

The foregoing procedures are more fully illustrated by the following schematic representation:

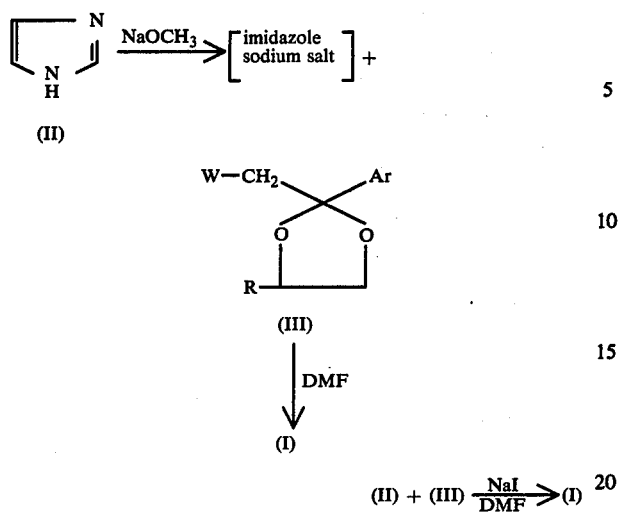

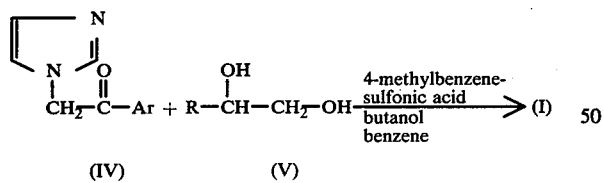

An additional method of preparing the compounds of formula (I) is by the ketalization of an appropriate aroylmethylimidazole of formula (IV) wherein Ar has the same meaning as assigned to it previously with an appropriate diol of formula (V) wherein R is as previously defined.

Said ketalization reaction may be carried out following methodologies analogous to those described in the literature, e.g., for the preparation of 2-bromomethyl-2,4-diphenyl-1,3-dioxolane [Synthesis, 1974(I), 23].

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as cyclohexane. The foregoing reaction may be illustrated as follows:

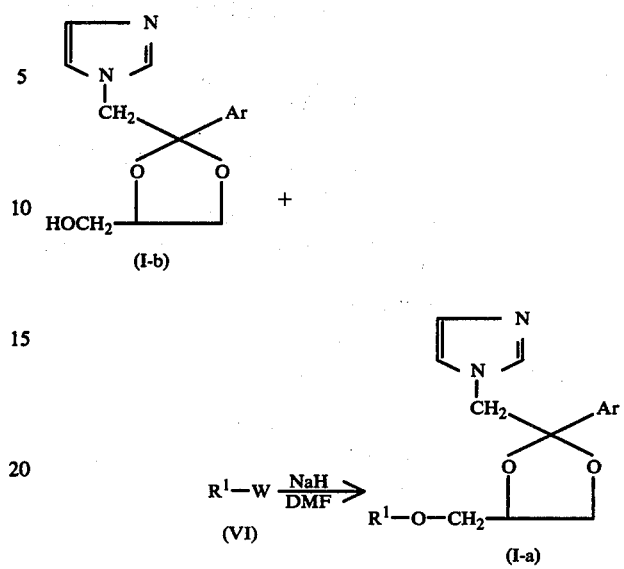

The compounds of formula (I) wherein R represents an alkyloxymethyl, alkenyloxymethyl, 2-propynyloxymethyl or arylmethoxymethyl radical, (I-a), may still by prepared by the reaction of an appropriate compound of formula (I) wherein R is hydroxymethyl (I-b) with an appropriate reactive ester of formula (VI) wherein $R^1$ is selected from the group consisting of alkyl, alkenyl, 2-propynyl and arylmethyl and W is a reactive ester function as previously defined, according to common O-alkylating procedures. Preferably the reaction is carried out in a suitable organic solvent such as, for example, dimethylformamide or dimethylacetamide in the presence of an appropriate strong metal base such as, for example, sodium hydride, sodium carbonate, potassium carbonate and the like.

The compounds of formula (I) wherein R stands for alkyloxymethyl, (I-c), may still be prepared by the condensation of (I-b) with an appropriate alkanol. Said condensation reaction may be carried out by refluxing the reactants together under azeotropic water removal in an appropriate organic solvent such as, for example, an aromatic hydrocarbon, e.g., benzene, methylbenzene, dimethylbenzene and the like, a saturated hydrocarbon, e.g., cyclohexane, or in the alkanol itself, in the presence of an appropriate strong acid, such as, for example, 4-methylbenzenesulfonic acid.

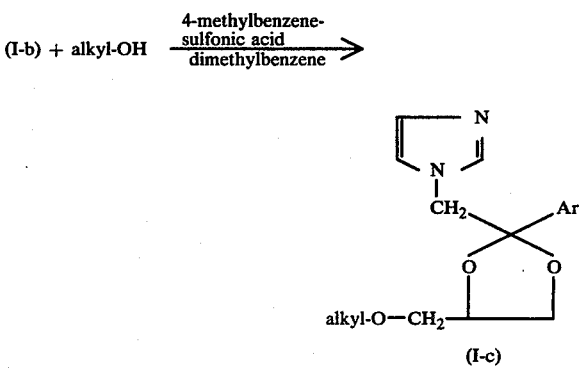

Those compounds of formula (I) wherein R represents alkyloxymethyl, alkenyloxymethyl, 2-propynyloxymethyl, arylmethoxymethyl or aryloxymethyl, (I-d), may still be prepared by the reaction of an appropriate reactive ester of formula (VII) wherein Ar and W are as defined hereinbefore with an appropriate hydroxy compound of the formula (VIII) wherein $R^2$ is selected from the group consisting of alkyl, alkenyl, 2-propynyl, arylmethyl and aryl according to common O-alkylating procedures as described herebefore.

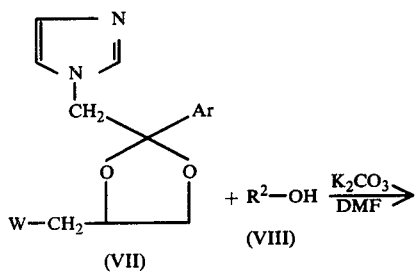

+ R²—OH $\xrightarrow[\text{DMF}]{\text{K}_2\text{CO}_3}$ (VII)    (VIII)

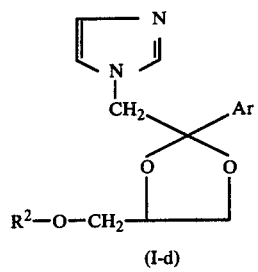

(I-d)

The imidazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic base such as acetic, propanoic, hydroxyacetic, α-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenylpropenoic, α-hydroxybenzeneacetic, methanesulfonic, ethanesulfonic, 2-hydroxyethanesulfonic, 4-methylbenzenesulfonic 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

The intermediates of formula (III) may be prepared by subjecting an appropriate ketone of formula (IX), wherein Ar and W are as previously defined by a ketalization reaction with an appropriate diol of formula (V) in the same manner as described hereinbefore for the preparation of the compounds (I) starting from (IV) and (V).

$$\text{W—CH}_2\text{—}\overset{\overset{\text{O}}{\|}}{\text{C}}\text{—Ar} +$$

(IX)

$$\text{R—}\overset{\overset{\text{OH}}{|}}{\text{CH}}\text{—CH}_2\text{OH} \xrightarrow[\substack{\text{butanol}\\\text{benzene}}]{\text{4-methylbenzenesulfonic acid}} \text{(III)}$$

(V)

Alternatively the intermediates of formula (III) are conveniently prepared by transketalization of a ketal derivative of a ketone of formula (IX) such as, for example, a loweralkyl ketal or a cyclic loweralkylene ketal, with a glycol of formula (V) under conditions similar to those described hereinbefore for the direct ketalization. The loweralkyl ketals and cyclic loweralkylene ketals used herein as starting materials are easily obtained by ketalization of a ketone of formula (IX) with a lower alkanol or alkanediol according to methodologies known in the art. A number of such compounds and methods of preparing the same are described in U.S. Pat. Nos. 3,575,999 and 3,717,655.

The intermediates of formula (III) wherein Ar and W are as previously defined an R is other than alkyl having 2-10 carbon atoms, provided that when said Ar is phenyl, then said R is other than phenyl, are deemed to be novel and as useful intermediates herein they constitute an additional feature of this invention.

A number of the precursor glycols of formula (V) are known and they may all be prepared according to known procedures as described in the literature. In general, they may be derived from the corresponding 2-R-oxiranes of formula (X) by hydrolytic cleavage of the oxirane nucleus with an appropriate strong acid such as, for example, ethanedioic acid, sulfuric acid, hydrochloric acid and the like.

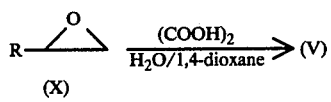

(X)

The oxiranes of formula (X) may in turn be obtained in a variety of ways.

Those of formula (X-a), wherein R³ stands for alkyl or arylloweralkyl may, for example, be prepared by oxidizing an appropriate alkene or arylalkene of formula (XI) with an appropriate oxydizing agent such as, for example, a benzeneperoxoic acid, e.g., 3-chlorobenzeneperoxoic acid,

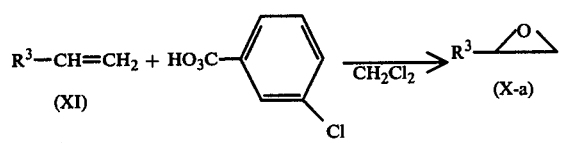

Alternatively intermediates of formula (X-a) may still be obtained by:

i. converting an appropriate halide of formula (XII) wherein R⁴ is alkyl or arylloweralkyl, having one carbon less than in the corresponding R³, into a Grignard complex with magnesium, ii. reacting said Grignard complex with an appropriate 2-halomethyloxirane of formula (XIII) to obtain a α-halomethyl alcohol compound of formula (XIV); and iii. performing ring closure of (XIV) by treatment with alkali, e.g. with sodium hydroxide in an appropriate solvent such as, for example, 2,2'-oxybispropane.

The foregoing sequence of reactions is more fully illustrated in the following schematic representation:

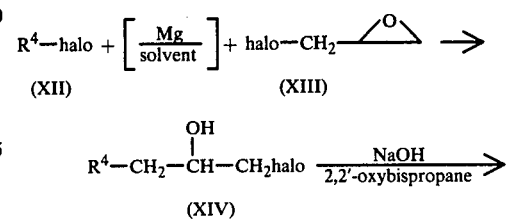

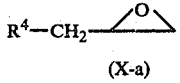

Those intermediates of formula (X) wherein R is alkyloxymethyl, alkenyloxymethyl, 2-propynyloxymethyl, arylmethoxymethyl or aryloxymethyl, (X-b), are conveniently obtained by the reaction of an appropriate hydroxycompound of formula (XV) wherein $R^5$ is alkyl, alkenyl, 2-propynyl, aryl or arylmethyl with an appropriate 2-halomethyloxirane of formula (XIII) following common O-alkylating procedures as generally known in the art.

Intermediates of formula (X) wherein R stands for arylthiomethyl, (X-c), may be prepared in an analogous manner by the S-alkylation of an arylthiol of formula (XVI) with a 2-halomethyloxirane of formula (XIII).

The foregoing reactions are schematically illustrated hereafter:

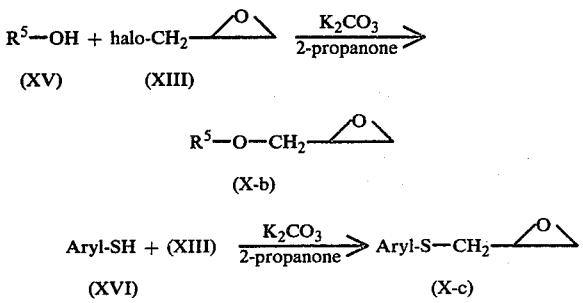

Intermediates of formula (V) wherein R stands for alkenyl may, for example, be prepared starting from an appropriate hydroxyalkylsubstituted ethanediol by ketalizing the ethanediol group with an appropriate ketone, e.g., 2-propanone, converting thereafter the remaining hydroxy group on the alkyl chain into a methanesulfonate group by the reaction with methanesulfonyl chloride, splitting off methanesulfonic acid by treatment with an appropriate strong base such as, for example, sodium hydride in a suitable solvent such as dimethylformamide, and finally liberating the free diol from the ketal by treatment with an appropriate strong mineral acid such as, for example, hydrochloric or sulfuric acid.

In a preferred manner of carrying out the aforementioned reactions, the ketone used in the ketalization step is an intermediate of formula (IX) whereby the alkenylsubstituted dioxolanes of formula (III) are directly obtained in the course of the foregoing reaction sequence.

The precursor arylketones of formula (IX) are generally known and may be prepared according to known procedures as described in the literature. Bromides are, for example, easily obtained by the bromination of the corresponding methyl aryl methanone with bromine.

The aroylmethylsubstituted imidazoles of formula (IV), a number of which are described in U.S. Pat. Nos. 3,717,655 and 3,658,813, are conveniently prepared by the reaction of (IX) with imidazole in an analogous manner as previously described for the preparation of the compounds (I) starting from imidazole and (III).

The reactive esters of formula (VII), used as intermediates in the preparation of the compounds (I-d) are easily obtained by converting the corresponding alcohol of formula (I-b) into a reactive ester thereof according to methodologies generally known in the art. For example, methanesulfonates and 4-methylbenzenesulfonates are conveniently prepared by the reaction of the alcohol with respectively methanesulfonyl chloride or 4-methylbenzenesulfonyl chloride and halides may be prepared by the reaction of the alcohol with an appropriate halogenating agent such as, for example, sulfuryl chloride, phosphor pentachloride, phosphor pentabromide, phosphoryl chloride and the like. When the reactive ester is an iodide, it is preferably prepared from the corresponding chloride or bromide by the replacement of that halogen with iodine.

From formula (I) it is evident that the compounds of this invention have two asymmetric carbon atoms in their structures, namely those located in the 2- and 4-position of the dioxolane nucleus, and consequently they exist under different stereochemical optical isomeric forms. The stereochemical optical isomeric forms of (I) and the therapeutically active acid addition salts thereof are intended to be within the scope of this invention.

The diastereomeric racemates of (I), denotes as cis and trans forms respectively, according to the rules described in "Naming and Indexing of Chemical Substances for Chemical Abstracts during the 9th Collective Period (1972–1976)", published in C. A. 1972, 76, Index Guide Section IV, p. 85, may be obtained separately by conventional methods. Appropriate methods which may advantageously be employed therefore include, for example, selective crystallization and column-chromatography. For a number of compounds the stereochemical configuration was experimentally determined. In the remaining cases it is conventionally agreed to designate the stereochemical form which is first isolated as "A" and the second as "B", without further reference to the actual stereochemical configuration.

Since the asymmetric carbon atoms are already present in the intermediates (III) it is also possible to separate cis and trans forms, or generally "A" and "B" forms at this stage, whereupon the corresponding forms of (I) may be obtained after reaction of the foregoing with imidazole as previously described. The separation of cis and trans forms of (III) may be performed by conventional methods as described hereinbefore for the separation of the compounds (I) into their cis and trans forms. When R in the intermediate of formula (III) has the meaning of a hydroxymethyl group it may be advantageous to esterify first said hydroxymethyl group with an appropriate acylhalide, e.g., benzoyl chloride whereupon the thus obtained esters are separated into their cis and trans forms, from which the acyl group is subsequently split off hydrolytically in alkaline medium yielding the corresponding forms of the desired hydroxymethylsubstituted intermediates of formula (III).

It is evident that the cis and trans diastereomeric racemates may be further resolved into their optical isomers, cis (+), cis (−), trans (+) and trans (−) by the application of methodologies known to those skilled in the art.

The compounds of formula (I) and the acid addition salts thereof are useful agents in combatting fungi and bacteria. As such they are valuable in the treatment of human beings, animals and plants suffering from pathogenic microorganisms and in the destruction of microorganisms on materials. The broad spectrum of antifungal and antibacterial activity of the compounds of formula (I) is clearly illustrated by the experimental data presented hereafter. The compounds in the tables are not listed for the purpose of limiting the invention thereto, but only in order to exemplify the useful properties of all the compounds within the scope of formula (I).

The test for antifungal activity was performed using Sabouraud's liquid medium in test tubes each containing 4.5 ml of liquid medium, autoclaved at 120° C. for 15 minutes. The substances were dissolved in 50% ethanol at a concentration of 20mg/ml and subsequently diluted with sterile distilled water to a concentration of 10mg/ml. Successive decimal dilutions were then made with distilled water to give a series of stock solutions. To each tube containing 4.5 ml of Sabouraud's liquid medium was added 0.5 ml of one of the stock solutions to give a concentration of the drug under investigation of 100 μg, 10 μg, 1 μg or 0.1 μg per ml of medium. Filamentous fungi were incubated at 25° C. for 2–3 weeks. A square block of side 2 mm. was excised and inoculated into the liquid medium. A three-day old culture on Sabouraud's liquid medium was used for yeasts, and the inoculum was 0.05 ml per tube. All the cultures were incubated at 25° C. for 14 days. The final readings were taken after two weeks and are summarized in the Tables A as follows:

++++ = complete inhibition of growth at 0.1 μg/ml
+++ = complete inhibition of growth at 1 μg/ml
++ = complete inhibition of growth at 10 μg/ml
+ = complete inhibition of growth at 100 μg/ml
0 = no effect, i.e. growth was observed at the highest concentration tested (100 μg/ml). In a first screening the drugs under investigation were tested against the following 11 fungi:

1. Microsporum canis (M. c. in the tables)
2. Ctenomyces mentagrophytes (Ct. m. in the tables)
3. Trichophyton rubrum (Tr. r. in the tables)
4. Phialophora verrucosa (Ph. v. in the tables)
5. Cryptococcus neoformans (Cr. n. in the tables)
6. Candida tropicalis (C. tr. in the tables)
7. Candida albicans (C. alb. in the tables)
8. Mucor species (Muc. in the tables)
9. Aspergillus fumigatus (A. f. in the tables)
10. Sporotrichum schenckii (Sp. s. in the tables)
11. Saprolegnia species (Sap. in the tables)

A number of the substances showing activity against the Phycomycetes Mucor at the 10 μg/ml concentration were also tested against four other species of phycomycetes, namely:

1. Absidia ramosa (Abs. r. in the tables)
2. Basidiobolus meristosporus (Bas. m. in the tables)
3. Mortierella species (Mort. in the tables)
4. Rhizopus (Rhi. in the tables).

The method used in this second screen was exactly the same as described above, and the results are given in Tables B.

Bactericidal tests were performed on cultures on phenol red dextrose broth Difco medium. The same decimal dilution techniques as described herebefore were used. The inoculum consisted of a platinum loop (5 mm. diameter) from a 24 hour broth culture. 48 Hours after incubation, subcultures were made from each culture and for the assessment of the bactericidal activity of the drugs under investigation the presence or absence of growth after 7 days incubation was scored as described above.

The substances were tested against the following gram-negative bacilli:

1. Salmonella pullorum gallinarum (SPG in the table)
2. Escherichia coli (E. coli in the table), and
3. Pseudomonas aeruginosa (Ps. aer. in the table);

and against the following gram-positive bacilli and cocci:

1. Erysipelothrix insidiosa (E. ins. in the table),
2. Staphylococcus hemolyticus (Staph. in the table), and
3. Streptococcus pyogenes (Strept. in the table).

The results are summarized in Tables C.

Tables A1

ANTIFUNGAL ACTIVITY.

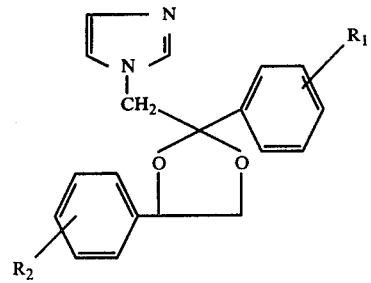

ANTIFUNGAL ACTIVITY

| $R_1$ | $R_2$ | M. c. (1) | Ct. m. (2) | Tr. r. (3) | Ph. v. (4) | Cr. n. (5) | C. tr. (6) | C. alb. (7) | Muc. (8) | A.f. (9) | Sp. s. (10) | Sap. (11) |
|---|---|---|---|---|---|---|---|---|---|---|---|---|
| 4-Cl | 4-Cl | ++++ | ++++ | ++++ | + | +++ | ++ | + | +++ | +++ | ++ | ++ |
| 4-Cl | H | ++ | +++ | +++ | + | ++ | 0 | + | + | ++ | ++ | + |
| 4-Cl | 2,4-(Cl)$_2$ | ++ | +++ | +++ | + | ++ | 0 | + | + | + | ++ | + |
| 4-Br | 4-Cl | +++ | +++ | +++ | + | + | + | 0 | 0 | ++ | ++ | + |
| 4-Br | 2,4-(Cl)$_2$ | ++ | ++ | +++ | 0 | 0 | 0 | 0 | + | 0 | + | 0 |
| 2,4-(Cl)$_2$ | H | +++ | +++ | +++ | + | + | 0 | + | + | +++ | ++ | + |
| 4-OCH$_3$ | 4-Cl | +++ | +++ | ++ | + | 0 | 0 | 0 | + | +++ | ++ | + |
| H | 2,4-(Cl)$_2$ | ++ | +++ | +++ | + | ++ | 0 | 0 | + | ++ | ++ | + |
| 2,4-(Cl)$_2$ | 4-Cl | +++ | +++ | +++ | + | +++ | ++ | + | +++ | +++ | ++ | + |
| H | 4-Cl | +++ | +++ | +++ | + | ++ | + | 0 | + | ++ | ++ | + |
| 4-Cl | 2-Cl | ++ | +++ | +++ | + | ++ | 0 | 0 | + | + | +++ | ++ |
| 2-Cl | 2,4-(Cl)$_2$ | +++ | +++ | +++ | + | +++ | 0 | 0 | 0 | +++ | +++ | ++ |
| 4-Br | 2-Cl | +++ | +++ | +++ | + | +++ | 0 | + | ++ | + | ++ | + |
| 2-Cl | 4-Cl | +++ | +++ | +++ | + | + | + | + | + | +++ | ++ | ++ |
| 2,4-(Cl)$_2$ | 2,4-(Cl)$_2$ | ++ | +++ | +++ | + | +++ | 0 | 0 | + | +++ | ++ | + |
| 4-Br | H | +++ | +++ | +++ | + | ++ | 0 | + | + | + | + | + |

Tables A1-continued
ANTIFUNGAL ACTIVITY.

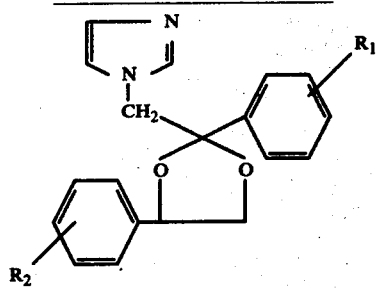

ANTIFUNGAL ACTIVITY

| R₁ | R₂ | M. c. (1) | Ct. m. (2) | Tr. r. (3) | Ph. v. (4) | Cr. n. (5) | C. tr. (6) | C. alb. (7) | Muc. (8) | A.f. (9) | Sp. s. (10) | Sap. (11) |
|---|---|---|---|---|---|---|---|---|---|---|---|---|
| H | 4-Br | +++ | +++ | +++ | + | ++ | 0 | + | + | ++ | ++ | + |
| 4-CH₃ | 2,4-(Cl)₂ | ++ | +++ | +++ | + | ++ | 0 | 0 | + | + | ++ | + |
| 4-Br | 4-Br | +++ | +++ | +++ | + | +++ | + | 0 | ++ | +++ | ++ | + |
| 2,4-(Cl)₂ | 2-Cl | ++ | +++ | +++ | + | +++ | + | + | + | + | ++ | + |
| 4-CH₃ | 4-Cl | +++ | +++ | +++ | + | +++ | + | 0 | ++ | +++ | ++ | + |
| 2,4-(Cl)₂ | 4-Br | +++ | +++ | +++ | + | +++ | ++ | + | +++ | +++ | ++ | + |
| 4-Cl | 4-Br | +++ | +++ | +++ | + | +++ | ++ | ++ | ++ | +++ | ++ | +++ |
| 4-CH₃ | 4-Br | +++ | +++ | +++ | 0 | 0 | 0 | 0 | 0 | +++ | 0 | ++ |
| 3-Cl | 2,4-(Cl)₂ | + | ++ | +++ | 0 | + | 0 | 0 | + | + | ++ | + |
| 2-Cl | 4-Br | +++ | +++ | +++ | ++ | +++ | ++ | + | ++ | +++ | ++ | ++ |
| 4-CH₃ | 2-Cl | ++ | +++ | +++ | + | + | 0 | 0 | + | + | ++ | + |
| 4-Cl | 4-CH₃ | +++ | +++ | +++ | + | +++ | 0 | + | + | +++ | ++ | + |
| 4-Br | 4-CH₃ | +++ | ++ | +++ | + | ++ | 0 | ++ | ++ | +++ | ++ | + |
| 4-Cl | 4-F | +++ | +++ | +++ | + | ++ | + | + | ++ | +++ | ++ | + |
| 4-Br | 4-F | +++ | +++ | +++ | + | ++ | + | + | +++ | +++ | ++ | + |

Tables A2
ANTIFUNGAL ACTIVITY.

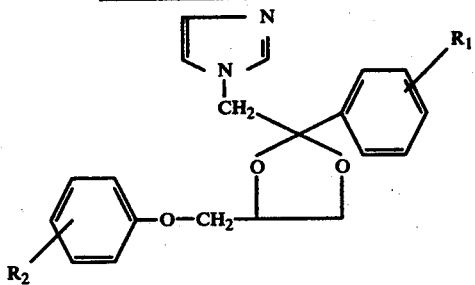

ANTIFUNGAL ACTIVITY

| R₁ | R₂ | Isomer | M. c. (1) | Ct. m. (2) | Tr. r. (3) | Ph. v. (4) | Cr. n. (5) |
|---|---|---|---|---|---|---|---|
| 4-Cl | 2-CH₃, 4-Cl | cis | 0 | ++ | ++ | 0 | + |
| 4-Cl | 4-CH₃ | trans | ++ | ++++ | +++ | ++ | +++ |
| 4-Cl | 2-CH₃,4-Cl | trans | + | +++ | +++ | 0 | ++ |
| 4-Cl | 4-CH₃ | cis | +++ | ++++ | ++++ | ++ | +++ |
| 4-Cl | 4-Cl | A | +++ | ++++ | ++++ | 0 | ++ |
| 4-Cl | 4-Cl | B | ++ | ++++ | +++ | + | + |
| 4-Cl | 4-F | cis | +++ | ++++ | ++++ | + | + |
| 4-Cl | 2-CH₃ | A | ++ | +++ | +++ | + | ++ |
| 4-Cl | 2-Cl | A | 0 | +++ | +++ | 0 | ++++ |
| 4-Cl | 2-CH₃ | B | ++ | ++++ | ++++ | + | ++ |
| 4-Cl | 2,4-(Cl)₂ | B | ++ | +++ | +++ | 0 | ++ |
| 4-Cl | 4-OCH₃ | A | +++ | ++++ | ++++ | + | +++ |
| 4-Cl | 4-F | trans | ++ | ++++ | +++ | + | ++ |
| 4-Cl | 4-OCH₃ | B | + | ++++ | ++ | + | ++ |
| 4-Cl | 2,6-(Cl)₂ | A | + | ++++ | ++++ | 0 | ++ |
| 4-Cl | 2-Cl | B | ++ | +++ | ++++ | + | + |
| 4-Cl | 2,6-(Cl)₂ | B | ++ | ++ | +++ | + | + |
| 2,4-(Cl)₂ | 4-CH₃ | B | ++ | ++ | ++ | + | ++ |
| 2,4-(Cl)₂ | 4-F | A | ++ | ++ | ++ | ++ | ++ |
| 2,4-(Cl)₂ | 2-CH₃ | A | +++ | +++ | +++ | + | +++ |
| 2,4-(Cl)₂ | 4-CH₃ | A | ++ | +++ | +++ | ++ | +++ |
| 2,4-(Cl)₂ | 4-OCH₃ | A | ++++ | ++++ | ++++ | ++ | ++++ |
| 2,4-(Cl)₂ | 4-Cl | cis | ++++ | ++++ | ++++ | ++ | ++++ |
| 2,4-(Cl)₂ | 2-CH₃ | B | ++ | +++ | +++ | + | ++ |
| 2,4-(Cl)₂ | 2,4-(Cl)₂ | A | ++ | +++ | +++ | 0 | +++ |
| 2,4-(Cl)₂ | 4-Cl | trans | ++ | +++ | +++ | + | ++ |
| 2,4-(Cl)₂ | 4-Br | A | ++ | +++ | +++ | + | +++ |
| 2,4-(Cl)₂ | 2,4-(Cl)₂ | B | ++ | +++ | +++ | + | ++ |
| 2,4-(Cl)₂ | H | A | +++ | +++ | +++ | ++ | +++ |
| 2,4-(Cl)₂ | 3,4-(Cl)₂ | A | +++ | +++ | +++ | + | +++ |
| 2,4-(Cl)₂ | 3-Cl | A | +++ | +++ | +++ | + | +++ |
| 2,4-(Cl)₂ | 2-Cl | A | +++ | +++ | +++ | + | +++ |
| 2,4-(Cl)₂ | 2-CH₃, 4-Cl | A + B | +++ | +++ | +++ | 0 | +++ |
| 2,4-(Cl)₂ | 2-Cl | B | ++ | +++ | +++ | 0 | ++ |

Tables A2-continued
ANTIFUNGAL ACTIVITY.

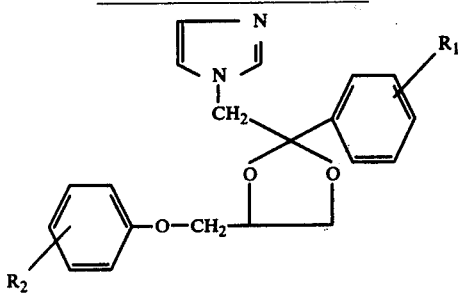

| $R_1$ | $R_2$ | Isomer | | | | | |
|---|---|---|---|---|---|---|---|
| 2,4-(Cl)$_2$ | 2,6-(Cl)$_2$ | A | ++ | +++ | +++ | + | +++ |
| 2,4-(Cl)$_2$ | 3,5-(CH$_3$)$_2$, 4-Cl | A | 0 | 0 | ++ | 0 | 0 |
| 2,4-(Cl)$_2$ | 2,4-(Br)$_2$ | A | 0 | 0 | + | 0 | +++ |
| 2,4-(Cl)$_2$ | 4-CN | A | +++ | +++ | +++ | ++ | +++ |
| 2,4-(Cl)$_2$ | 2-Br | cis | ++ | +++ | +++ | 0 | +++ |
| 2,4-(Cl)$_2$ | 2-OCH$_3$ | A | ++ | +++ | +++ | + | +++ |
| 2,4-(Cl)$_2$ | 2-Br | trans | ++ | +++ | ++ | 0 | +++ |
| 2,4-(Cl)$_2$ | 2,4,6-(Cl)$_3$ | A | 0 | +++ | ++ | 0 | +++ |
| 2,4-(Cl)$_2$ | 2,5-(CH$_3$)$_2$ | A | +++ | +++ | +++ | 0 | +++ |
| 2,4-(Cl)$_2$ | 2,5-(CH$_3$)$_2$ | B | ++ | ++ | +++ | 0 | ++ |
| 2,4-(Cl)$_2$ | 2-Cl,4-tert. but. | A | 0 | + | ++++ | 0 | ++++ |
| 2,4-(Cl)$_2$ | 2,4,5-(Cl)$_3$ | A | 0 | 0 | 0 | 0 | 0 |
| 2,4-(Cl)$_2$ | 2-Cl,4-tert. but. | B | + | + | ++ | 0 | + |
| 2,4-(Cl)$_2$ | 2,4,5-(Cl)$_3$ | B | + | ++ | ++ | 0 | ++++ |
| 2,4-(Cl)$_2$ | 2,5-(Br)$_2$,4-CH$_3$ | A | + | ++ | ++++ | 0 | ++++ |
| 2,4-(Cl)$_2$ | 2-F | A | ++ | ++++ | ++++ | + | ++++ |
| 4-CH$_3$ | 4-Br | A | ++++ | ++++ | ++++ | ++ | ++++ |
| 4-Cl | 4-Br | A | ++++ | ++++ | ++++ | ++ | ++++ |
| 4-Br | 4-Br | A | ++++ | ++++ | ++++ | + | ++++ |
| 2,4-(Cl)$_2$ | 2-OC$_2$H$_5$ | A | ++ | ++++ | ++++ | + | ++++ |
| 2-Cl | 4-Br | A + B | ++ | ++++ | ++ | ++ | ++++ |
| 2-Cl | 4-Br | B | ++ | ++++ | ++++ | ++ | ++++ |
| H | 4-Br | A | ++ | ++++ | ++++ | + | ++++ |
| 2-Br | 4-Br | A | ++ | ++++ | ++++ | ++ | ++++ |
| 2-Br | 4-Br | B | ++ | ++++ | ++++ | ++ | ++ |
| 2,4-(Cl)$_2$ | 4-C$_6$H$_5$ | A + B | 0 | ++++ | ++++ | 0 | ++++ |
| 2,4-(Cl)$_2$ | 4-C$_6$H$_5$ | B | 0 | 0 | 0 | 0 | 0 |
| 2,4-(Cl)$_2$ | 2,6-(CH$_3$)$_2$ | A | ++++ | ++++ | ++++ | 0 | + |
| 2,4-(Cl)$_2$ | 4-Br | B | ++ | ++++ | ++++ | + | 0 |
| 2,4-(Cl)$_2$ | 2,6-(CH$_3$)$_2$ | A + B | ++ | ++++ | ++++ | 0 | 0 |
| 2,4-(Cl)$_2$ | 3,5-(CH$_3$)$_2$ | A | +++ | +++ | +++ | 0 | +++ |
| 2,4-(Cl)$_2$ | 4-iC$_3$H$_7$ | A + B | +++ | +++ | +++ | + | +++ |
| 2,4-(Cl)$_2$ | 2-Cl,6-CH$_3$ | A | +++ | +++ | +++ | 0 | ++ |
| 2,4-(Cl)$_2$ | 4-tert.but. | A | ++ | ++++ | ++++ | 0 | ++ |
| 2,4-(Cl)$_2$ | 3,5-(Cl)$_2$ | A | ++++ | ++++ | ++++ | 0 | 0 |
| 2,4-(Cl)$_2$ | 3-CH$_3$,4-Cl | A | ++++ | ++++ | ++++ | + | +++ |

ANTIFUNGAL ACTIVITY

| $R_1$ | $R_2$ | Isomer | C.tr. (6) | C. alb. (7) | Muc. (8) | A.f. (9) | Sp. s. (10) | Sap. (11) |
|---|---|---|---|---|---|---|---|---|
| 4-Cl | 2-CH$_3$, 4-Cl | cis | 0 | 0 | 0 | 0 | 0 | 0 |
| 4-Cl | 4-CH$_3$ | trans | 0 | + | + | ++ | ++ | ++ |
| 4-Cl | 2-CH$_3$,4-Cl | trans | 0 | 0 | ++ | + | ++ | + |
| 4-Cl | 4-CH$_3$ | cis | 0 | 0 | + | +++ | +++ | ++ |
| 4-Cl | 4-Cl | A | 0 | 0 | + | +++ | 0 | + |
| 4-Cl | 4-Cl | B | 0 | 0 | ++ | ++ | ++ | ++ |
| 4-Cl | 4-F | cis | 0 | 0 | ++ | ++ | ++ | ++ |
| 4-Cl | 2-CH$_3$ | A | 0 | + | ++ | ++ | ++ | |
| 4-Cl | 2-Cl | A | 0 | 0 | 0 | 0 | 0 | 0 |
| 4-Cl | 2-CH$_3$ | B | 0 | + | 0 | ++ | ++ | + |
| 4-Cl | 2,4-(Cl)$_2$ | B | 0 | 0 | ++ | ++ | ++ | + |
| 4-Cl | 4-OCH$_3$ | A | 0 | 0 | 0 | ++ | ++ | ++ |
| 4-Cl | 4-F | trans | 0 | 0 | + | + | + | ++ |
| 4-Cl | 4-OCH$_3$ | B | 0 | 0 | 0 | + | ++ | ++ |
| 4-Cl | 2,6-(Cl)$_2$ | A | 0 | 0 | ++ | ++ | ++ | + |
| 4-Cl | 2-Cl | B | 0 | 0 | 0 | ++ | ++ | + |
| 4-Cl | 2,6-(Cl)$_2$ | B | 0 | 0 | + | ++ | + | 0 |
| 2,4-(Cl)$_2$ | 4-CH$_3$ | B | 0 | 0 | + | ++ | ++ | ++ |
| 2,4-(Cl)$_2$ | 4-F | A | ++ | 0 | + | ++ | ++ | ++ |
| 2,4-(Cl)$_2$ | 2-CH$_3$ | A | 0 | 0 | +++ | ++ | ++ | + |
| 2,4-(Cl)$_2$ | 4-CH$_3$ | A | 0 | 0 | +++ | +++ | +++ | ++ |
| 2,4-(Cl)$_2$ | 4-OCH$_3$ | A | 0 | 0 | ++ | ++ | ++++ | +++ |
| 2,4-(Cl)$_2$ | 4-Cl | cis | 0 | 0 | +++ | ++ | +++ | ++ |
| 2,4-(Cl)$_2$ | 2-CH$_3$ | B | 0 | 0 | ++ | ++ | ++ | + |
| 2,4-(Cl)$_2$ | 2,4-(Cl)$_2$ | A | 0 | 0 | 0 | 0 | ++ | + |
| 2,4-(Cl)$_2$ | 4-Cl | trans | 0 | 0 | ++ | ++ | ++ | + |
| 2,4-(Cl)$_2$ | 4-Br | A | +++ | 0 | ++ | +++ | ++ | ++ |
| 2,4-(Cl)$_2$ | 2,4-(Cl)$_2$ | B | 0 | 0 | + | + | ++ | + |
| 2,4-(Cl)$_2$ | H | A | ++ | 0 | ++ | +++ | +++ | ++ |
| 2,4-(Cl)$_2$ | 3,4-(Cl)$_2$ | A | 0 | 0 | ++ | +++ | +++ | + |
| 2,4-(Cl)$_2$ | 3-Cl | A | ++ | 0 | ++ | +++ | +++ | + |
| 2,4-(Cl)$_2$ | 2-Cl | A | ++ | + | ++ | +++ | +++ | + |
| 2,4-(Cl)$_2$ | 2-CH$_3$,4-Cl | A + B | 0 | 0 | ++ | ++ | ++ | + |
| 2,4-(Cl)$_2$ | 2-Cl | B | 0 | 0 | 0 | + | ++ | + |
| 2,4-(Cl)$_2$ | 2,6-(Cl)$_2$ | A | 0 | 0 | 0 | ++ | ++ | + |
| 2,4-(Cl)$_2$ | 3,5-(CH$_3$)$_2$,4-Cl | A | 0 | 0 | 0 | 0 | 0 | 0 |
| 2,4-(Cl)$_2$ | 2,4-(Br)$_2$ | A | 0 | 0 | 0 | 0 | 0 | 0 |
| 2,4-(Cl)$_2$ | 4-CN | A | ++ | 0 | 0 | ++ | + | ++ |

Tables A2-continued

ANTIFUNGAL ACTIVITY.

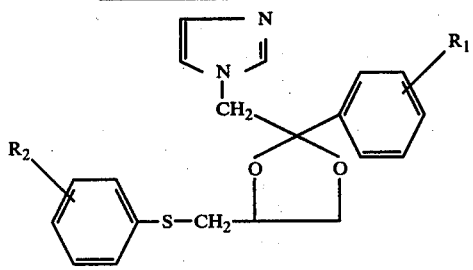

| $R_1$ | $R_2$ | Isomer | | | | | | | |
|---|---|---|---|---|---|---|---|---|---|
| 2,4-(Cl)$_2$ | 2-Br | cis | 0 | 0 | +++ | ++ | ++ | + | |
| 2,4-(Cl)$_2$ | 2-OCH$_3$ | A | + | 0 | 0 | ++ | ++ | + | |
| 2,4-(Cl)$_2$ | 2-Br | trans | 0 | 0 | + | ++ | ++ | + | |
| 2,4-(Cl)$_2$ | 2,4,6-(Cl)$_3$ | A | + | 0 | 0 | 0 | 0 | 0 | |
| 2,4-(Cl)$_2$ | 2,5-(CH$_3$)$_2$ | A | 0 | 0 | + | ++ | ++ | + | |
| 2,4-(Cl)$_2$ | 2,5-(CH$_3$)$_2$ | B | 0 | 0 | 0 | ++ | + | + | |
| 2,4-(Cl)$_2$ | 2-Cl,4-tert.but. | A | 0 | 0 | 0 | 0 | 0 | 0 | |
| 2,4-(Cl)$_2$ | 2,4,5-(Cl)$_3$ | A | 0 | 0 | 0 | 0 | 0 | 0 | |
| 2,4-(Cl)$_2$ | 2-Cl,4-tert.but. | B | 0 | 0 | 0 | + | 0 | 0 | |
| 2,4-(Cl)$_2$ | 2,4,5-(Cl)$_3$ | B | 0 | 0 | 0 | 0 | 0 | 0 | |
| 2,4-(Cl)$_2$ | 2,5-(Br)$_2$,4-CH$_3$ | A | 0 | 0 | + | + | + | 0 | |
| 2,4-(Cl)$_2$ | 2-F | A | ++ | + | ++ | ++++ | ++++ | ++ | |
| 4-CH$_3$ | 4-Br | A | + | 0 | 0 | ++++ | ++++ | ++ | |
| 4-Cl | 4-Br | A | 0 | 0 | 0 | ++++ | ++ | + | |
| 4-Br | 4-Br | A | 0 | 0 | 0 | + | + | ++ | |
| 2,4-(Cl)$_2$ | 2-OC$_2$H$_5$ | A | + | 0 | 0 | ++ | ++ | + | |
| 2-Cl | 4-Br | A + B | + | + | 0 | ++ | ++ | ++ | |
| 2-Cl | 4-Br | B | 0 | + | + | + | ++++ | ++ | |
| H | 4-Br | A | 0 | 0 | 0 | ++ | ++ | ++ | |
| 2-Br | 4-Br | A | ++ | + | ++ | ++ | ++ | ++ | |
| 2-Br | 4-Br | B | 0 | 0 | 0 | ++ | +'++ | ++ | |
| 2,4-(Cl)$_2$ | 4-C$_6$H$_5$ | A + B | 0 | 0 | 0 | 0 | 0 | 0 | |
| 2,4-(Cl)$_2$ | 4-C$_6$H$_5$ | B | 0 | 0 | 0 | 0 | 0 | 0 | |
| 2,4-(Cl)$_2$ | 2,6-(CH$_3$)$_2$ | A | + | 0 | + | ++ | + | + | |
| 2,4-(Cl)$_2$ | 4-Br | B | 0 | 0 | ++ | + | +++ | + | |
| 2,4-(Cl)$_2$ | 2,6-(CH$_3$)$_2$ | A + B | 0 | 0 | + | + | ++ | 0 | |
| 2,4-(Cl)$_2$ | 3,5-(CH$_3$)$_2$ | A | 0 | 0 | 0 | ++ | 0 | 0 | |
| 2,4-(Cl)$_2$ | 4-iC$_3$H$_7$ | A + B | +++ | 0 | + | +++ | ++ | + | |
| 2,4-(Cl)$_2$ | 2-Cl,6-CH$_3$ | A | +++ | + | +++ | +++ | +++ | + | |
| 2,4-(Cl)$_2$ | 4-tert.but. | A | 0 | 0 | 0 | + | + | 0 | |
| 2,4-(Cl)$_2$ | 3,5-(Cl)$_2$ | A | 0 | 0 | ++ | ++ | 0 | 0 | |
| 2,4-(Cl)$_2$ | 3-CH$_3$,4-Cl | A | 0 | 0 | + | ++++ | ++ | + | |

Tables A3

ANTIFUNGAL ACTIVITY

| $R_1$ | $R_2$ | Isomer | M. c. (1) | Ct. m. (2) | Tr. R. (3) | Ph. V. (4) | Cr. n. (5) | C. tr. (6) | C. alb. (7) | Muc. (8) | A.f. (9) | Sp. s. (10) | Sap. (11) |
|---|---|---|---|---|---|---|---|---|---|---|---|---|---|
| 2,4-(Cl)$_2$ | 4-Br | A + B | ++++ | ++++ | ++++ | + | ++++ | ++ | + | ++ | ++ | ++++ | + |
| 2,4-(Cl)$_2$ | H | A + B | ++++ | ++++ | ++++ | ++ | ++++ | ++ | + | +++ | ++ | ++++ | ++ |

Tables A4

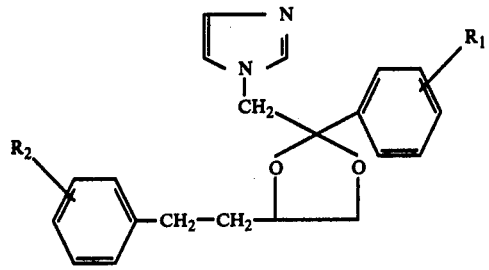

| | | | ANTIFUNGAL ACTIVITY | | | | | | | | | |
|---|---|---|---|---|---|---|---|---|---|---|---|---|
| $R_1$ | $R_2$ | Isomer | M. c. (1) | Ct. m. (2) | Tr. R. (3) | Ph. V. (4) | Cr. n. (5) | C. tr. (6) | C. alb. (7) | Muc. (8) | A.f. (9) | Sp. s. (10) | Sap. (11) |
| 2,4-(Cl)$_2$ | 2-Cl | | ++++ | ++++ | ++++ | + | ++++ | ++ | 0 | ++ | ++++ | ++ | + |
| 2,4-(Cl)$_2$ | 2,4-(Cl)$_2$ | | ++ | ++++ | ++++ | 0 | ++++ | ++ | 0 | ++ | ++ | ++ | + |
| 2,4-(Cl)$_2$ | 2,6-(Cl)$_2$ | A + B | ++ | ++++ | ++++ | 0 | ++++ | 0 | 0 | ++ | ++ | ++ | 0 |
| 2,4-(Cl)$_2$ | 4-OCH$_3$ | A + B | ++++ | ++++ | ++++ | + | ++++ | ++ | 0 | 0 | ++++ | ++ | + |
| 2,4-(Cl)$_2$ | 4-Cl | | ++++ | ++++ | ++++ | + | ++++ | ++ | ++ | ++ | ++ | ++++ | + |
| 2,4-(Cl)$_2$ | H | | ++++ | ++++ | ++++ | + | ++++ | ++ | + | ++ | ++++ | ++++ | + |

Tables A5

ANTIFUNGAL ACTIVITY

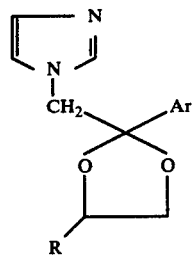

| | | ANTIFUNGAL ACTIVITY | | | | | | | | | |
|---|---|---|---|---|---|---|---|---|---|---|---|
| Ar | R | M. c. (1) | Ct. m. (2) | Tr. r. (3) | Ph. v. (4) | Cr. n. (5) | C. tr. (6) | C. alb. (7) | Muc. (8) | A.f. (9) | Sp. s. (10) | Sap. (11) |
| 2,4-Cl$_2$—C$_6$H$_3$ | C$_2$H$_5$ | +++ | +++ | +++ | ++ | +++ | +++ | o | + | +++ | ++ | ++ |
| 2-Cl—C$_6$H$_4$ | C$_2$H$_5$ | +++ | +++ | +++ | + | + | + | o | o | ++ | + | ++ |
| 2-CH$_3$—C$_6$H$_4$ | C$_2$H$_5$ | ++ | +++ | +++ | + | + | + | o | o | ++ | + | + |
| 4-CH$_3$—C$_6$H$_4$ | C$_2$H$_5$ | ++ | +++ | +++ | + | + | + | o | o | + | o | + |
| 2,3,4-(Cl)$_3$—C$_6$H$_2$ | C$_2$H$_5$ | +++ | +++ | +++ | + | + | + | ++ | + | ++ | ++ | + |
| 2-Br—C$_6$H$_4$ | C$_2$H$_5$ | +++ | +++ | +++ | + | + | + | + | o | +++ | ++ | ++ |
| 2,3-(Cl)$_2$—C$_6$H$_3$ | C$_2$H$_5$ | +++ | +++ | +++ | + | + | o | + | o | ++ | + | + |
| 2-Cl,4-F—C$_6$H$_3$ | C$_2$H$_5$ | +++ | +++ | +++ | + | ++ | ++ | + | o | +++ | + | + |
| 4-Br—C$_6$H$_4$ | C$_2$H$_5$ | +++ | +++ | +++ | + | + | + | + | o | ++ | + | + |
| 3-Cl—C$_6$H$_4$ | C$_2$H$_5$ | ++ | +++ | +++ | + | ++ | ++ | + | + | +++ | ++ | ++ |
| 2-Cl,4-Br—C$_6$H$_3$ | C$_2$H$_5$ | +++ | +++ | +++ | ++ | +++ | ++ | o | + | +++ | ++ | ++ |
| 2,4-(Br)$_2$—C$_6$H$_3$ | C$_2$H$_5$ | +++ | +++ | +++ | ++ | +++ | ++ | o | + | +++ | ++ | ++ |
| 4-OCH$_3$—C$_6$H$_4$ | C$_2$H$_5$ | ++ | ++ | +++ | o | o | o | o | o | + | o | + |
| 2-thienyl | C$_2$H$_5$ | +++ | +++ | +++ | + | o | + | o | o | + | o | + |
| 2-CH$_3$,4-Cl—C$_6$H$_3$ | C$_2$H$_5$ | +++ | +++ | +++ | ++ | +++ | ++ | + | o | +++ | ++ | +++ |
| 2-Cl,4-OCH$_3$—C$_6$H$_3$ | C$_2$H$_5$ | +++ | +++ | +++ | + | + | + | o | o | +++ | + | + |
| 3,4,5-(Cl)$_3$—C$_6$H$_2$ | C$_2$H$_5$ | ++ | ++ | +++ | + | + | o | + | + | + | + | + |
| 2-naphthyl | C$_2$H$_5$ | ++ | +++ | +++ | + | + | o | + | + | + | + | + |
| 5-Cl-2-thienyl | C$_2$H$_5$ | ++ | +++ | +++ | + | + | + | o | o | ++ | + | + |
| 2,4-(Cl)$_2$—C$_6$H$_3$ | nC$_3$H$_7$ | +++ | +++ | +++ | ++ | +++ | ++ | + | ++ | +++ | ++ | ++ |
| 2,4-(Cl)$_2$—C$_6$H$_3$ | nC$_4$H$_9$ | +++ | ++ | +++ | ++ | +++ | ++ | o | + | +++ | +++ | ++ |
| 2,4-(Cl)$_2$—C$_6$H$_3$ | nC$_5$H$_{11}$ | +++ | +++ | +++ | + | +++ | ++ | ++ | ++ | ++ | +++ | ++ |
| 2,4-(Cl)$_2$—C$_6$H$_3$ | nC$_6$H$_{13}$ | +++ | +++ | +++ | + | +++ | o | ++ | ++ | +++ | +++ | + |
| 2,4-(Cl)$_2$—C$_6$H$_3$ | nC$_7$H$_{15}$ | ++ | +++ | +++ | + | +++ | o | o | ++ | ++ | +++ | + |
| 2,4-(Cl)$_2$—C$_6$H$_3$ | nC$_8$H$_{17}$ | ++ | +++ | +++ | + | ++ | o | o | + | + | ++ | + |
| 2,4-(Cl)$_2$—C$_6$H$_3$ | Cl—CH$_2$ | +++ | +++ | +++ | ++ | ++ | + | o | + | +++ | +++ | ++ |

Tables A6

ANTIFUNGAL ACTIVITY

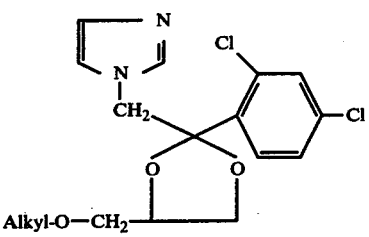

ANTIFUNGAL ACTIVITY

| Alkyl | isomer | M. c. (1) | Ct. m. (2) | Tr. r. (3) | Ph. v. (4) | Cr. n. (5) | C. tr. (6) | C. alb. (7) | Muc. (8) | A.f. (9) | Sp. s. (10) | Sap. (11) |
|---|---|---|---|---|---|---|---|---|---|---|---|---|
| $CH_3$ | cis | ++ | +++ | +++ | ++ | ++ | ++ | o | o | ++ | + | ++ |
| $C_2H_5$ | trans | ++ | +++ | ++ | + | + | o | o | o | + | + | + |
| $nC_3H_7$ | cis | ++ | +++ | +++ | ++ | +++ | ++ | o | o | ++ | ++ | ++ |
| $nC_4H_9$ | A + B | ++ | +++ | +++ | + | ++ | + | + | + | + | ++ | ++ |
| $nC_5H_{11}$ | cis | ++ | +++ | +++ | + | +++ | ++ | o | ++ | ++ | ++ | ++ |
| $nC_6H_{13}$ | cis | ++ | +++ | +++ | + | +++ | ++ | o | + | + | ++ | + |
| $nC_7H_{15}$ | cis | + | +++ | +++ | + | +++ | o | o | + | + | ++ | + |
| $nC_8H_{17}$ | cis | + | +++ | +++ | + | +++ | o | o | + | o | ++ | o |

Tables A7

ANTIFUNGAL ACTIVITY

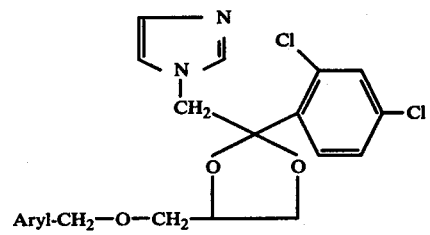

ANTIFUNGAL ACTIVITY

| Aryl | isomer | M. c. (1) | Ct. m. (2) | Tr. r. (3) | Ph. v. (4) | Cr. n. (5) | C. tr. (6) | C. alb. (7) | Muc. (8) | A.f. (9) | Sp. s. (10) | Sap. (11) |
|---|---|---|---|---|---|---|---|---|---|---|---|---|
| $4-(C_6H_5)-C_6H_4$ | cis | o | +++ | ++ | o | ++ | o | o | o | o | o | o |
| $4-(C_6H_5)-C_6H_4$ | trans | o | +++ | + | o | o | o | o | o | o | o | o |
| $4-Br-C_6H_4$ | cis | +++ | +++ | +++ | + | +++ | + | + | +++ | ++ | ++ | ++ |
| $2,4-(Cl)_2-C_6H_3$ | cis | +++ | +++ | +++ | o | +++ | o | o | + | ++ | ++ | + |
| $2,4-(Cl)_2-C_6H_3$ | trans | + | +++ | ++ | o | o | o | o | + | o | ++ | o |

Tables A8

ANTIFUNGAL ACTIVITY

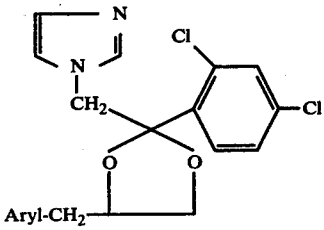

ANTIFUNGAL ACTIVITY

| Aryl | M.c. (1) | Ct.m. (2) | Tr.r. (3) | Ph.v. (4) | Cr.n. (5) | C.tr. (6) | C.alb. (7) | Muc. (8) | A.f. (9) | Sp. s. (10) | Sap. (11) |
|---|---|---|---|---|---|---|---|---|---|---|---|
| $C_6H_5$ | +++ | +++ | +++ | + | +++ | ++ | + | ++ | +++ | ++ | ++ |
| $4-Cl-C_6H_4$ | +++ | +++ | +++ | + | +++ | ++ | ++ | ++ | ++ | ++ | + |
| $4-F-C_6H_4$ | +++ | +++ | +++ | + | +++ | ++ | + | +++ | ++ | ++ | ++ |
| $4-CH_3-C_6H_4$ | +++ | +++ | +++ | + | +++ | o | ++ | ++ | ++ | ++ | ++ |
| $4-Br-C_6H_4$ | +++ | +++ | +++ | + | +++ | o | ++ | +++ | ++ | ++ | + |
| $4-OCH_3-C_6H_4$ | +++ | +++ | +++ | ++ | +++ | + | o | +++ | +++ | ++ | ++ |
| $4-(C_6H_5)-C_6H_4$ | ++ | +++ | +++ | o | + | o | o | ++ | + | + | + |

Table B

ACTIVITY AGAINST PHYCOMYCTES

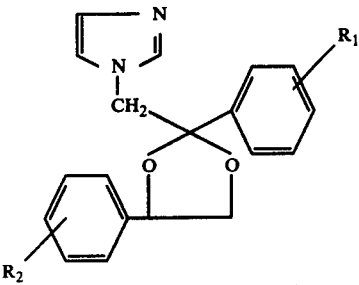

| $R_1$ | $R_2$ | Abs.r. | Bas.m. | Mort. | Rhi. |
|---|---|---|---|---|---|
| 2,4-$(Cl)_2$ | 4-Cl | ++ | ++ | + | ++ |
| 4-Br | 2-Cl | + | + | + | ++ |
| 4-Br | 4-Br | +++ | ++ | ++ | ++ |
| 4-$CH_3$ | 4-Cl | ++ | + | + | + |
| 2,4-$(Cl)_2$ | 4-Br | +++ | ++ | ++ | ++ |
| 4-Cl | 4-Br | +++ | ++ | ++ | ++ |
| 2-Cl | 4-Br | ++ | ++ | + | ++ |
| 4-Br | 4-$CH_3$ | ++ | ++ | + | ++ |
| 4-Cl | 4-F | ++ | ++ | + | + |
| 4-Br | 4-F | ++ | ++ | + | ++ |

Table B-continued

ACTIVITY AGAINST PHYCOMYCTES

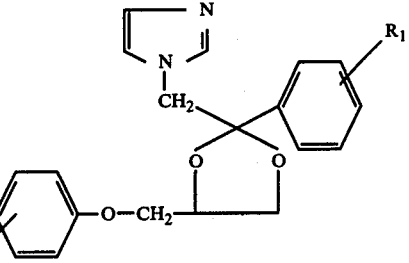

| $R_1$ | $R_2$ | Isomer | Abs.r. | Bas.m. | Mort. | Rhi. |
|---|---|---|---|---|---|---|
| 4-Cl | 4-Cl | B | +++ | + | + | + |
| 4-Cl | 4-F | cis | ++ | + | + | + |
| 4-Cl | 2-$CH_3$ | A | ++ | ++ | + | + |
| 4-Cl | 2,4-$(Cl)_2$ | B | +++ | ++ | ++ | + |
| 2,4-$(Cl)_2$ | 2-$CH_3$ | A | + | + | + | + |
| 2,4-$(Cl)_2$ | 4-Cl | trans | ++ | + | ++ | + |
| 2,4-$(Cl)_2$ | 2-$CH_3$,4-Cl | A + B | ++ | ++ | + | + |
| 4-Cl | 2,6-$(Cl)_2$ | A | ++ | + | + | + |
| 2,4-$(Cl)_2$ | 2-$CH_3$ | A | ++ | ++ | + | + |
| 2,4-$(Cl)_2$ | 4-$CH_3$ | A | + | ++ | + | + |
| 2,4-$(Cl)_2$ | 4-$OCH_3$ | A | ++ | ++ | + | + |
| 2,4-$(Cl)_2$ | 4-Cl | cis | ++ | ++ | + | + |
| 2,4-$(Cl)_2$ | 4-Br | A | +++ | ++ | ++ | ++ |
| 2,4-$(Cl)_2$ | H | A | ++ | ++ | + | + |
| 2,4-$(Cl)_2$ | 3,4-$(Cl)_2$ | A | +++ | +++ | + | ++ |
| 2,4-$(Cl)_2$ | 3-Cl | A | ++ | +++ | ++ | ++ |
| 2,4-$(Cl)_2$ | 2-Cl | A | +++ | ++ | + | + |
| 2,4-$(Cl)_2$ | 2-Br | cis | ++ | ++ | + | + |

Tabble C1

BACTERIOSTATIC AND BACTERIOCIDAL ACTIVITY
The table summarizes the activity against the gram-positive bacteria.

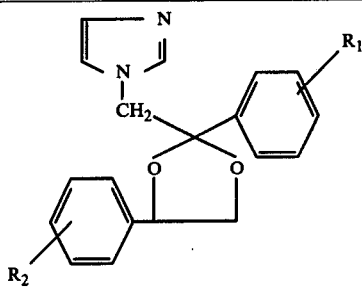

| $R_1$ | $R_2$ | bacteriostatic activity | | | bacteriocidal activity | | |
|---|---|---|---|---|---|---|---|
|  |  | E. ins. | Staph. | Strept. | E. ins. | Staph. | Strept. |
| 4-Cl | 4-Cl | ++ | ++ | ++ | ++ | ++ | ++ |
| 4-Cl | H | ++ | ++ | +++ | ++ | + | +++ |
| 4-Cl | 2,4-$(Cl)_2$ | +++ | ++ | +++ | ++ | ++ | +++ |
| 4-Br | 4-Cl | +++ | +++ | +++ | +++ | + | +++ |
| 4-Br | 2,4-$(Cl)_2$ | +++ | + | +++ | +++ | + | +++ |
| 2,4-$(Cl)_2$ | H | ++ | 0 | ++ | ++ | 0 | ++ |
| 4-$OCH_3$ | 4-Cl | ++ | + | ++ | + | + | ++ |
| H | 2,4-$(Cl)_2$ | ++ | ++ | +++ | + | + | ++ |
| 2,4-$(Cl)_2$ | 4-Cl | +++ | ++ | +++ | ++ | + | ++ |
| H | 4-Cl | +++ | + | +++ | + | + | ++ |
| 4-Cl | 2-Cl | +++ | ++ | +++ | ++ | + | ++ |
| 2-Cl | 2,4-$(Cl)_2$ | +++ | ++ | +++ | ++ | + | +++ |
| 4-Br | 2-Cl | +++ | + | ++ | +++ | + | ++ |
| 2-Cl | 4-Cl | +++ | + | +++ | +++ | + | +++ |
| 2,4-$(Cl)_2$ | 2,4-$(Cl)_2$ | +++ | ++ | +++ | +++ | + | +++ |
| 4-Br | H | ++ | + | +++ | ++ | + | +++ |
| H | 4-Br | +++ | 0 | +++ | +++ | 0 | +++ |
| 4-$CH_3$ | 2,4-$(Cl)_2$ | +++ | +++ | +++ | +++ | ++ | +++ |
| 4-Br | 4-Br | +++ | ++ | +++ | +++ | + | +++ |
| 2,4-$(Cl)_2$ | 2-Cl | +++ | +++ | +++ | +++ | ++ | +++ |
| 4-$CH_3$ | 4-Cl | +++ | ++ | +++ | +++ | + | +++ |
| 2,4-$(Cl)_2$ | 4-Br | +++ | ++ | +++ | ++ | + | ++ |
| 4-Cl | 4-Br | +++ | ++ | +++ | +++ | ++ | +++ |
| 4-$CH_3$ | 4-Br | +++ | ++ | +++ | +++ | + | +++ |
| 3-Cl | 2,4-$(Cl)_2$ | ++ | + | +++ | ++ | + | +++ |
| 2-Cl | 4-Br | ++ | ++ | ++ | ++ | + | ++ |
| 4-$CH_3$ | 2-Cl | +++ | + | +++ | ++ | + | +++ |
| 4-Cl | 4-$CH_3$ | +++ | + | +++ | ++ | + | +++ |
| 4-Br | 4-$CH_3$ | +++ | ++ | ++ | ++ | + | ++ |
| 4-Cl | 4-F | + | 0 | ++ | + | 0 | ++ |
| 4-Br | 4-F | ++ | + | +++ | ++ | + | +++ |

Table C2

BACTERIOSTATIC AND BACTERIOCIDAL ACTIVITY

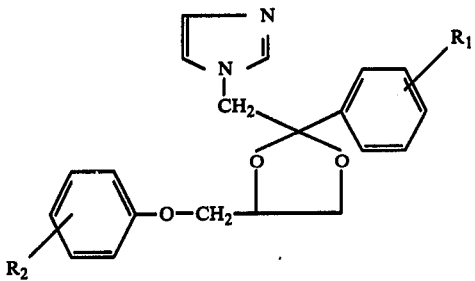

| $R_1$ | $R_2$ | Isomer | bacteriostatic activity | | | bacteriocidal activity | | |
|---|---|---|---|---|---|---|---|---|
| | | | E. ins. | Staph. | Strept. | E. ins. | Staph. | Strept. |
| 4-Cl | 2-$CH_3$,4-Cl | cis | ++++ | 0 | +++ | ++++ | 0 | +++ |
| 4-Cl | 4-$CH_3$ | trans | +++ | ++ | +++ | +++ | + | +++ |
| 4-Cl | 2-$CH_3$,4-Cl | trans | ++++ | ++ | ++++ | ++++ | ++ | +++ |
| 4-Cl | 4-$CH_3$ | cis | +++ | ++ | +++ | +++ | + | +++ |
| 4-Cl | 4-Cl | A | ++++ | + | +++ | ++++ | + | +++ |
| 4-Cl | 4-Cl | B | ++++ | ++ | +++ | ++++ | + | +++ |
| 4-Cl | 2,4-$(Cl)_2$ | A | 0 | 0 | ++ | 0 | 0 | ++ |
| 4-Cl | 4-F | cis | +++ | 0 | +++ | +++ | 0 | +++ |
| 4-Cl | 2-$CH_3$ | A | ++++ | ++ | ++++ | ++++ | + | ++++ |
| 4-Cl | 2-Cl | A | +++ | 0 | +++ | +++ | 0 | +++ |
| 4-Cl | 2-$CH_3$ | B | ++++ | ++ | +++ | +++ | + | +++ |
| 4-Cl | 2,4-$(Cl)_2$ | B | ++++ | ++ | ++++ | ++++ | ++ | ++++ |
| 4-Cl | 4-$OCH_3$ | A | +++ | 0 | +++ | ++ | 0 | +++ |
| 4-Cl | 4-F | trans | ++ | + | ++ | + | + | ++ |
| 4-Cl | 4-$OCH_3$ | B | ++ | + | ++ | + | + | ++ |
| 4-Cl | 2,6-$(Cl)_2$ | A | +++ | 0 | ++++ | ++ | 0 | ++++ |
| 4-Cl | 2-Cl | B | +++ | + | ++ | +++ | + | ++ |
| 4-Cl | 2,6-$(Cl)_2$ | B | +++ | ++ | +++ | +++ | + | +++ |
| 2,4-$(Cl)_2$ | 4-$CH_3$ | B | ++ | ++ | ++ | ++ | + | ++ |
| 2,4-$(Cl)_2$ | 4-F | A | ++ | ++ | ++ | ++ | 0 | ++ |
| 2,4-$(Cl)_2$ | 2-$CH_3$ | A | +++ | + | +++ | +++ | + | +++ |
| 2,4-$(Cl)_2$ | 4-$CH_3$ | A | +++ | ++ | +++ | +++ | + | +++ |
| 2,4-$(Cl)_2$ | 4-$OCH_3$ | A | ++ | + | ++ | ++ | + | ++ |
| 2,4-$(Cl)_2$ | 4-Cl | cis | ++ | + | ++ | ++ | + | ++ |
| 2,4-$(Cl)_2$ | 2-$CH_3$ | B | +++ | + | +++ | +++ | + | +++ |
| 2,4-$(Cl)_2$ | 2,4-$(Cl)_2$ | A | +++ | 0 | +++ | +++ | 0 | +++ |
| 2,4-$(Cl)_2$ | 4-Cl | trans | +++ | ++ | +++ | +++ | ++ | +++ |
| 2,4-$(Cl)_2$ | 4-Br | A | +++ | + | +++ | +++ | + | +++ |
| 2,4-$(Cl)_2$ | 2,4-$(Cl)_2$ | B | +++ | ++ | +++ | ++ | + | +++ |
| 2,4-$(Cl)_2$ | H | A | +++ | + | +++ | +++ | + | +++ |
| 2,4-$(Cl)_2$ | 3,4-$(Cl)_2$ | A | +++ | ++ | +++ | +++ | + | +++ |
| 2,4-$(Cl)_2$ | 3-Cl | A | +++ | ++ | +++ | +++ | ++ | +++ |
| 2,4-$(Cl)_2$ | 2-Cl | A | +++ | ++ | +++ | +++ | + | +++ |
| 2,4-$(Cl)_2$ | 2-$CH_3$,4-Cl | A + B | +++ | ++ | +++ | ++ | + | +++ |
| 2,4-$(Cl)_2$ | 2-Cl | B | +++ | + | +++ | ++ | + | +++ |
| 2,4-$(Cl)_2$ | 2,6-$(Cl)_2$ | A | +++ | ++ | +++ | ++ | + | ++ |
| 2,4-$(Cl)_2$ | 3,5-$(CH_3)_2$,4-Cl | A | +++ | 0 | +++ | +++ | 0 | +++ |
| 2,4-$(Cl)_2$ | 2,4-$(Br)_2$ | A | +++ | 0 | +++ | +++ | 0 | +++ |
| 2,4-$(Cl)_2$ | 4-CN | A | +++ | + | ++ | 0 | 0 | ++ |
| 2,4-$(Cl)_2$ | 2-Br | cis | +++ | + | +++ | +++ | + | +++ |
| 2,4-$(Cl)_2$ | 2-$OCH_3$ | A | +++ | + | +++ | +++ | + | ++ |
| 2,4-$(Cl)_2$ | 2-Br | trans | +++ | ++ | ++ | ++ | + | ++ |
| 2,4-$(Cl)_2$ | 2,4,6-$(Cl)_3$ | A | +++ | 0 | +++ | ++ | 0 | ++ |
| 2,4-$(Cl)_2$ | 2,5-$(CH_3)_2$ | A | +++ | ++ | +++ | +++ | + | +++ |
| 2,4-$(Cl)_2$ | 2,5-$(CH_3)_2$ | B | +++ | ++ | +++ | +++ | + | +++ |
| 2,4-$(Cl)_2$ | 2-Cl,4-tert.but. | A | +++ | ++ | +++ | ++ | 0 | ++ |
| 2,4-$(Cl)_2$ | 2,4,5-$(Cl)_3$ | A | ++++ | 0 | ++ | +++ | 0 | ++ |
| 2,4-$(Cl)_2$ | 2-Cl,4-tert.but. | B | ++++ | ++ | ++++ | +++ | + | +++ |
| 2,4-$(Cl)_2$ | 2,4,5-$(Cl)_3$ | B | +++ | + | +++ | ++ | + | ++ |
| 2,4-$(Cl)_2$ | 2,5-$(Br)_2$,4-$CH_3$ | A | +++ | + | +++ | ++ | + | ++ |
| 2,4-$(Cl)_2$ | 2-F | A | +++ | + | ++++ | ++ | + | +++ |
| 4-$CH_3$ | 4-Br | A | +++ | ++ | ++++ | ++ | + | +++ |
| 4-Cl | 4-Br | A | ++++ | ++ | ++++ | +++ | + | +++ |
| 4-Br | 4-Br | A | ++++ | + | ++++ | +++ | + | +++ |
| 2,4-$(Cl)_2$ | 2-$OC_2H_5$ | A | ++++ | 0 | ++++ | +++ | 0 | +++ |
| 2-Cl | 4-Br | A + B | ++++ | ++ | ++++ | +++ | + | +++ |
| 2-Cl | 4-Br | B | +++ | ++ | ++++ | ++ | + | +++ |
| H | 4-Br | A | +++ | ++ | ++++ | + | 0 | +++ |
| 2-Br | 4-Br | A | ++++ | +++ | ++++ | +++ | ++ | +++ |
| 2-Br | 4-Br | B | ++++ | ++ | ++++ | +++ | + | ++++ |
| 2,4-$(Cl)_2$ | 4-$C_6H_5$ | A + B | ++++ | 0 | ++ | +++ | 0 | ++ |
| 2,4-$(Cl)_2$ | 4-$C_6H_5$ | B | 0 | 0 | ++++ | 0 | 0 | +++ |
| 2,4-$(Cl)_2$ | 2,6-$(CH_3)_2$ | A | ++++ | ++ | ++++ | +++ | ++ | +++ |
| 2,4-$(Cl)_2$ | 4-Br | B | +++ | +++ | +++ | ++ | + | ++ |
| 2,4-$(Cl)_2$ | 2,6-$(CH_3)_2$ | A + B | +++ | ++ | +++ | ++ | + | +++ |
| 2,4-$(Cl)_2$ | 3,5-$(CH_3)_2$ | A | +++ | ++ | +++ | ++ | + | ++ |
| 2,4-$(Cl)_2$ | 4-$iC_3H_7$ | A + B | ++ | ++ | +++ | ++ | + | ++ |
| 2,4-$(Cl)_2$ | 2-Cl,6-$CH_3$ | A | ++ | ++ | ++ | ++ | + | ++ |
| 2,4-$(Cl)_2$ | 4-tert.but. | A | +++ | ++ | ++ | ++ | + | ++ |
| 2,4-$(Cl)_2$ | 3,5-$(Cl)_2$ | A | ++ | +++ | ++++ | ++ | ++ | +++ |
| 2,4-$(Cl)_2$ | 3-$CH_3$, 4-Cl | A | +++ | ++ | ++ | ++ | ++ | + |

Table C3
BACTERIOSTATIC AND BACTERIOCIDAL ACTIVITY

| $R_1$ | $R_2$ | Isomer | Bacteriostatic activity | | | Bacteriocidal activity | | |
|---|---|---|---|---|---|---|---|---|
| | | | E. ins. | Staph. | Strept. | E. ins. | Staph. | Strept. |
| 2,4-(Cl)$_2$ | 4-Br | A + B | +++ | ++ | ++++ | ++ | + | +++ |
| 2,4-(Cl)$_2$ | H | A + B | ++++ | ++ | ++++ | +++ | + | +++ |

Table C4

| $R_1$ | $R_2$ | Isomer | Bacteriostatic activity | | | bacteriocidal activity | | |
|---|---|---|---|---|---|---|---|---|
| | | | E. ins. | Staph. | Strept. | E. ins. | Staph. | Strept. |
| 2,4-(Cl)$_2$ | 2-Cl | | ++++ | +++ | ++++ | +++ | ++ | +++ |
| 2,4-(Cl)$_2$ | 2,4-(Cl)$_2$ | | ++++ | +++ | ++++ | +++ | ++ | +++ |
| 2,4-(Cl)$_2$ | 2,6-(Cl)$_2$ | A + B | ++++ | +++ | ++++ | +++ | ++ | +++ |
| 2,4-(Cl)$_2$ | 4-OCH$_3$ | A + B | ++++ | + | +++ | +++ | + | ++ |
| 2,4-(Cl)$_2$ | 4-Cl | | ++++ | ++ | ++++ | +++ | + | +++ |
| 2,4-(Cl)$_2$ | H | | ++++ | ++ | +++ | +++ | 0 | ++ |

Table C5
BACTERIOSTATIC AND BACTERIOCIDAL ACTIVITY

| Ar | R | isomer | Bacteriostatic activity | | | Bacteriocidal activity | | |
|---|---|---|---|---|---|---|---|---|
| | | | E. ins. | Staph. | Strept. | E. ins. | Staph. | Strept. |
| 2,4-(Cl)$_2$—C$_6$H$_3$ | C$_2$H$_5$ | A + B | +++ | ++ | +++ | ++ | 0 | +++ |
| 2-Cl—C$_6$H$_4$ | C$_2$H$_5$ | A + B | ++ | + | o | ++ | + | o |
| 2-CH$_3$—C$_6$H$_4$ | C$_2$H$_5$ | A + B | ++ | o | ++ | o | o | o |
| 4-CH$_3$—C$_6$H$_4$ | C$_2$H$_5$ | A + B | ++ | + | ++ | ++ | o | ++ |
| 2,3,4-(Cl)$_3$—C$_6$H$_2$ | C$_2$H$_5$ | A + B | +++ | ++ | +++ | +++ | + | +++ |
| 2-Br—C$_6$H$_4$ | C$_2$H$_5$ | A + B | ++ | + | ++ | ++ | o | ++ |
| 2,3-(Cl)$_2$—C$_6$H$_3$ | C$_2$H$_5$ | A + B | ++ | + | ++ | ++ | o | ++ |
| 2-Cl,4-F—C$_6$H$_3$ | C$_2$H$_5$ | A + B | ++ | o | ++ | ++ | o | ++ |
| 4-Br—C$_6$H$_4$ | C$_2$H$_5$ | A + B | ++ | o | + | ++ | o | + |
| 3-Cl—C$_6$H$_4$ | C$_2$H$_5$ | A + B | ++ | o | ++ | ++ | o | ++ |
| 2-Cl,4-Br—C$_5$H$_3$ | C$_2$H$_5$ | A + B | +++ | + | ++ | +++ | + | ++ |
| 2,4-(Br)$_2$—C$_6$H$_3$ | C$_2$H$_5$ | A + B | +++ | + | ++ | +++ | + | ++ |
| 4-OCH$_3$—C$_6$H$_4$ | C$_2$H$_5$ | A + B | + | o | + | + | o | + |
| 2-thienyl | C$_2$H$_2$ | A + B | + | o | + | o | o | + |
| 2-CH$_3$,4-Cl—C$_6$H$_3$ | C$_2$H$_5$ | A + B | +++ | + | + | +++ | + | + |
| 2-Cl, 4-OCH$_3$ | C$_2$H$_5$ | A + B | ++ | + | ++ | + | o | + |
| 2-naphthyl | C$_2$H$_5$ | A + B | +++ | + | ++ | + | o | + |
| 5-Cl-2-thienyl | C$_2$H$_5$ | A + B | ++ | + | ++ | o | o | o |
| 2-OCH$_3$,4-Cl—C$_6$H$_3$ | C$_2$H$_5$ | A + B | + | o | + | + | o | + |
| 2,4-(Cl)$_2$—C$_6$H$_3$ | nC$_3$H$_7$ | A + B | +++ | ++ | +++ | +++ | + | +++ |
| 2,4-(Cl)$_2$—C$_6$H$_3$ | nC$_4$H$_9$ | A + B | +++ | +++ | +++ | +++ | +++ | +++ |

Table C5-continued
BACTERIOSTATIC AND BACTERIOCIDAL ACTIVITY

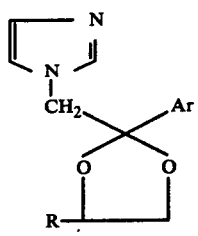

| Ar | R | isomer | Bacteriostatic activity | | | Bacteriocidal activity | | |
|---|---|---|---|---|---|---|---|---|
| | | | E. ins. | Staph. | Strept. | E. ins. | Staph. | Strept. |
| 2,4-(Cl)$_2$—C$_6$H$_3$ | nC$_5$H$_{11}$ | A + B | +++ | ++ | +++ | +++ | ++ | +++ |
| 2,4-(Cl)$_2$—C$_6$H$_3$ | nC$_6$H$_{13}$ | A + B | +++ | +++ | +++ | +++ | ++ | +++ |
| 2,4-(Cl)$_2$—C$_6$H$_3$ | nC$_7$H$_{15}$ | A + B | +++ | +++ | +++ | +++ | ++ | +++ |
| 2,4-(Cl)$_2$—C$_6$H$_3$ | nC$_8$H$_{17}$ | A + B | +++ | ++ | +++ | +++ | ++ | +++ |
| 2,4-(Cl)$_2$—C$_6$H$_3$ | CH$_2$Cl | A + B | + | o | + | + | o | + |
| 2,4-(Cl)$_2$—C$_6$H$_3$ | CH$_2$OH | trans | + | o | + | o | o | + |
| 2,4-(Cl)$_2$—C$_6$H$_3$ | CH$_2$OH | A + B | ++ | o | + | ++ | o | + |
| 2,4-(Cl)$_2$—C$_6$H$_3$ | CH$_2$OH | cis | + | o | o | + | o | o |
| 3,4,5-(Cl)$_3$—C$_6$H$_2$ | C$_2$H$_5$ | A + B | +++ | ++ | +++ | ++ | + | ++ |

Table C6
BACTERIOSTATIC AND BACTERIOCIDAL ACTIVITY

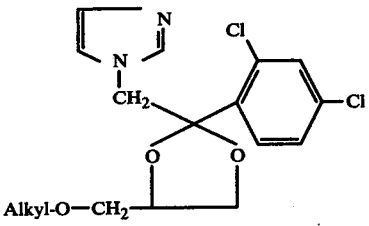

| Alkyl | isomer | Bacteriostatic activity | | | Bacteriocidal activity | | |
|---|---|---|---|---|---|---|---|
| | | E. ins. | Staph. | Strept. | E. ins. | Staph. | Strept. |
| CH$_3$ | cis | + | o | o | + | o | o |
| C$_2$H$_5$ | trans | ++ | + | ++ | + | o | + |
| nC$_3$H$_7$ | cis | ++ | + | + | ++ | o | o |
| nC$_4$H$_9$ | A + B | +++ | ++ | +++ | + | o | + |
| nC$_5$H$_{11}$ | cis | +++ | +++ | +++ | +++ | o | ++ |
| nC$_6$H$_{13}$ | cis | +++ | ++ | ++ | ++ | + | ++ |
| nC$_7$H$_{15}$ | cis | +++ | +++ | +++ | +++ | + | ++ |
| nC$_8$H$_{17}$ | cis | +++ | ++ | +++ | ++ | + | +++ |

Table C7

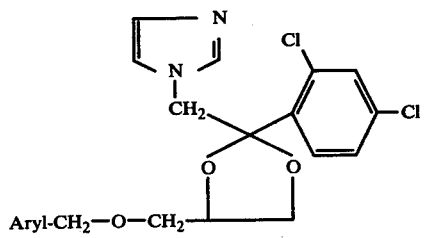

| Aryl | isomer | Bacteriostatic activity | | | Bacteriocidal activity | | |
|---|---|---|---|---|---|---|---|
| | | E. ins. | Staph. | Strept. | E. ins. | Staph. | Strept. |
| 4-(C$_6$H$_5$)—C$_6$H$_4$ | cis | +++ | +++ | +++ | +++ | + | +++ |
| 4-(C$_6$H$_5$)—C$_6$H$_4$ | trans | +++ | ++ | +++ | +++ | ++ | +++ |
| 4-Br—C$_6$H$_4$ | cis | +++ | ++ | +++ | +++ | + | +++ |
| 2,4-(Cl)$_2$—c$_6$H$_3$ | cis | +++ | +++ | +++ | ++ | + | ++ |
| 2,4-(Cl)$_2$—C$_6$H$_3$ | trans | +++ | ++ | +++ | +++ | + | ++ |

Table C8
BACTERIOSTATIC AND BACTERIOCIDAL ACTIVITY

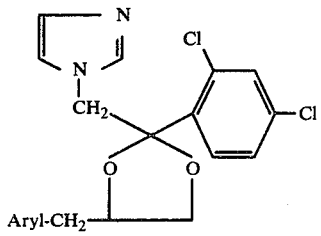

| Aryl | Bacteriostatic activity | | | Bacteriocidal activity | | |
|---|---|---|---|---|---|---|
| | E. ins. | Staph. | Strept. | E. ins. | Staph. | Strept. |
| $C_6H_5$ | +++ | ++ | ++ | +++ | + | ++ |
| 4-Cl—$C_6H_4$ | +++ | ++ | ++ | +++ | ++ | ++ |
| 4-F—$C_6H_4$ | +++ | ++ | ++ | ++ | + | ++ |
| 4-$CH_3$—$C_6H_4$ | +++ | ++ | +++ | +++ | ++ | +++ |
| 4-Br—$C_6H_4$ | +++ | ++ | +++ | +++ | ++ | +++ |
| 4-$OCH_3$—$C_6H_4$ | +++ | + | +++ | +++ | + | +++ |
| 4-($C_6H_5$)—$C_6H_4$ | +++ | ++ | +++ | ++ | + | ++ |

In view of the aforementioned antifungal and antibacterial activities this invention provides valuable compositions comprising the subject 1,3-dioxolan-2-ylmethyl imidazoles (I) or the acid addition salts thereof as the active ingredient in a solvent or a solid, semi-solid or liquid diluent or carrier, and, in addition, it provides an effective method of combatting fungus or bacterial growth by use of an effective anti-fungal or anti-bacterial amount of such ketals (I) or salts thereof. The subject compounds can be used in suitable solvents or diluents, in the form of emulsions, suspensions, dispersions or ointments, on suitable solid or semisolid carrier substances, in ordinary or synthetic soaps, detergents or dispersion media, if desired, together with other compounds having arachnicidal, insecticidal, ovicidal, fungicidal and/or bactericidal effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr and boric acid; powdered cork, sawdust, and other fine pulverous materials of vegetable origin are also suitable carrier substances.

The active ingredient is mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, such pulverous preparations can also be made readily wettable with water, so that suspensions are obtained.

Inert solvents used for the production of liquid preparations should preferably not be readily inflammable and should be as far as possible odorless and as far as possible non-toxic to warm-blooded animals or plants in the relevant surroundings. Solvents suitable for this purpose are high-boiling oils, for example, of vegetable origin, and lower-boiling solvents with a flash point of at least 30° C., such as, for example, polyethylene glycols, isopropanol, dimethylsulfoxide, hydrogenated naphthalenes and alkylated naphthalenes. It is, of cours, also possible to use mixtures of solvents. Solutions can be prepared in the usual way, if necessary, with assistance of solution promotors. Other liquid forms which can be used consist of emulsions or suspensions of the active compound in water or suitable inert solvents, or also concentrates for preparing such emulsions, which can be directly adjusted to the required concentration. For this purpose, the active ingredient is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the active component can be incorporated, if necessary, with the aid of solution promotors and/or emulsifiers. Vaseline and other cream bases are examples of semi-solid carrier substances.

Furthermore, it is possible for the active component to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combatting fungi and bacteria, e.g., in closed chambers and storage rooms, and for application to vegetation for eradicating or for preventing infections by fungi or bacteria.

The subject compounds and compositions thereof can be applied by conventional methods. For example, a fungus or bacterial growth or a material to be treated or to be protected against attack by fungus or bacterium can be treated with the subject compounds and the compositions thereof by dusting, sprinkling, spraying, brushing, dipping, smearing, impregnating or other suitable means.

When the subject compounds are employed in combination with suitable carriers, e.g., in solution, suspension, dust, powder, ointment, emulsion, and the like forms, a high activity over a very high range of dilution is observed. For example, concentrations of the active ingredient ranging from 0.1–10 percent by weight, based on the weight of composition employed, have been found effective in combatting fungi or bacteria. Of course, higher concentrations may also be employed as warranted by the particular situation.

The following examples are intended to illustrate, but not to limit, the scope of the present invention. Unless otherwise stated, all parts are by weight.

A. NOVEL INTERMEDIATES

EXAMPLE I

A mixture of 11.7 parts of 2-bromo-4'-chloroacetophenone, 9 parts of 1-(p-chlorophenyl)-1,2-ethanediol, 0.5 parts of p-toluenesulfonic acid and 80 parts of benzene is stirred and refluxed for 2 days with water-separator. The reaction mixture is cooled and washed successively twice with a sodium hydrogen carbonate solution and once with water. The organic phase is dried and evaporated. The residue is triturated in petroleum ether and cooled on ice. The precipitated product is filtered off, crystallized from methanol, stirred in acetonitrile while cooling on ice, filtered off again and washed once more with acetonitrile, yielding 2-(bromomethyl)-2,4-bis(p-chlorophenyl)-1,3-dioxolane.

EXAMPLE II

A mixture of 11.6 parts of 2-bromo-4'-chloroacetophenone, 8.4 parts of α-(hydroxymethyl)-benzylalcohol, 0.1 parts of p-toluene sulfonic acid, 210 parts of benzene and 40 parts of ethanol is stirred and refluxed for 24 hours. The reaction mixture is evaporated and the residue is triturated in methanol. The product is filtered off and crystallized from methanol, yielding 2-(bromomethyl)-2-(p-chlorophenyl)-4-phenyl-1,3-dioxolane; mp. 60° C.

EXAMPLE III

A mixture of 11.6 parts of 2-bromo-4'-chloroacetophenone, 12.4 parts of 1-(2,4-dichlorophenyl)-1,2-ethanediol, 0.1 parts of p-toluenesulfonic acid, 80 parts of n-butanol and 160 parts of benzene is stirred and refluxed for 24 hours with water-separator. The solvent is removed in vacuo and the residue is triturated in methanol. The precipitated product is filtered off and crystallized from petroleum ether, yielding 2-(bromomethyl)-2-(p-chlorophenyl)-4-(2,4-dichlorophenyl)-1,3-dioxolane; m.p. 82.7° C.

EXAMPLE IV

Following the procedure of Example III and using equivalent amounts of the appropriate starting materials, the following dioxolanes are prepared:

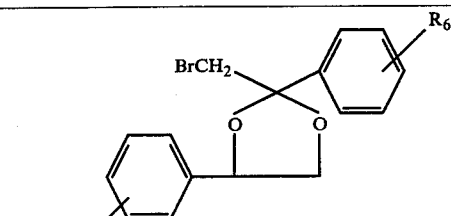

| $R_6$ | $R_7$ | Melting Point |
|---|---|---|
| 4-Br | 4-Cl | 101.3° |
| 4-Br | 2,4-(Cl)$_2$ | 99.9° |
| 4-OCH$_3$ | 4-Cl | 115.6° |
| — | 4-Cl | 63.9° |
| 4-CH$_3$ | 2,4-(Cl)$_2$ | 89.9° |
| 4-Br | 4-Br | 96.8° |
| 4-CH$_3$ | 4-Cl | 122° |
| 4-CH$_3$ | 4-Br | 118.6° |

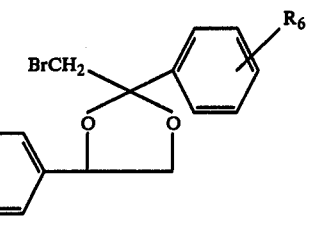

| $R_6$ | $R_7$ | Melting Point |
|---|---|---|
| 4-CH$_3$ | 2-Cl | |

EXAMPLE V

A mixture of 13.4 parts of 2-bromo-2',4'-dichloroacetophenone, 8.4 parts of α-(hydroxymethyl)-benzyl alcohol, 1.15 parts of p-toluenesulfonic acid, 160 parts of benzene and 140 parts of n-butanol is stirred and refluxed for 48 hours with a water-separator. The solvent is removed in vacuo. The residue is purified by column-chromatography over silica gel, using chloroform as eluent. The pure fractions are collected and the eluent is evaporated, yielding 2-(bromomethyl)-2-(2,4-dichlorophenyl)-4-phenyl-1,3-dioxolane as residue.

EXAMPLE VI

Following the procedure of Example V but substituting for the α-(hydroxymethyl)benzyl alcohol used therein equivalent amounts of 2,4-dichloro-α-(hydroxymethyl)benzyl alcohol and p-chloro-α-(hydroxymethyl)benzyl alcohol, and using the appropriately substituted 2-bromoacetophenone, there are prepared (2-(bromomethyl)-4-(2,4-dichlorophenyl)-2-phenyl-1,3-dioxolane and 2-(bromomethyl)-4-(p-chlorophenyl)-2-(2,4-dichlorophenyl)-1,3-dioxolane.

EXAMPLE VII

A mixture of 11.5 parts of 2-bromo-p-chloroacetophenone, 10.4 parts of o-chloro-α-(hydroxymethyl)benzylalcohol, 0.2 parts of p-toluenesulfonic acid, 180 parts of benzene and 80 parts of butanol is stirred and refluxed overnight with water-separator. The solvent is removed in vacuo and the residue is dissolved in chloroform. The chloroform solution is stirred with silica gel for 30 minutes. The silica gel is filtered off and the solvent is removed in vacuo, yielding 2-(bromomethyl)-4-(o-chlorophenyl)-2-(p-chlorophenyl)-1,3-dioxolane as a residue.

EXAMPLE VIII

Following the procedure of Example VII and using equivalent amounts of the appropriate starting materials, the following dioxolanes are prepared:

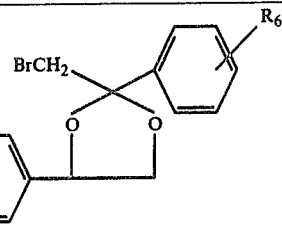

| R$_6$ | R$_7$ | Melting Point |
|---|---|---|
| 2-Cl | 2,4-(Cl)$_2$ | |
| 4-Br | 2-Cl | |
| 2-Cl | 4-Cl | |
| 2,4-(Cl)$_2$ | 2,4-(Cl)$_2$ | |
| 4-Br | — | 70° |
| — | 4-Br | 71.3° |
| 2,4-(Cl)$_2$ | 2-Cl | |
| 2,4-(Cl)$_2$ | 4-Br | |
| 4-Cl | 4-Br | 80.5° |
| 3-Cl | 2,4-(Cl)$_2$ | |
| 2-Cl | 4-Br | |
| 4-Cl | 4-CH$_3$ | |
| 4-Br | 4-CH$_3$ | |
| 4-Cl | 4-F | |
| 4-Br | 4-F | |

EXAMPLE IX

A mixture of 11.7 parts of 2-bromo-4'-chloroacetophenone, 11.9 parts of 1-(4-chloro-o-tolyloxy)-2,3-propanediol, 2.5 parts of p-toluenesulfonic acid and 240 parts of benzene is stirred and refluxed for 24 hours in a four-necked round-bottomed flask equipped with a watertrap. The benzene solution is washed successively with a diluted sodium hydroxide solution and with water. The solvent is removed in vacuo. The residue is crystallized from methanol and the less pure fraction is recrystallized from diisopropylether, yielding A-2-(bromomethyl)-2-(p-chlorophenyl)-4-(4-chloro-o-tolyloxymethyl)-1,3-dioxolane; m.p. 102.5° C. The methanol filtrate is evaporated in vacuo, yielding B-2-(bromomethyl)-2-(p-chlorophenyl)-4-(4-chloro-o-tolyloxymethyl)-1,3-dioxolane as a residue.

EXAMPLE X

Following the procedure of Example IX and using equivalent amounts of the appropriate starting materials, the following dioxolanes are prepared:

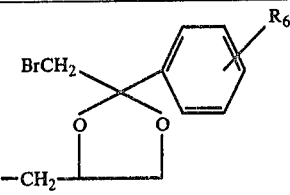

| Isomer | R$_6$ | R$_7$ | Melting Point |
|---|---|---|---|
| A | 4-Cl | 4-CH$_3$ | |
| B | 4-Cl | 4-CH$_3$ | |
| A | 4-Cl | 2,4-Cl | |
| B | 4-Cl | 2,4-Cl | |
| A | 4-Cl | 4-F | 102° |
| B | 4-Cl | 4-F | |
| A | 4-Cl | 2-CH$_3$ | 82.2 - 85° |
| B | 4-Cl | 2-CH$_3$ | |
| A | 4-Cl | 2-Cl | 85 - 88.6° |
| B | 4-Cl | 2-Cl | |
| A | 4-Cl | 4-OCH$_3$ | |
| B | 4-Cl | 4-OCH$_3$ | |
| A | 2,4-(Cl)$_2$ | 4-F | |
| A | 2,4-(Cl)$_2$ | 4-OCH$_3$ | |

EXAMPLE XI

A mixture of 11.7 parts of 2-bromo-4'-chloroacetophenone, 12.2 parts of 1-(p-chlorophenoxy)-2,3-propanediol, 3 parts of p-toluenesulfonic acid and 240 parts of benzene is stirred and refluxed for 20 hours in a four-necked round-bottom flask equipped with a watertrap. The benzene solution is washed successively with a diluted sodium hydroxide solution and with water. The solvent is removed in vacuo. The residue is triturated in methanol. The precipitated product is filtered off (methanol filtrate is set aside) and crystallized from toluene, yielding A-2-(bromomethyl)-4-(p-chlorophenoxymethyl)-2-(p-chlorophenyl)-1,3-dioxolane; m.p. 165° C.

The methanol filtrate is evaporated in vacuo. The residue is chromatographed over silica gel with chloroform as eluent, yielding B-2-(bromomethyl)-4-(p-chlorophenoxymethyl)-2-(p-chlorophenyl)-1,3-dioxolane as a residue.

EXAMPLE XII

A mixture of 13.4 parts of 2-bromo-2',4'-dichloroacetophenone, 11.2 parts of 1-(p-tolyloxy)-2,3-propanediol, 3 parts of p-toluenesulfonic acid and 240 parts of benzene is stirred and refluxed in a four-necked round-bottomed flask, equipped with a water-trap. When no more water is evolved (20 hours), the benzene solution is washed successively with diluted sodium hydroxide solution and twice with water. The solution is dried and the solvent is removed in vacuo. The residue is triturated in methanol. The precipitated product is filtered off (filtrate is set aside) and crystallized from butanol, yielding A-2-(bromomethyl)-2-(2,4-dichlorophenyl)-4-(p-tolyloxymethyl)-1,3-dioxolane.

The methanol filtrate (see above) is evaporated in vacuo and residue is dissolved in chloroform. This solution is stirred with silica gel for 5 hours. The mixture is filtered and the filtrate is evaporated in vacuo, yielding B-2-(bromomethyl)-2-(2,4-dichlorophenyl)-4-(p-tolyloxymethyl)-1,3-dioxolane.

EXAMPLE XIII

Following the procedure of Example XII and using equivalent amounts of the appropriate starting materials, the following dioxolanes are prepared:

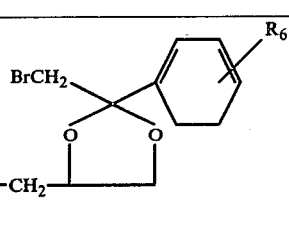

| Isomer | R$_6$ | R$_7$ | Melting Point |
| --- | --- | --- | --- |
| A | 2,4-(Cl)$_2$ | 4-Cl | |
| B | 2,4-(Cl)$_2$ | 4-Cl | |
| A | 2,4-(Cl)$_2$ | 2,4-(Cl)$_2$ | |
| B | 2,4-(Cl)$_2$ | 2,4-(Cl)$_2$ | |
| A | 2,4-(Cl)$_2$ | — | 97.6° |
| A | 2,4-(Cl)$_2$ | 3,4-(Cl)$_2$ | |
| A | 2,4-(Cl)$_2$ | 3-Cl | |
| A | 2,4-(Cl)$_2$ | 4-Cl,3,5-(CH$_3$)$_2$ | 115.8° |
| A | 2,4-(Cl)$_2$ | 2,4-(Br)$_2$ | |
| A | 2,4-(Cl)$_2$ | 4-CN | |
| A | 2,4-(Cl)$_2$ | 2-OCH$_3$ | |
| A + B | 2,4-(Cl)$_2$ | 4-C$_6$H$_5$ | |
| A + B | 2,4-(Cl)$_2$ | 4-iC$_3$H$_7$ | 90° |
| A | 2,4-(Cl)$_2$ | 4-Cl,3-CH$_3$ | |
| A | 2,4-(Cl)$_2$ | 3,5-(Cl)$_2$ | |
| A | 2,4-(Cl)$_2$ | 4-tert.butyl | |

EXAMPLE XIV

A mixture of 11.7 parts of 2-bromo-4'-chloroacetophenone, 14.2 parts of 1-(2,6-dichlorophenoxy)-2,3-propanediol, and 3 parts of p-toluenesulfonic acid and 240 parts of benzene is stirred and refluxed for 20 hours in a four-necked round-bottomed flask equipped with watertrap. The benzene-solution is washed successively with a diluted sodium hydroxide solution and with water. The solvent is removed in vacuo, yielding A + B-2-(bromomethyl)-2-(p-chlorophenyl)-4-(2,6-dichlorophenoxymethyl)-1,3-dioxolane as a residue.

EXAMPLE XV

A mixture of 13.4 parts of 2-bromo-2',4'-dichloroacetophenone, 11.2 parts of 3-(o-tolyloxy)-1,2-propanediol, 3 parts of p-toluenesulfonic acid and 240 parts of benzene is stirred and refluxed in a four-necked round bottomed flask equipped with a water-trap. After 20 hours, the theoretical amount of water is evolved and the reaction mixture is allowed to cool to room temperature. The mixture is washed successively with diluted sodium hydroxide solution and twice with water. The solvent is removed in vacuo and the residue is dissolved in chloroform. This solution is stirred with silica gel, filtered and the filtrate is evaporated in vacuo, yielding A + B-2-(bromomethyl)-2-(2,4-dichlorophenyl)-4-(o-tolyloxymethyl)-1,3-dioxolane.

EXAMPLE XVI

Following the procedure of Example XV but substituting for the 3-(o-tolyloxy)-1,2-propanediol used therein equivalent amounts of the appropriate starting material, the following dioxolanes are prepared: A + B 2-(bromomethyl)-4-(o-chlorophenoxymethyl)-2-(2,4-dichlorophenyl)-1,3-dioxolane; 2-(bromomethyl)-4-(2,6-dichlorophenoxymethyl-2-(2,4-dichlorophenyl)-1,3-dioxolane; A + B 2-(bromomethyl)-4-(o-bromophenoxymethyl)-2-(2,4-dichlorophenyl)-1,3-dioxolane; A + B 2-(bromomethyl)-4-(4-bromophenoxymethyl)-2-(2-bromophenyl)-1,3-dioxolane; A + B 2-(bromomethyl)-4-(2-chloro-6-methylphenoxymethyl)-2-(2,4-dichlorophenyl)-1,3-dioxolane; and A + B 2-(bromomethyl)-4-(2,3-dichlorophenoxymethyl)-2-(2,4-dichlorophenyl)-1,3-dioxolane.

EXAMPLE XVII

A mixture of 6 parts of 2-bromo-2', 4'-dichloroacetophenone, 6 parts of 3-(4-chloro-o-tolyloxy)-1,2-propanediol, 3 parts of p-toluenesulfonic acid, 80 parts of n-butanol and 180 parts of benzene is stirred and refluxed for 24 hours with water-separator. The solvent is removed in vacuo and the residue is triturated in methanol. The produce is filtered off and crystallized from petroleumether, yielding A + B 2-(bromomethyl)-4-(4-chloro-2-tolyloxymethyl)-2-(2,4-dichlorophenyl)-1,3-dioxolane.

EXAMPLE XVIII

A mixture of 13.6 parts of 2-bromo-1-(2,4-dichlorophenyl)-1-ethanone, 12 parts of 3-(2,5-dimethylphenoxy)-1,2-propanediol, 3 parts of 4-methylbenzenesulfonic acid, 80 parts of butanol and 180 parts of benzene is stirred and refluxed for 24 hours with water-separator. The reaction mixture is evaporated and the residue is dissolved in trichloromethane. The solution is stirred with silicagel for 30 minutes. The latter is filtered off and the filtrate is evaporated, yielding A + B 2-(bromomethyl)-2-(2,4-dichlorophenyl)-4-(2,5-dimethylphenoxymethyl)-1,3-dioxolane as a residue.

EXAMPLE XIX

Following the procedure of Example XVIII and using equivalent amounts of the appropriate starting materials, the following dioxolanes are prepared:

| Isomer | R$_6$ | R$_7$ |
| --- | --- | --- |
| A + B | 2,4-(Cl)$_2$ | 2,4,6-(Cl)$_3$ |
| A + B | 2,4-(Cl)$_2$ | 2-Cl,4-C(CH$_3$)$_3$ |
| A + B | 2,4-(Cl)$_2$ | 2,4,5-(Cl)$_3$ |
| A + B | 2,4-(Cl)$_2$ | 2,5-(Br)$_2$,4-CH$_3$ |
| A + B | 2,4-(Cl)$_2$ | 2-OC$_2$H$_5$ |
| A + B | 2-Cl | 4-Br |

EXAMPLE XX

A mixture of 13.6 parts of 2-bromo-2',4'-dichloroacetophenone, 18 parts of 3-(6-bromo-2-napthyloxy)-1,2-propanediol, 3 parts of p-toluenesulfonic acid, 80 parts of n-butanol and 180 parts of benzene is stirred and refluxed for 24 hours with water-separator. The reaction mixture is evaporated. The residue is dissolved in chloroform and the solution is stirred with silica gel for one hour. The latter is filtered off and the filtrate is evaporated. The residue is crystallized twice: first from diisopropylether and then from dibutylether, yielding A 2-(bromomethyl)-4-(6-bromo-2-naphthyloxymethyl)-2-(2,4-dichlorophenyl)-1,3-dioxolane.

EXAMPLE XXI

A mixture of 13.6 parts of 2-bromo-1-(2,4-dichlorophenyl)-1-ethanone, 13.1 parts of 3-(2-naphtalenyloxy)-1,2-propanediol, 3 parts of 4-methylbenzenesulfonic acid, 180 parts of benzene and 80 parts of butanol is stirred and refluxed for 12 hours with water-separator. The reaction mixture is evaporated and the residue is triturated in methanol. The product is filtered off and crystallized from 2-propanol, yielding A 2-(bromomethyl)-2-(2,4-dichlorophenyl)-4-[(2-naphthalenyloxy)methyl]-1,3-dioxo-lane; mp. 117.6° C.

EXAMPLE XXII

Following the procedure of Example XXI and using equivalent amounts of the appropriate starting materials, the following dioxolanes are prepared:

| Isomer | $R_6$ | $R_7$ | Melting Point |
|---|---|---|---|
| A | 2,4-(Cl)$_2$ | 2-F | 125.7° |
| A + B | 4-CH$_3$ | 4-Br | 121.1° |
| A + B | 4-Cl | 4-Br | 157.4° |
| A + B | 4-Br | 4-Br | 158.7° |
| A | 2,4-(Cl)$_2$ | 3-Br | 112.7° |
| A | 2,4-(Cl)$_2$ | 3,5-(CH$_3$)$_2$ | 118.7° |
| A + B | 2,4-(Cl)$_2$ | 4-CH$_2$—C$_6$H$_5$ | 106.1° |
| A + B | 4-OCH$_3$ | 4-Br | 117° |
| A | — | 4-Br | 85.6° |

EXAMPLE XXIII

A mixture of 13.6 parts of 2-bromo-1-(2,4-dichlorophenyl)-1-ethanone, 15.2 parts of 3-(4-chloro-1-naphthalenyloxy)-1,2-propanediol, 3 parts of 4-methylbenzenesulfonic acid, 80 parts of butanol and 180 parts of benzene is stirred and refluxed for 24 hours with water-separator. The reaction mixture is evaporated and the residue is triturated in 2-propanol. The product is filtered off and crystallized from butanol, yielding A + B 2-(bromomethyl)-4-(4-chloro-1-naphthalenyloxymethyl)-2-(2,4-dichlorophenyl)-1,3-dioxolane; mp. 122.7° C.

EXAMPLE XXIV

A mixture of 13.6 parts of 2-bromo-1-(2,4-dichlorophenyl)-1-ethanone, 15.8 parts of 3-(4-bromophenylthio)-1,2-propanediol, 3 parts of 4-methylbenzenesulfonic acid, 180 parts of butanol and 90 parts of benzene is stirred and refluxed for 12 hours with water-separator. The reaction mixture is evaporated and the residue is dissolved in trichloromethane. The solution is stirred with silica gel for 30 minutes. The latter is filtered off and the filtrate is evaporated, yielding A + B 2-(bromomethyl)-4-(4-bromophenylthiomethyl)-2-(2,4-dichlorophenyl)-1,3-dioxolane as a residue.

EXAMPLE XXV

A mixture of 13.6 parts of 2-bromo-1-(2,4-dichlorophenyl)-1-ethanone, 11.1 parts of 3-(phenylthio)-1,2-propanediol, 3 parts of 4-methylbenzenesulfonic acid, 80 parts of butanol and 180 parts of benzene is stirred and refluxed for 24 hours with water-separator. The reaction mixture is evaporated and the residue is dissolved in trichloromethane. The solution is stirred with silica gel for 30 minutes. The latter is filtered off and the filtrate is evaporated, yielding A + B 2-(bromomethyl)-2-(2,4-dichlorophenyl)-4-(phenylthiomethyl)-1,3-dioxolane as a residue.

EXAMPLE XXVI

A mixture of 222.5 parts of 2-bromo-1-(2,4-dichlorophenyl)-1-ethanone, 250 parts of 3-(4-bromophenoxy)-1,2-propanediol, 50 parts of 4-methylbenzenesulfonic acid and 3150 parts of benzene is stirred and refluxed in a four-necked, round-bottomed flask, equipped with a water-trap. After 16 hours the theoretical amount of water is evolved. The reaction mixture is allowed to cool to room temperature and washed successively with diluted sodium hydroxide solution and twice with water. The solvent is dried and removed in vacuo. The residue is triturated in methanol. The product is filtered off (the filtrate is set aside) and crystallized from butanol, yielding A-2-(bromomethyl)-4-(p-bromophenoxymethyl)-2-(2,4-dichlorophenyl)-1,3-dioxolane.

The filtrate (see above) is evaporated. The residue is dissolved in 210 parts of 2,2'-oxybispropane and the solution is allowed to crystallize. The precipitated product is filtered off and discarded. The filtrate is evaporated and the residue is dissolved in 400 parts of a mixture of hexane and trichloromethane (3:1 by volume). The undissolved part is filtered off and discarded. The filtrate is purified twice by column-chromatography over silica gel using a mixture of hexane and trichloromethane (3:1 by volume) as eluent. The pure fractions are collected and the eluent is evaporated. The residue solidifies on triturating in petroleumether. The product is filtered off and dried, yielding B-2-(bromomethyl)-4-(4-bromophenoxymethyl)-2-(2,4-dichlorophenyl)-1,3-dioxolane.

EXAMPLE XXVII

A mixture of 11.8 parts of 3-(2,6-dimethylphenoxy)-1,2-propanediol, 13.6 parts of 2-bromo-1-(2,4-dichlorophenyl)-1-ethanone, 3 parts of 4-methylbenzenesulfonic acid, 80 parts of butanol and 180 parts of methylbenzene is stirred and refluxed for 3 days. The reaction mixture is evaporated and the residue is dissolved in 2,2'-oxybispropane. The solution is stirred for 30 minutes with silica gel. The latter is filtered off and the filtrate is evaporated, yielding A + B 2-(bromomethyl)-2-(2,4-dichlorophenyl)-4-(2,6-dimethylphenoxymethyl)-1,3-dioxolane as a residue.

EXAMPLE XXVIII

A mixture of 11.2 parts of 2,2',4'-trichloroacetophenone, 14.9 parts of 1-(2,4-dichlorophenoxy)-2,3-propanediol, 3 parts of p-toluenesulfonic acid and 240 parts of benzene is stirred and refluxed for 20 hours in a four-necked, round-bottomed flask, equipped with a water-trap. The reaction mixture is washed successively with a diluted sodium hydroxide solution and twice with water. The solvent is removed in vacuo. The residue is triturated in methanol for 3 hours. The precipitated product is filtered off and crystallized from 2-propanol, yielding A-2-(chloromethyl)-4-(2,4-dichlorophenoxymethyl)-2-(2,4-dichlorophenyl)-1,3-dioxolane; mp. 92.5° C.

EXAMPLE XXIX

A mixture of 24 parts of 3-(4-bromophenoxy)-1,2-propanediol, 28 parts of 2-(bromomethyl)-2-(2,3,4-trichlorophenyl)-1,3-dioxolane, 4 parts of 4-methylbenzenesulfonic acid, 40 parts of butanol and 225 parts of methylbenzene is stirred and refluxed for 2 days. The reaction mixture is allowed to cool to room temperature and evaporated. The residue is triturated in methanol. The product is filtered off and crystallized from 2-propanol, yielding A-2-(bromomethyl)-4-(4-bromophenoxymethyl)-2-(2,3,4-trichlorophenyl)-1,3-dioxolane.

EXAMPLE XXX

A mixture of 14.4 parts of 1-[2-(4-methylphenyl)ethyl]-ethanediol, 15.6 parts of 2-(bromomethyl)-2-(2,4-dichlorophenyl)-1,3-dioxolane, 5-parts of 4-methylbenzenesulfonic acid, 225 parts of methylbenzene and 40 parts of butanol is stirred and refluxed for 3 days with water-separator. The reaction mixture is evaporated and the residue is dissolved in 2,2′-oxybispropane. The solution is stirred for 30 minutes with silica gel. The latter is filtered off and the filtrate is evaporated, yielding 2-(bromomethyl)-2-(2,4-dichlorophenyl)-4-[2-(4-methylphenyl)ethyl]-1,3-dioxolane as a residue.

EXAMPLE XXXI

To a stirred and refluxing Grignard-complex, previously prepared starting from 98 parts of 1-(chloromethyl)-2,4-dichlorobenzene and 14 parts of magnesium in 70 parts of 1,1-oxybisethane, is added dropwise a solution of 46.5 parts of 2-(chloromethyl)oxirane in 350 parts of 1,1′-oxybisethane. Upon completion, stirring at reflux temperature is continued overnight. The reaction mixture is cooled in an ice-bath and decomposed by dropwise addition of 120 parts of a concentrated hydrochloric acid solution. The whole is poured onto water and the layers are separated. The organic phase is washed three times with water. The aqueous phase is extracted with 1,1′-oxybisethane. The combined organic phases are dried, filtered and evaporated. The residue is distilled, yielding 2,4-dichloro-α-(chloromethyl)benzenepropanol; bp. 130° C. at 0.04 mm. pressure.

EXAMPLE XXXII

Following the procedure of Example XXXI and using equivalent amounts of the appropriate starting materials, the following compounds are prepared:

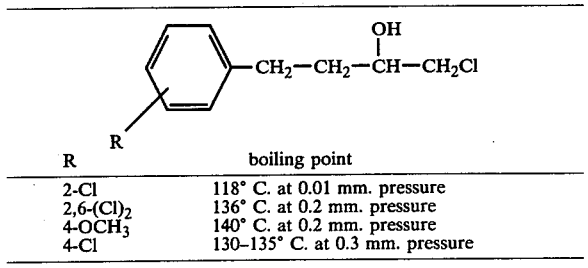

| R | boiling point |
|---|---|
| 2-Cl | 118° C. at 0.01 mm. pressure |
| 2,6-(Cl)$_2$ | 136° C. at 0.2 mm. pressure |
| 4-OCH$_3$ | 140° C. at 0.2 mm. pressure |
| 4-Cl | 130–135° C. at 0.3 mm. pressure |

EXAMPLE XXXIII

A solution of 87 parts of 2,4-dichloro-α-(chloromethyl)-benzenepropanol in 144 parts of concentrated sodium hydroxide solution and 350 parts of 2,2′-oxybispropane is stirred overnight at room temperature. The product is extracted with 2,2′-oxybispropane. The extract is washed with water, dried, filtered and evaporated. The oily residue is distilled, yielding [2-(2,4-dichlorophenyl)ethyl]oxirane; bp. 90°–98° C. at 0.01 mm. pressure.

EXAMPLE XXXIV

Following the procedure of Example XXXIII and using equivalent amounts of the appropriate starting materials, the following oxirane derivatives are prepared:

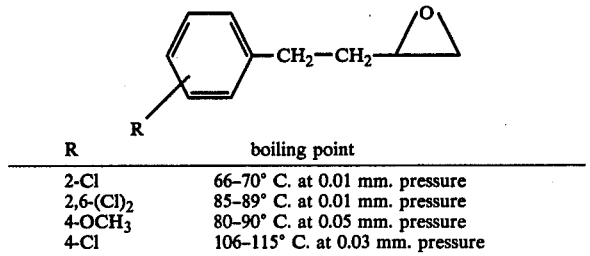

| R | boiling point |
|---|---|
| 2-Cl | 66–70° C. at 0.01 mm. pressure |
| 2,6-(Cl)$_2$ | 85–89° C. at 0.01 mm. pressure |
| 4-OCH$_3$ | 80–90° C. at 0.05 mm. pressure |
| 4-Cl | 106–115° C. at 0.03 mm. pressure |

EXAMPLE XXXV

A mixture of 50 parts of [2-(2,4-dichlorophenyl)ethyl]-oxirane, 7 parts of ethanedioic acid, 300 parts of 1,4-dioxane and 150 parts of water is stirred and refluxed for 36 hours. The reaction mixture is evaporated. The residue is crystallized from 2,2′-oxybispropane. The product is filtered off and dried at the air, yielding 1-[2-(2,4-dichlorophenyl)ethyl]ethanediol; mp. 83.2° C.

EXAMPLE XXXVI

By repeating the procedure of Example XXXV and using therein an equivalent amount of the appropriate starting material, the following compounds are prepared:
1-[2-(2-chlorophenyl)ethyl]ethanediol; mp. 64.1° C.;
4-(2,6-dichlorophenyl)-1,2-butanediol; mp. 111.7° C.; and
1-[2-(4-chlorophenyl)ethyl]ethanediol; bp. 150° C. at 0.02 mm. pressure.

EXAMPLE XXXVII

To a stirred solution of 12 parts of 2-[2-(4-methoxyphenyl)-ethyl]oxirane in 1.8 parts of sulfuric acid and 160 parts of 2-propanone are added 100 parts of water. The whole is stirred for 2 days at room temperature. The reaction mixture is stirred with a sodium bicarbonate solution and the product is extracted with trichloromethane. The extract is dried, filtered and evaporated, yielding 1-[2-(4-methoxyphenyl)ethyl]-1,2-ethanediol as a residue.

EXAMPLE XXXVIII

A mixture of 13.6 parts of 2-bromo-1-(2,4-dichlorophenyl)-1-ethanone, 14.1 parts of 1-[2-(2,4-dichlorophenyl)ethyl]ethanediol, 3 parts of 4-methylbenzenesulfonic acid, 80 parts of butanol and 180 parts of benzene is stirred and refluxed for 24 hours. The reaction mixture is evaporated and the residue is stirred for 2 hours with 160 parts of methanol. The precipitated product is filtered off, yielding 2-(bromomethyl)-2-(2,4-dichlorophenyl)-4-[2-(2,4-dichlorophenyl)ethyl]-1,3-dioxolane.

EXAMPLE XXXIX

Following the procedure of Example XXXVIII and using an equivalent amount of the appropriate starting material, the following dioxolanes are prepared:
2-(bromomethyl)-4-[2-(2-chlorophenyl)ethyl]-2-(2,4-dichlorophenyl)-1,3-dioxolane;
2-(bromomethyl)-2-(2,4-dichlorophenyl)-4-[2-(2,6-dichlorophenyl)ethyl]-1,3-dioxolane; and
A + B 2-(bromomethyl)-2-(2,4-dichlorophenyl)-4-[2-(4-methoxyphenyl)-ethyl]-1,3-dioxolane.

EXAMPLE XL

A mixture of 11.2 parts of 1-[2-(4-chlorophenyl)ethyl]-ethanediol, 15.6 parts of 2-(bromomethyl)-2-(2,4-dichlorophenyl)-1,3-dioxolane, 4 parts of 4-methylbenzenesulfonic acid, 40 parts of butanol and 225 parts of methylbenzene is stirred and refluxed for 5 days with water-separator. The reaction mixture is evaporated and the residue is dissolved in 2,2'-oxybispropane. The solution is stirred with silica gel. The latter is filtered off and the filtrate is evaporated, yielding 2-(bromomethyl)-4-[2-(4-chlorophenyl)ethyl]-2-(2,4-dichlorophenyl)-1,3-dioxolane as a residue.

EXAMPLE XLI

Following the procedure of Example XL and using therein an equivalent amount of 4-phenyl-1,2-butanediol as a starting material, there is obtained: 2-(bromomethyl)-2-(2,4-dichlorophenyl)-4-(2-phenylethyl)-1,3-dioxolane as a residue.

EXAMPLE XLII

To a stirred and refluxing Grignard-complex, previously prepared starting from 89 parts of 4-(chloromethyl)-1,1'-biphenyl and 12.5 parts of magnesium in 350 parts of 1,1'-oxybisethane, is added dropwise a solution of 60 parts of 3-bromo-1-propene in 180 parts of tetrahydrofuran. Upon completion, stirring is continued for 2.50 hours at reflux temperature. The reaction mixture is cooled and poured onto water. The layers are separated and the aqueous phase is extracted with 1,1'-oxybisethane. The combined organic phases are washed with water, dried, filtered and evaporated. The residue is filtered and the filtrate is evaporated, yielding 60 parts of 4-(3-butenyl)-1,1'-biphenyl as a residue.

To a stirred mixture of 88 parts of 3-chlorobenzeneperoxoic acid and 650 parts of dichloromethane are added dropwise 60 parts of 4-(3-butenyl)-1,1'-biphenyl. Upon completion, stirring is continued over week-end at room temperature. Then there are added dropwise 50 parts of a potassium carbonate solution. The organic phase is separated, washed with a sodium bisulfite solution and with water, dried, filtered and evaporated, yielding 63.5 parts (70.87%) of [2-([1,1'-biphenyl]-4-yl)ethyl]oxirane as an oily residue.

EXAMPLE XLIII

To a stirred mixture of 86 parts of 3-chlorobenzeneperoxoic acid and 650 parts of dichloromethane are added dropwise (slowly) 53 parts of 1-fluoro-4-(2-propenyl)benzene. Upon completion, stirring is continued overnight at room temperature. Then there are added dropwise 92 parts of a potassium carbonate solution and the layers are separated. The organic phase is washed with a sodium bisulfite solution, dried, filtered and evaporated, yielding 58.4 parts (98%) of 2-(4-fluorophenylmethyl)oxirane as an oily residue.

EXAMPLE XLIV

To a stirred mixture of 44.5 parts of 4-chloro-1-naphthalenol and 115 parts of 2-(chloromethyl)oxirane are added portionwise 17.1 parts of potassium hydroxide (exothermic reaction). When the exothermic reaction is ceased, the whole is heated to reflux and stirred at reflux temperature for 2 hours. Water is added and the whole is extracted twice with trichloromethane. The combined extracts are washed three times with water, dried and evaporated. The residue is distilled, yielding 45.3 parts of 2-[(4-chloro-1-naphthalenyloxy)-methyl]oxirane; bp. 150°–151° C. at 0.2 mm. pressure.

EXAMPLE XLV

To a stirred solution of 139 parts of 2-nitrophenol and 138 parts of potassium carbonate in 640 parts of 2-propanone are added dropwise 215 parts of 2-(chloromethyl)oxirane. Upon completion, stirring is continued for 2 days at reflux. The formed precipitate is filtered off and the filter-cake is washed with 2-propanone. The filtrate is evaporated. The residue is crystallized from a mixture of 2,2'-oxybispropane and petroleumether (1:1 by volume). The product is filtered off and dried, yielding 38 parts (20%) of 2-(2-nitrophenoxymethyl)oxirane; mp. 56° C.

EXAMPLE XLVI

Following the procedure of Example XLV and using an equivalent amount of a appropriately substituted phenol or naphthalenol in place of the 2-nitrophenol used therein, the following 2-aryloxymethyloxiranes are obtained:
2-[(2-chloro-5-methylphenoxy)methyl]oxirane; bp. 115° C. at 0.05 mm. pressure;
2-(3,4,5-trichlorophenoxymethyl)oxirane as an oily residue;
2-(3-chloro-[1,1'-biphenyl]-4-yloxymethyl)oxirane as a residue; and
2-[(1,6-dibromo-2-naphthalenyloxy)methyl]oxirane as a solid residue.

EXAMPLE XLVII

To a stirred solution of 38 parts of 2-(2-nitrophenoxymethyl)-oxirane in 10 parts of ethanedioic acid and 300 parts of 1,4-dioxane are added 100 parts of water. The whole is stirred and refluxed for 2 days. The reaction mixture is evaporated and the residue is crystallized from a mixture of 2,2'-oxybispropane and petroleumether. The product is filtered off and recrystallized from 2,2'-oxybispropane, yielding 29.5 parts (13%) of 3-(2-nitrophenoxy)-1,2-propanediol; mp. 96° C.

EXAMPLE XLVIII

Following the procedure of Example XLVII and using an equivalent amount of an appropriately substituted oxirane in place of the 2-[(2-nitrophenoxy)methyl]oxirane used therein, the following diols are obtained:
3-(4-chloro-1-naphthalenyloxy)-1,2-propanediol; mp. 120° C.;
3-(2-chloro-5-methylphenoxy)-1,2-propanediol; mp. 59° C.;
3-[4-(phenylmethyl)phenoxy]-1,2-propanediol; mp. 70° C.;
3-(3,4,5-trichlorophenoxy)-1,2-propanediol; mp. 64° C.;
3-(3-chloro-[1,1'-biphenyl]-4-yloxy)-1,2-propanediol; mp. 60° C.;

3-(1,6-dibromo-2-naphthalenyloxy)-1,2-propanediol; mp. 139° C.;

3-(4-bromophenyl)-1,2-propanediol; mp. 60.6° C.;

3-(4-fluorophenyl)-1,2-propanediol; bp. 125° C. at 0.05 mm. pressure; and 4-([1,1'-biphenyl]-4-yl)-1,2-butanediol; mp. 125.9° C.

EXAMPLE IL

A mixture of 13.5 parts of 1,2-butanediol, 37.5 parts 2-bromo-1-(2,4-dichlorophenyl)ethanone, 2 parts of 4-methylbenzenesulfonic acid, 40 parts of butanol and 225 parts of methylbenzene is stirred and refluxed for 24 hours with water-separator. The reaction mixture is cooled, washed twice with a sodium bicarbonate solution, dried, filtered and evaporated. The residue is distilled, yielding 38 parts (80%) of A+B-2-(bromomethyl)-2-(2,4-dichlorophenyl)-4-ethyl-1,3-dioxolane; bp. 125°–130° C. at 0.1 mm. pressure.

EXAMPLE L

Following the procedure of Example IL and using equivalent amounts of the appropriate starting materials, the following dioxolanes are prepared:

| R | $R^6$ | boiling point |
|---|---|---|
| $C_2H_5$ | 2-Cl | 97–99° C. at 0.05 mm. pressure |
| $C_2H_5$ | 2-$CH_3$ | 86–88° C. at 0.05 mm. pressure |
| $C_2H_5$ | 4-$CH_3$ | 100° C. at 0.05 mm. pressure |
| $C_2H_5$ | 2-Br | 114–115° C. at 0.05 mm. pressure |
| $C_2H_5$ | 3-Cl | 140° C. at 0.6 mm. pressure |
| $C_2H_5$ | 2-Cl,4-Br | — |
| $C_2H_5$ | 4-$OCH_3$ | 122° C. at 0.15 mm. pressure |
| $C_2H_5$ | 3,4,5-$(Cl)_3$ | 135° C. at 0.05 mm. pressure |
| $nC_3H_7$ | 2,4-$(Cl)_2$ | 102–125° C. at 0.05 mm. pressure |
| $nC_4H_9$ | 2,4-$(Cl)_2$ | 137–139° C. at 0.05 mm. pressure |
| $nC_5H_{11}$ | 2,4-$(Cl)_2$ | 140–145° C. at 0.03 mm. pressure |
| $nC_6H_{13}$ | 2,4-$(Cl)_2$ | 163–170° C. at 0.1 mm. pressure |
| $nC_7H_{15}$ | 2,4-$(Cl)_2$ | 160–165° C. at 0.05 mm. pressure |
| $nC_8H_{17}$ | 2,4-$(Cl)_2$ | 180–190° C. at 0.05 mm. pressure |

EXAMPLE LI

A mixture of 28.5 parts of 3-(3,4,5-trichlorophenoxy)-1,2-propanediol, 18.4 parts of 2-bromo-1-(2,4-dichlorophenyl)ethanone, 3 parts of 4-methylbenzenesulfonic acid, 40 parts of butanol and 225 parts of methylbenzene is stirred and refluxed over week-end. The reaction mixture is evaporated. The oily residue is purified by column-chromatography over silica gel using trichloromethane as eluent. The pure fractions are collected and the eluent is evaporated, yielding 17.5 parts (48%) of A+B-2-(bromomethyl)-2-(2,4-dichlorophenyl)-4-(3,4,5-trichlorophenoxymethyl)-1,3-dioxolane as a residue.

EXAMPLE LII

Following the procedure of Example LI and using equivalent amounts of the appropriate starting materials, the following dioxolanes are prepared:

A-2-(bromomethyl)-4-(2-bromo-4-methylphenoxymethyl)-2-(2,4-dichlorophenyl)-1,3-dioxolane;

2-(bromomethyl)-4-(2-chloro-5-methylphenoxymethyl)-2-(2,4-dichlorophenyl)-1,3-dioxolane as an oily residue;

A+B-2-(bromomethyl)-4-[(1,6-dibromo-2-naphthalenyloxy)methyl]-2-(2,4-dichlorophenyl)-1,3-dioxolane; and A+B-2-(bromomethyl)-2-(2,4-dichlorophenyl)-1,3-dioxolane-4-methanol; bp. 145°–150° C. at 0.05 mm. pressure.

EXAMPLE LIII

Following the procedure of Example LI and using equivalent amounts of the appropriate starting materials and dimethylbenzene as a solvent in place of the methylbenzene used therein, the following dioxolanes are still prepared:

A+B-4-([1,1'-biphenyl]-4-yloxymethyl)-2-(4-bromo-2-chlorophenyl)-2-(bromomethyl)-1,3-dioxolane;

A+B-2-(bromomethyl)-2-(2,4-dichlorophenyl)-4-(phenylmethyl)-1,3-dioxolane as a residue;

4-([1,1'-biphenyl]-2-yloxymethyl)-2-(bromomethyl)-2-(2,4-dichlorophenyl)-1,3-dioxolane as an oily residue;

A+B-2-(bromomethyl)-2-(2,4-dichlorophenyl)-4-[(4-fluorophenyl)-thiomethyl]-1,3-dioxolane as a residue;

A+B-2-(bromomethyl)-4-(4-chlorophenylmethyl)-2-(2,4-dichlorophenyl)-1,3-dioxolane;

A+B-2-(bromomethyl)-2-(2,4-dichlorophenyl)-4-(4-methoxyphenylmethyl)-1,3-dioxolane as a residue; and A+B-4-([1,1'-biphenyl]-4-yloxymethyl)-2-(bromomethyl)-2-(3,4,5-trichlorophenyl)-1,3-dioxolane as a residue.

EXAMPLE LIV

A mixture of 15.2 parts of 2-bromo-1-(2,4-dichlorophenyl)-ethanone, 17.6 parts of 2-(2,3-dihydroxypropoxy)benzonitrile, 3 parts of 4-methylbenzenesulfonic acid, 40 parts of 1-butanol and 225 parts of dimethylbenzene is stirred and refluxed for 3 days with water-separator. The reaction mixture is evaporated. The residue is triturated in methanol. The product is filtered off and dried, yielding 10 parts (45%) of A-2-[2-(bromomethyl)-2-(2,4-dichlorophenyl)-1,3-dioxolan-4-ylmethoxy]benzonitrile.

EXAMPLE LV

A mixture of 13.6 parts of butyl 4-(2,3-dihydroxypropoxy)-benzoate, 15.2 parts of 2-bromo-1-(2,4-dichlorophenyl)ethanone, 3 parts of 4-methylbenzenesulfonic acid, 40 parts of 1-butanol and 225 parts of dimethylbenzene is stirred and refluxed for 3 days with water-separator. The reaction mixture is evaporated and the residue is triturated in methanol. The product is filtered off and crystallized from 2-propanol, yielding 8.7 parts (39%) of A-butyl 4-[2-(bromomethyl)-2-(2,4-dichlorophenyl)-1,3-dioxolan-4-ylmethoxy]benzoate.

EXAMPLE LVI

A mixture of 15.2 parts of 2-bromo-1-(2,4-dichlorophenyl)ethanone, 16.7 parts of 3-(3-chloro-[1,1'-biphenyl]-4-yloxy)-1,2-propanediol, 3 parts of 4-methylbenzenesulfonic acid, 40 parts of butanol and 225 parts of dimethylbenzene is stirred and refluxed for 2 days with water-separator. The reaction mixture is allowed to cool to room temperature and 2,2'-oxybispropane is added. The organic phase is washed with a diluted sodium hydroxide solution 5N and with water, dried, evaporated. The residue is triturated in a mixture of 2,2'-oxybispropane and petroleumether. The product is filtered off (the filtrate is set aside) and dried, yielding 12.5 parts of A-2-(bromomethyl)-4-(3-chloro-[1,1'-biphenyl]-4-yloxymethyl)-2-(2,4-dichlorophenyl)-1,3-dioxolane. The filtrate (see above) is evaporated. The residue is dissolved in trichloromethane and the solution is stirred with silica gel. The latter is filtered off and the filtrate is evaporated, yielding 10 parts of A+B-2-(bromomethyl)-4-(3-chloro-[1,1'-biphenyl]-4-yloxymethyl)-2-(2,4-dichlorophenyl)-1,3-dioxolane as a residue.

EXAMPLE LVII

A mixture of 18.1 parts of 3-[4-(phenylmethyl)-phenoxy]-1,2-propanediol, 13.4 parts of 2-bromo-1-(2,4-dichlorophenyl)ethanone, 3 parts of 4-methylbenzenesulfonic acid, 40 parts of butanol and 225 parts of methylbenzene is stirred and refluxed over week-end. The reaction mixture is evaporated and the oily residue is triturated in methanol. The product is filtered off (the filtrate is set aside), yielding 15 parts of A-2-(bromomethyl)-2-(2,4-dichlorophenyl)-4-[4-(phenylmethyl)-phenoxymethyl]-1,3-dioxolane; mp. 96° C. The filtrate, which was set aside, is evaporated. The oily residue is purified by column-chromatography over silica gel using a mixture of trichloromethane and 20% of hexane as eluent. The pure fractions are collected and the eluent is evaporated, yielding 13 parts of B-2-(bromomethyl)-2-(2,4-dichlorophenyl)-4-[4-(phenylmethyl)-phenoxymethyl]-1,3-dioxolane as an oily residue.

EXAMPLE LVIII

A mixture of 14.9 parts of 3-(2-nitrophenoxy)-1,2-propanediol, 13.4 parts of 2-bromo-1-(2,4-dichlorophenyl)ethanone, 3 parts of 4-methylbenzenesulfonic acid, 40 parts of butanol and 225 parts of methylbenzene is stirred and refluxed over week-end. The reaction mixture is evaporated and the oily residue is dissolved in trichloromethane. The solution is washed with a diluted sodium hydroxide solution 20% and with water, dried, filtered and evaporated. The oily residue is crystallized from 2,2'-oxybispropane while stirring. The product is filtered off (the filtrate is set aside), yielding 8.5 parts of A-2-(bromomethyl)-2-(2,4-dichlorophenyl)-4-(2-nitrophenoxymethyl)-1,3-dioxolane. The filtrate which was set aside, is evaporated. The oily residue is purified twice by column-chromatography over silica gel using, first trichloromethane and second a mixture of trichloromethane and 20% of hexane as eluent. The pure fractions are collected and the eluent is evaporated, yielding 14.5 parts of B-2-(bromomethyl)-2-(2,4-dichlorophenyl)-4-(2-nitrophenoxymethyl)-1,3-dioxolane as an oily residue.

EXAMPLE LIX

To a stirred and hot (50° C.) solution of 64 parts of 1-(3-bromo-4-methylphenyl)-1-ethanone in 160 parts of 1-butanol are added dropwise, during a 1 hour-period, 48 parts of bromine without external heating. After stirring for 1 hour at room temperature, there are added successively 21.7 parts of 1,2-ethanediol, 6 parts of 4-methylbenzenesulfonic acid and 720 parts of benzene and the whole is stirred and refluxed overnight with water-separator. The reaction mixture is evaporated and the residue is taken up in 2,2'-oxybispropane. The resulting solution is washed successively once with a diluted sodium hydroxide solution and three times with water, dried, filtered and evaporated. The residue is distilled, yielding 57 parts (57%) of 2-(bromomethyl)-2-(3-bromo-4-methylphenyl)-1,3-dioxolane; bp. 126°–130° C. at 0.1 mm. pressure.

EXAMPLE LX

Following the procedure of Example LIX and using an equivalent amount of an appropriate 1-aryl-1-ethanone in place of the 1-(3-bromo-4-methylphenyl)-1-ethanone used therein the following 2-aryl-2-(bromomethyl)-1,3-dioxolanes are prepared:

2-(bromomethyl)-2-(4-chloro-2-methylphenyl)-1,3-dioxolane;
2-(bromomethyl)-2-(3,5-dichlorophenyl)-1,3-dioxolane; mp. 58° C.;
2-(bromomethyl)-2-(2,3-dichlorophenyl)-1,3-dioxolane; bp. 135°–137° C. at 0.1 mm. pressure;
2-(bromomethyl)-2-(2,4,5-trichlorophenyl)-1,3-dioxolane; bp. 146°–147° C. at 0.3 mm. pressure; and
2-(bromomethyl)-2-(2-chloro-4-methoxyphenyl)-1,3-dioxolane; mp. 53° C.

EXAMPLE LXI

To a stirred solution of 112 parts of 4-(2-bromoacetyl)-benzonitrile in 320 parts of butanol are added 5 parts of 4-methylbenzenesulfonic acid and 360 parts of benzene. Then there are added dropwise 46.5 parts of 1,2-ethanediol. Upon completion, stirring is continued for 4 hours at reflux. The reaction mixture is evaporated. The oily residue is crystallized from 2,2'-oxybispropane. The product is filtered off and recrystallized from methanol, yielding 95.12 parts of 4-[2-(bromomethyl)-1,3-dioxolan-2-yl]benzonitrile; mp. 92.4° C.

EXAMPLE LXII

Following the procedure of Example LXI and using an equivalent amount of an appropriate 1-aryl-2-bromo-1-ethanone in place of the 4-(2-bromoacetyl)benzonitrile used therein, the following 2-aryl-2-(bromomethyl)-1,3-dioxolanes are prepared:

2-(bromomethyl)-2-(2-naphthalenyl)-1,3-dioxolane; mp. 64° C.;
2-(bromomethyl)-2-(4-bromo-2-methylphenyl)-1,3-dioxolane; mp. 86° C.;
2-(bromomethyl)-2-(3-bromophenyl)-1,3-dioxolane; mp. 50° C.; and
2-(bromomethyl)-2-(3-nitrophenyl)-1,3-dioxolane; mp. 88° C.

EXAMPLE LXIII

A mixture of 19.8 parts of 3-(4-bromophenoxy)-1,2-propanediol, 15.6 parts of 2-(bromomethyl)-2-(3,5-dichlorophenyl-1,3-dioxolane, 4 parts of 4-methylbenzenesulfonic acid, 40 parts of butanol and 225 parts of benzene is stirred and refluxed for 2 days with water-separator. The reaction mixture is allowed to cool to room temperature and the solvent is removed by evaporation in vacuo. The residue is triturated in methanol. The product is filtered off and crystallized from 2-propanol yielding 5.5 parts (22%) of A-2-(bromomethyl)-4-(4-bromophenoxymethyl)-2-(3,5-dichlorophenyl)-1,3-dioxolane.

EXAMPLE LXIV

Following the procedure of Example LXIII and using equivalent amounts of the appropriate starting materials, the following dioxolanes are prepared by carrying out the reaction in the indicated solvent:

Using methylbenzene as a solvent there are prepared:
A-2-(bromomethyl)-4-(4-bromophenoxymethyl)-2-(4-chloro-2-methylphenyl)-1,3-dioxolane; mp. 155° C.;
A-2-(bromomethyl)-4-(4-bromophenoxymethyl)-2-(3-bromophenyl)-1,3-dioxolane; mp. 92.2° C.;
A-2-(bromomethyl)-2-(4-bromo-2-methylphenyl)-4-(4-bromophenoxymethyl)-1,3-dioxolane;
A-2-(bromomethyl)-2-(3-bromo-4-methylphenyl)-4-(4-bromophenoxymethyl)-1,3-dioxolane; mp. 100° C.;
A-4-[2-(bromomethyl)-4-(4-bromophenoxymethyl)-1,3-dioxolan-2-yl]-benzonitrile;
A-2-(bromomethyl)-4-(4-bromophenoxymethyl)-2-(3-nitrophenyl)-1,3-dioxolane; and
A-2-(bromomethyl)-4-(4-bromophenoxymethyl)-2-(2,3-dichlorophenyl)-1,3-dioxolane.
Using dimethylbenzene as a solvent there are prepared:
A+B-4-([1,1'-biphenyl]-4-yloxymethyl)-2-(bromomethyl)-2-(2-naphthalenyl)-1,3-dioxolane; mp. 160.8° C.;
A-4-([1,1'-biphenyl]-4-yloxymethyl)-2-(bromomethyl)-2-(2-chloro-4-methoxyphenyl)-1,3-dioxolane;
A+B-2-(bromomethyl)-4-ethyl-2-(2,3,4-trichlorophenyl)-1,3-dioxolane; bp. 145° C. at 0.1 mm. pressure;
A+B-4-([1,1'-biphenyl]-4-yloxymethyl)-2-(bromomethyl)-2-(2,4,5-trichlorophenyl)-1,3-dioxolane as a residue;
A+B-2-(bromomethyl)-2-(2,3-dichlorophenyl)-4-ethyl-1,3-dioxolane; bp. 131°-133° C. at 0.1 mm. pressure;
A+B-2-(bromomethyl)-2-(2-chloro-4-methoxyphenyl)-4-ethyl-1,3-dioxolane; bp. 142°-144° C. at 0.3 mm. pressure;
A+B-2-(bromomethyl)-2-(4-chloro-2-methylphenyl)-4-ethyl-1,3-dioxolane; bp. 118° C. at 0.15 mm. pressure; and
A+B-2-(bromomethyl)-4-ethyl-2-(2-naphthalenyl)-1,3-dioxolane as a residue.

EXAMPLE LXV

To a stirred and warm solution of 6.5 parts of 1,2-butanediol, 13 parts of 1-(4-chloro-2-methoxyphenyl)ethanone and 40 parts of butanol are added dropwise (slowly) 5.7 parts of bromine at about 40° C. After stirring for 30 minutes, there are added 2 parts of 4-methylbenzenesulfonic acid and 225 parts of methylbenzene and the whole is stirred and refluxed overnight with water-separator. The reaction mixture is cooled, washed with a potassium carbonate solution, dried filtered and evaporated. The residue is distilled, yielding 17 parts (63%) of A+B-2-(bromomethyl)-2-(4-chloro-2-methoxyphenyl)-4-ethyl-1,3-dioxolane; bp. 135°-140° C. at 0.3 mm. pressure.

EXAMPLE LXVI

Following the procedure of Example LXV and using an equivalent amount of 1-(2,4,5-trichlorophenyl)ethanone in place of the 1-(4-chloro-2-methoxyphenyl)ethanone, there is obtained:
A+B-2-(bromomethyl)-4-ethyl-2-(2,4,5-trichlorophenyl)-1,3-dioxolane; bp. 145° C. at 0.2 mm. pressure.

EXAMPLE LXVII

To a stirred solution of 53 parts of 1-(2,4-dibromophenyl)ethanone in 105 parts of 1,1'-oxybisethane, are added dropwise, during a 2 hours-period, 32 parts of bromine. Then there are added carefully 68 parts of 1H-imidazole and 135 parts of N,N-dimethylformamide and the whole is stirred for 2 hours at 50° C. Upon the addition of water, the product precipitates. It is filtered off, washed with water and dissolved in trichloromethane. The solution is dried, filtered and evaporated. The residue is converted into the hydrochloride salt in 2-propanone and 2-propanol. Upon the addition of 2,2'-oxybispropane, the product is crystallized. It is filtered off, washed with 2-propanone and recrystallized from a mixture of ethanol and 2,2'-oxybispropane, yielding 28.3 parts of 1-(2,4-dibromophenyl)-2-(1H-imidazol-1-yl)ethanone hydrochloride; mp. 204.7° C.

EXAMPLE LXVIII

To a stirred solution of 78.7 parts of 2-bromo-1-(2-chloro-4-fluorophenyl)ethanone in 140 parts of 1,1'-oxybisethane are added carefully 106.4 parts of 1H-imidazole. Upon completion, there are added 180 parts of N,N-dimethylformamide and the whole is stirred for 2 hours at 50° C. After the addition of water, the product is extracted twice with trichloromethane. The combined extracts are washed three times with water, dried, filtered and evaporated. The residue is converted into the hydrochloride salt in 4-methyl-2-pentanone, 2,2'-oxybispropane and 2-propanol. The salt is filtered off and crystallized from a mixture of ethanol and 2,2'-oxybispropane, yielding 1.5 parts of 1-(2-chloro-4-fluorophenyl)-2-(1H-imidazol-1-yl)ethanone hydrochloride; mp. 197.4° C.

EXAMPLE LXIX

A. To a stirred mixture of 67.2 parts of A+B-2-(bromomethyl)-2-(2,4-dichlorophenyl)-1,3-dioxolane-4-methanol and 100 parts of pyridine are added dropwise 27.2 parts of benzoyl chloride while cooling at a temperature below 10° C. Upon completion, stirring is continued for 2.50 hours at room temperature. The reaction mixture is poured onto water and the product is extracted with trichloromethane. The extract is washed successively with a diluted hydrochloric acid solution, to remove the last traces of pyridine, and with water, dried filtered and evaporated. The oily residue is triturated in methanol. The solid product is filtered off (the filtrate is set aside) and crystallized twice from ethanol, yielding 28 parts of cis-2-(bromomethyl)-2-(2,4-dichlorophenyl)-1,3-dioxolan-4-ylmethyl benzoate; mp. 118.3° C. The filtrate (see above) is evaporated. The oily residue is purified by column-chromatography over silica gel using 2,2'-oxybispropane as eluent. The pure fractions are collected and the eluent is evaporated. The oily residue is triturated in methanol. The solid product is purified by column-chromatography over silica gel using trichloromethane and hexane (30:70) as eluent. The pure fractions are collected and the eluent is evaporated, yielding 17.5 parts of trans-2-(bromomethyl)-2-(2,4-dichlorophenyl)-1,3-dioxolan-4-ylmethyl benzoate; mp. 68.6° C.

B. A mixture of 12 parts of cis-2-(bromomethyl)-2-(2,4-dichlorophenyl)-1,3-dioxolan-4-ylmethyl benzoate, 7.5 parts of sodium hydroxide solution 60%, 100 parts of water and 200 parts of 1,4-dioxane is stirred and refluxed for 1 hour. The reaction mixture is cooled, poured onto water and the product is extracted with trichloromethane. The extract is washed with water, dried, filtered and evaporated. The oily residue is purified by column-chromatography over silica gel using a mixture of trichloromethane, hexane and methanol (50:49:1) as eluent. The pure fractions are collected and the eluent is evaporated, yielding 4.5 parts of cis-2-

(bromomethyl)-2-(2,4-dichlorophenyl)-1,3-dioxolane-4-methanol as a residue.

Following the procedure of Example LXIX-B and using an equivalent amount of trans-2-(bromomethyl)-2-(2,4-dichlorophenyl)-1,3-dioxolan-4-ylmethyl benzoate in place of the cis-2-(bromomethyl)-2-(2,4-dichlorophenyl)-1,3-dioxolan-4-ylmethyl benzoate, there is obtained:
trans-2-(bromomethyl)-2-(2,4-dichlorophenyl)-1,3-dioxolane-4-methanol as a residue.

EXAMPLE LXX

A mixture of 4.5 parts of methanesulfonyl chloride, 10 parts of cis-2-(2,4-dichlorophenyl)-2-(1H-imidazol-1-ylmethyl)-1,3-dioxolane-4-methanol and 50 parts of pyridine is allowed to stand for 3 hours at room temperature. The reaction mixture is poured onto water. The precipitated product is filtered off and crystallized from benzene, yielding 10.3 parts (87%) of cis-2-(2,4-dichlorophenyl)-2-(1H-imidazol-1-ylmethyl)-1,3-dioxolan-4-ylmethyl methanesulfonate; mp. 111.7° C.

EXAMPLE LXXI

A mixture of 32 parts of 1,2,4-butanetriol, 60 parts of 2-bromo-1-(2,4-dichlorophenyl)ethanone, 2 parts of 4-methylbenzenesulfonic acid, 40 parts of butanol and 225 parts of methylbenzene is stirred and refluxed overnight with water-separator. The reaction mixture is cooled, washed with a potassium carbonate solution, dried, filtered and evaporated. The residue is purified by column-chromatography over silica gel using a mixture of trichloromethane and methanol (99:1) as eluent. The pure fractions are collected and the eluent is evaporated, yielding 34 parts (43%) of A+B-2-(bromomethyl)-2-(2,4-dichlorophenyl)-1,3-dioxolane-4-ethanol as a residue.

To a stirred mixture of 20 parts of A+B-2-(bromomethyl)-2-(2,4-dichlorophenyl)-1,3-dioxolane-4-ethanol and 50 parts of pyridine are added dropwise, 6.9 parts of methanesulfonyl chloride. Upon completion, stirring at room temperature is continued for 2 hours. The reaction mixture is poured onto water and the product is extracted twice with 1,1'-oxybisethane. The combined extracts are washed successively twice with a diluted hydrochloric acid solution and once with water, dried, filtered and evaporated, yielding 25 parts (100%) of A+B-{2-[2-(bromomethyl)-2-(2,4-dichlorophenyl)-1,3-dioxolan-4-yl]ethyl}methanesulfonate as a residue.

To a stirred mixture of 25 parts of A+B-{2-[2-(bromomethyl)-2-(2,4-dichlorophenyl)-1,3-dioxolan-4-yl]ethyl}methanesulfonate and 100 parts of dimethylsulfoxide are added 2.2 parts of sodium hydride dispersion 78% at room temperature. Stirring is continued for 3 hours at 50° C. The reaction mixture is poured onto water and the product is extracted twice with 2,2'-oxybispropane. The combined extracts are washed twice with water, dried, filtered and evaporated. The residue is purified by column-chromatography over silica gel using trichloromethane as eluent. The pure fractions are collected and the eluent is evaporated, yielding 15 parts (79%) of A+B-2-(bromomethyl)-2-(2,4-dichlorophenyl)-4-ethenyl-1,3-dioxolane as a residue.

B. FINAL PRODUCTS OF FORMULA I

EXAMPLE LXXII

A mixture of 1.1 parts of imidazole, 1 part of 2-(bromomethyl)-2,4-bis(4-chlorophenyl)-1,3-dioxolane, 0.4 parts of potassium iodide and 20 parts of dimethylformamide is stirred and refluxed for 12 hours. Water is added and the product is extracted with 1,1'-oxybisethane. The extract is washed twice with water, dried, filtered and evaporated. The residue of 1-[2,4-bis(4-chlorophenyl)-1,3-dioxolan-2-ylmethyl]imidazole is converted into the nitrate salt. The crude salt is filtered off and crystallized from a mixture of 2-propanol and 2,2'-oxybispropane, yielding 1-[2,4-bis(4-chlorophenyl)-1,3-dioxolan-2-ylmethyl]imidazole nitrate; mp. 192.3° C.

EXAMPLE LXXIII

A mixture of 7 parts of imidazole, 7.5 parts of 2-(bromomethyl)-2-(4-chlorophenyl)-4-phenyl-1,3-dioxolane, 2 parts of sodium iodide and 100 parts of N,N-dimethylformamide is stirred and refluxed for 48 hours. The reaction mixture is allowed to cool to room temperature and is poured into water. The product is extracted twice with benzene. The extract is washed twice with water and the solvent is removed in vacuo. The residue of 1-[2-(4-chlorophenyl)-4-phenyl-1,3-dioxolan-2-ylmethyl]-imidazole is converted into the nitrate salt in 4-methyl-2-pentanone and 2,2'-oxybispropane. The crude salt is filtered off and crystallized from 4-methyl-2-pentanone, yielding 1-[2-(4-chlorophenyl)-4-phenyl-1,3-dioxolan-2-ylmethyl]imidazole nitrate; mp. 153.2° C.

EXAMPLE LXXIV

Following the procedure of Example LXXIII and using equivalent amounts of the appropriate starting materials, the following imidazoles and imidazole acid addition salts are prepared:

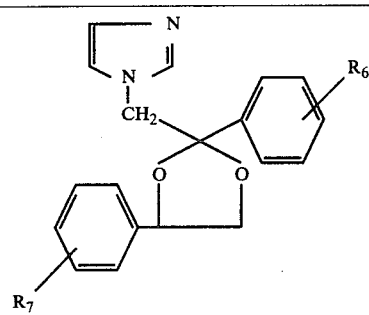

| R₆ | R₇ | Acid salt | Melting point of Salt |
|---|---|---|---|
| 4-Cl | 2,4-(Cl)₂ | HNO₃ | 196.6° |
| 4-Br | 4-Cl | HNO₃ | 152.6° |
| 4-Br | 2,4-(Cl)₂ | HNO₃ | 205.3° |
| 2,4-Cl₂ | — | 2(COOH)₂ | 107.7° |
| 4-OCH₃ | 4-Cl | HNO₃ | 196.3° |
| — | 2,4-(Cl)₂ | HNO₃ | 163.8° |
| 2,4-(CL)₂ | 4-Cl | 1.5(COOH)₂ | 119.9° |
| — | 4-Cl | HNO₃ | 134.7° |
| 4-Cl | 2-Cl | HNO₃ | 183.8° |
| 2-Cl | 2,4-(Cl)₂ | HNO₃ | 164.2° |
| 2,4-(Cl)₂ | 2-Cl | HNO₃ | 151° |

EXAMPLE LXXV

A mixture of 13.6 parts of imidazole, 18.5 parts of 2-(bromomethyl)-2-(o-chlorophenyl)-4-(p-chlorophenyl)-1,3-dioxolane, 4 parts of sodium iodide and 150 parts of dimethylformamide is stirred and refluxed for 72 hours. Water is added and the product is extracted twice with diisopropylether. The combined extracts are washed twice with water, dried, filtered and evaporated. The residue is purified by column-chromatography over silica gel using trichloromethane as eluent. The pure fractions are collected and the eluent is evaporated. The residue of 1-[2-(o-chlorophenyl)-4-(p-chlorophenyl)-1,3-dioxolan-2-ylmethyl]-imidazole is converted into the nitrate salt in 2-propanol and diisopropylether. The salt is filtered off and crystallized from a mixture of ethanol and diisopropylether, yielding 1-[2-(o-chlorophenyl)-4-(p-chlorophenyl)-1,3-dioxolan-2-ylmethyl]imidazole nitrate; mp. 183.1° C.

EXAMPLE LXXVI

A mixture of 13.6 parts of imidazole, 18.6 parts of 2-(bromomethyl)-4-(p-bromophenyl)-2-(2,4-dichlorophenyl)-1,3-dioxolane, 4 parts of sodium iodide and 150 parts of dimethylformamide is stirred and refluxed for 3 days. The reaction mixture is poured into water and the product is extracted twice with diisopropylether. The combined extracts are washed twice with water, dried, filtered, and evaporated. The residue is purified by column-chromatography over silica gel using chloroform as eluent. The pure fractions are collected and the eluent is evaporated. The residue, 1-[4-(p-bromophenyl)-2-(2,4-dichlorophenyl)-1,3-dioxolan-2-ylmethyl-]imidazole, is converted into the nitrate salt in 2-propanol and diisopropylether. The salt is filtered off and crystallized from a mixture of 2-propanol and diisopropylether, yielding 1-[4-(p-bromophenyl)-2-(2,4-dichlorophenyl)-1,3-dioxolan-2-ylmethyl]imidazole nitrate; mp. 141.9° C.

EXAMPLE LXXVII

A mixture of 13.6 parts of imidazole, 17.5 parts of 2-(bromomethyl)-2-(p-bromophenyl)-4-(o-chlorophenyl)-1,3-dioxolane, 4 parts of sodium iodide and 150 parts of dimethyl formamide is stirred and refluxed for 3 days. Water is added and the product is extracted twice with diisopropylether. The combined extracts containing 1-[2-(p-bromophenyl)-4-(o-chlorophenyl)-1,3-dioxolane-2-ylmethyl]imidazole are washed twice with water and acidified with an excess of a concentrated nitric acid solution. The nitrate salt is filtered off and crystallized from a mixture of ethanol and diisopropylether, yielding 1-[2-(p-bromophenyl)-4-(o-chlorophenyl)-1,3-dioxolan-2-ylmethyl]imidazole nitrate; mp. 194.7° C.

EXAMPLE LXXVIII

Following the procedure of Example LXXVIII and using equivalent amounts of the appropriate starting materials, the following imidazoles and imidazole acid addition salts are prepared:

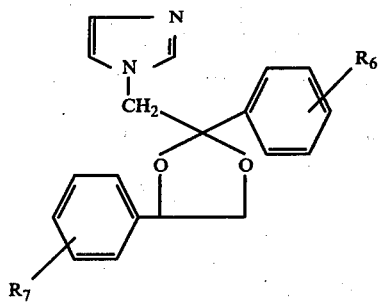

| $R_6$ | $R_7$ | Acid Salt | Melting Point of Salt |
|---|---|---|---|
| 2,4-(Cl)$_2$ | 2,4-(Cl)$_2$ | HNO$_3$ | 161.2° |
| 4-Br | — | HNO$_3$ | 156.5° |
| — | 4-Br | HNO$_3$ | 131.1° |
| 4-CH$_3$ | 2,4-(Cl)$_2$ | HNO$_3$ | 193.6° |
| 4-Br | 4-Br | HNO$_3$ | 144.3° |
| 4-CH$_3$ | 4-Cl | HNO$_3$ | 200.8° |
| 4-Cl | 4-Br | HNO$_3$ | 145.2° |
| 4-CH$_3$ | 4-Br | HNO$_3$ | 210.5° |
| 3-Cl | 2,4-(Cl)$_2$ | HNO$_3$ | 165.4° |
| 2-Cl | 4-Br | HNO$_3$ | 184.1° |
| 4-CH$_3$ | 2-Cl | HNO$_3$ | 207.5° |
| 4-Cl | 4-CH$_3$ | HNO$_3$ | 144.3° |
| 4-Br | 4-CH$_3$ | HNO$_3$ | 140.2° |
| 4-Cl | 4-F | HNO$_3$ | 163.2° |
| 4-Br | 4-F | HNO$_3$ | 179.3° |

EXAMPLE LXXIX

To a stirred solution of 2.3 parts of sodium in 80 parts of methanol are added 6.8 parts of imidazole, followed by the addition of 100 parts of dimethyl formamide and the methanol is removed at atmospheric pressure till an internal temperature of 130° C. is reached. Then there are added 7 parts A-2-(bromomethyl)-2-(p-chlorophenyl)-4-(4-chloro-o-tolyloxymethyl)-1,3-dioxolane and the mixture is stirred and refluxed for 3 hours. The reaction mixture is poured into water and the product is extracted with benzene. The extract is dried and evaporated in vacuo. The residue of A-1-[2-(p-chlorophenyl)-4-(4-chloro-o-tolyloxymethyl)-1,3-dioxolan-2-ylmethyl-]imidazole is converted into the nitrate salt in 2-propanol. Upon the addition of diisopropylether, the salt is precipitated. It is filtered off and crystallized from a mixture of methanol and diisopropylether, yielding cis 1-[2-(p-chlorophenyl)-4-(4-chloro-o-tolyloxymethyl)-1,3-dioxolan-2-ylmethyl]imidazole nitrate; mp. 164.3° C.

EXAMPLE LXXX

Following the procedure of Example LXXIX and using equivalent amounts of the appropriate starting materials, the following imidazoles and imidazole acid addition salts are prepared:

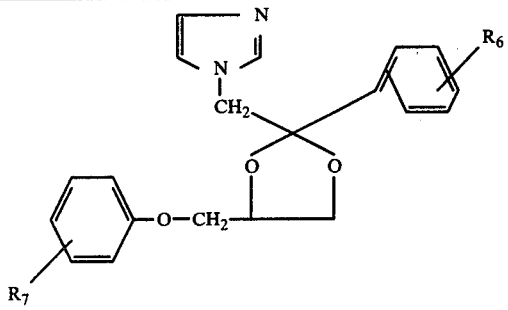

| Isomer | R$_6$ | R$_7$ | Acid Salt | Melting Point of Salt |
|---|---|---|---|---|
| trans | 4-Cl | 4-Cl,2-CH$_3$ | HNO$_3$ | 190 – 190.7° |
| cis | 4-Cl | 4-CH$_3$ | HNO$_3$ | 140.2° |
| trans | 4-Cl | 4-CH$_3$ | HNO$_3$ | 160° |
| trans | 4-Cl | 4-Cl | HNO$_3$ | 171.8 – 176.9° |
| cis | 4-Cl | 4-Cl | HNO$_3$ | 165.8 – 169.6° |
| B | 4-Cl | 2,4-Cl | HNO$_3$ | 160 – 165.3° |
| cis | 4-Cl | 4-F | HNO$_3$ | 172.3 – 174.5° |
| trans | 4-Cl | 4-F | HNO$_3$ | 175.9° |
| A | 4-Cl | 2-CH$_3$ | HNO$_3$ | 134.6 – 145.4° |
| B | 4-Cl | 2-CH$_3$ | HNO$_3$ | 156.6 – 161.6° |
| B | 4-Cl | 2-Cl | HNO$_3$ | 170.5° |
| B | 4-Cl | 4-OCH$_3$ | HNO$_3$ | 133.2° |

EXAMPLE LXXXI

To a stirred solution of 2.3 parts of sodium in 80 parts of methanol are added 6.8 parts of imidazole, 150 parts of dimethylformamide and 2 parts of sodium iodide at room temperature. The methanol is removed at atmospheric pressue till an internal temperature of 130° C. is reached. Then there are added 8 parts of A-2-(bromomethyl)-2-(p-chlorophenyl)-4-(2,4-dichlorophenoxymethyl)-1,3-dioxolane and the whole is stirred and refluxed for 2 hours. The reaction mixture is allowed to cool to room temperature and water is added (400 parts). The reaction mixture is diluted with 80 parts of diisopropylether, whereupon the product is crystallized. It is filtered off and recrystallized from 4-methyl-2-pentanone, yielding A-1-[2-(p-chlorophenyl)-4-(2,4-dichlorophenoxymethyl)-1,3-dioxolane-2-ylmethyl]imidazole; mp. 175.4°–179.5° C.

EXAMPLE LXXXII

Following the procedure of Example LXXXI but substituting for the A-2-(bromomethyl)-2-(p-chlorophenyl)-4-(2,4-dichlorophenoxymethyl)-1,3-dioxolane used therein equivalent amounts of A-2-(bromomethyl)-4-(o-chlorophenoxymethyl)-2-(p-chlorophenyl)-1,3-dioxolane and A-2-(bromomethyl)-2-(p-chlorophenyl)-4-(p-methoxyphenoxymethyl)-1,3-dioxolane there are prepared A-1-[4-(o-chlorophenoxymethyl)-2-(p-chlorophenyl)-1,3-dioxolan-2-ylmethyl[imidazole (mp. 140.8°–143.6°) and A-1-[2-p-chlorophenyl)-4-(p-methoxyphenoxymethyl)-1,3-dioxolan-2-ylmethyl]imidazole (mp. 111.1°).

EXAMPLE LXXXIII

To a stirred solution of 4.6 parts of sodium in 160 parts of methanol are added successively 13.6 parts of imidazole, 300 parts of dimethylformamide and 4 parts of sodium iodide. The methanol is distilled off at atmospheric pressure till an internal temperature of 130° C. is reached. Then there are added 25.9 parts of A + B-2-(bromomethyl)-2-(p-chlorophenyl)-4-(2,6-dichlorophenoxymethyl)-1,3-dioxolane and the whole is stirred at reflux temperature for 2 hours. The reaction mixture is allowed to cool to room temperature and poured onto water. The product is extracted twice with benzene. The combined extracts are washed twice with water, dried and evaporated in vacuo. The residue, containing the "A" and "B"-isomers, is chromatographed over silica gel with chloroform as eluent. The "A"-isomer is collected as an oily free base and is converted into the nitrate salt in 2-propanol. The crude salt is crystallized from 2-propanol, yielding 3.8 parts of A-1-[2-(p-chlorophenyl)-4-(2,6-dichlorophenoxymethyl)-1,3-dioxolan-2-ylmethyl]imidazole nitrate; mp. 145.8° C. The "B"-isomer is also collected as an oily free base and is converted into the nitrate salt in 2-propanol and diisopropylether. The crude salt is crystallized from 2-propanol, yielding 2.2 parts of B-1-[2-(p-chlorophenyl)-4-(2,6-dichlorophenoxymethyl)-1,3-dioxolan-2-ylmethyl]imidazole nitrate; mp. 197°–200.5° C.

EXAMPLE LXXXIV

To a stirred solution of 4.6 parts of sodium in 120 parts of methanol are added successively 13.6 parts of imidazole, 200 parts of dimethylformamide and 2 parts of sodium iodide. The methanol is removed at atmospheric pressure, while stirring, till an internal temperature of 130° C. is reached. Then there are added 21.5 parts of A + B-2-(bromomethyl)-2-(2,4-dichlorophenyl)-4-(o-tolyloxymethyl)-1,3-dioxolane and the whole is stirred and refluxed for 2 hours. The reaction mixture is allowed to cool to room temperature and poured onto water. The product is extracted with benzene (twice). The extracts are washed twice with water, dried, filtered and removed in vacuo. The residue is chromatographed over silica gel with chloroform as eluent. The "A"-isomer is collected and the eluent is evaporated. The free base residue is converted into the nitrate salt in 4-methyl-2-pentanone. Upon the addition of diisopropylether, the nitrate salt is precipitated. It is filtered off and crystallized from 4-methyl-2-pentanone, yielding A-1-[2-(2,4-dichlorophenyl)-4-(o-tolyloxymethyl)-1,3-dioxolan-2-ylmethyl]imidazole nitrate.; mp. 156.2° C.

The "B"-isomer is collected too and the eluent is evaporated. The free base residue is converted into the oxalate salt in 4-methyl-2-pentanone and diisopropylether. The crude salt is filtered off and crystallized from 4-methyl-2-pentanone, yielding B-1-[2-(2,4-dichlorophenyl)-4-(o-tolyloxymethyl)-1,3-dioxolan-2-ylmethyl]imidazole sesquioxalate; mp. 138.5° C.

EXAMPLE LXXXV

A mixture of 6.8 parts of imidazole, 8.5 parts of B-2-(bromomethyl)-4-(p-chlorophenoxymethyl)-2-(2,4-dichlorophenyl)-1,3-dioxolane, 2 parts of sodium iodide and 100 parts of dimethylformamide is stirred and refluxed for 36 hours. The reaction mixture is allowed to cool to room temperature and poured into water. The product is extracted twice with benzene. The combined organic layers are washed twice with water, dried and the solvent is removed in vacuo. The residue is purified by column-chromatography over silica gel using chloroform as eluent. The pure fractions are collected and the eluent is evaporated. The residue is B-1-[4-(p-chlorophenoxymethyl)-2-(2,4-dichlorophenyl)-1,3-dioxolan-2-ylmethyl]imidazole is converted into the oxalate salt in 4-methyl-2-pentanone: upon the addition of diisopropylether, the salt is precipitated. It is filtered off and crystallized from 4-methyl-2-pentanone, yielding 3.1 parts of trans-1-[4-p-chlorophenoxymethyl)-2-(2,4-dichlorophenyl)-1,3-dioxolan-2-ylmethyl-]imidazole sesquioxalate; mp. 101° C.

EXAMPLE LXXXVI

A mixture of 6.8 parts of imidazole, 8.9 parts of B-2-(bromomethyl)-4-(2,4-dichlorophenoxymethyl)-2-(2,4-dichlorophenyl)-1,3-dioxolane, 3 parts of sodium iodide and 100 parts of dimethyl formamide is stirred and refluxed for 48 hours. The reaction mixture is allowed to cool to room temperature and poured into water. The product is extracted twice with benzene. The combined extracts are washed twice with water and the solvent is removed in vacuo. The residue is purified by column-chromatography over silica gel, using chloroform as eluent. The pure fractions are collected and the eluent is evaporated. The residue of B-1-[4-(2,4-dichlorophenoxymethyl)-2-(2,4-dichlorophenyl)-1,3-dioxolan-2-ylmethyl]imidazole is converted into the oxalate salt in 4-methyl-2-pentanone: upon the addition of diisopropylether, the salt is precipitated. It is filtered off and crystallized twice from 4-methyl-2-pentanone, yielding B-1-[4-(2,4-dichlorophenoxymethyl)-2-(2,4-dichlorophenyl)-1,3-dioxolan-2-ylmethyl]imidazole sesquioxalate; mp. 121.2° C.

EXAMPLE LXXXVII

A mixture of 6.8 parts of imidazole, 7.8 parts of A-2-(bromomethyl)-2-(2,4-dichlorophenyl)-4-(phenoxymethyl)-1,3-dioxolane, 4 parts of sodium iodide and 150 parts of dimethylformamide is stirred and refluxed for 3 days. The reaction mixture is allowed to cool to room temperature, poured into water and the product is extracted twice with diisopropylether. The combined extracts containing A-1-[2-(2,4-dichlorophenyl)-4-(phenoxymethyl)-1,3-dioxolan-2-ylmethyl]imidazole are washed twice with water and acidified with an excess of a concentrated nitric acid solution. The salt is filtered off and crystallized from a mixture of ethanol and diisopropylether, yielding 5.6 parts of A-1-[2-(2,4-dichlorophenyl)-4-(phenoxymethyl)-1,3-dioxolan-2-ylmethyl]imidazole nitrate; mp. 180.5° C.

EXAMPLE LXXXVIII

Following the procedure of Example LXXXVII and using equivalent amounts of the appropriate starting materials, the following imidazoles and imidazole acid addition salts are prepared:

| Isomer | $R_6$ | $R_7$ | Acid Salt | Melting Point Of Salt |
|---|---|---|---|---|
| A | 2,4-$(Cl)_2$ | 3,4-$(Cl)_2$ | $HNO_3$ | 152.1° |
| A | 2,4-$(Cl)_2$ | 3-Cl | $HNO_3$ | 120.9° |
| A + B | 2,4-$(Cl)_2$ | 4-Cl,2-$CH_3$ | $HNO_3$ | 121.9° |
| A | 2,4-$(Cl)_2$ | 2,4-$(Br)_2$ | $HNO_3$ | 164.9° |
| cis | 2,4-$(Cl)_2$ | 2-F | $HNO_3$ | 135.6° |
| A | H | 4-Br | $HNO_3$ | 167.6° |
| B | 2,4-$(Cl)_2$ | 4-Br | $HNO_3$ | 31.1° |

EXAMPLE LXXXIX

A mixture of 6.8 parts of imidazole, 5 parts of A-2-(bromomethyl)-2-(2,4-dichlorophenyl)-4-(p-fluorophenoxymethyl)-1,3-dioxolane, 2 parts of sodium iodide and 50 parts of dimethylformamide is stirred and refluxed for 24 hours. The reaction mixture is allowed to cool to room temperature and then poured into water. The product is extracted twice with benzene. The combined organic phases are washed twice with water, dried, filtered, and evaporated in vacuo. The residue is A-1-[2-(2,4-dichlorophenyl)-4-(p-fluorophenoxymethyl)-1,3-dioxolan-2-ylmethyl]imidazole is converted into the nitrate salt in 2-propanol. The crude salt is filtered off and crystallized from 2-propanol, yielding 3.2 parts of cis-1-[2-(2,4-dichlorophenyl)-4-(p-fluorophenoxymethyl)-1,3-dioxolan-2-ylmethyl]imidazole nitrate; mp. 151°-152° C.

EXAMPLE XC

Following the procedure of Example LXXXIX and using equivalent amounts of the appropriate starting materials, the following imidazoles and imidazole acid addition salts are prepared:

| Isomer | $R_6$ | $R_7$ | Acid Salt | Melting Point of Salt |
|---|---|---|---|---|
| A | 2,4-$(Cl)_2$ | 4-$CH_3$ | $HNO_3$ | 141.8° |

-continued

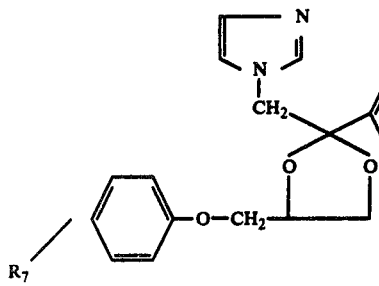

| Isomer | R_6 | R_7 | Acid Salt | Melting Point of Salt |
|---|---|---|---|---|
| B | 2,4-(Cl)_2 | 4-CH_3 | (COOH)_2 | 145.1° |
| cis | 2,4-(Cl)_2 | 4-OCH_3 | (COOH)_2 | 184.7° |
| cis | 2,4-(Cl)_2 | 4-Cl | HNO_3 | 152.7° |
| A | 2,4-(Cl)_2 | 2,4-(Cl)_2 | HNO_3 | 146.5° |
| A | 2,4-(Cl)_2 | 4-Br | HNO_3 | 158.9° |
| A | 2,4-(Cl)_2 | 4-Cl,3,5-CH_3 | HNO_3 | 185.7° |
| A | 2,4-(Cl)_2 | 4-CN | HNO_3 | 208° |
| A | 2,4-(Cl)_2 | 2-OCH_3 | 2(COOH)_2 | 110.6° |

EXAMPLE XCI

A mixture of 13.6 parts of imidazole, 22.2 parts of A + B-2-(bromomethyl)-4-(o-chlorophenoxymethyl)-2-(2,4-dichlorophenyl)-1,3-dioxolane, 4 parts of potassium iodide, and 150 parts of dimethylformamide is stirred and refluxed for 3 days. The reaction mixture is allowed to cool to room temperature, poured into water and the product is extracted twice with diisopropylether. The combined extracts are washed twice with water, dried, filtered and evaporated. The residue is purified by column-chromatography over silica gel using chloroform as eluent, yielding two fractions.

The first fraction is evaporated and the residue of A-1-[4-(o-chlorophenoxymethyl)-2-(2,4-dichlorophenyl)-1,3-dioxolan-2-ylmethyl]imidazole is dissolved in a mixture of 4-methyl-2-pentanone and diisopropylether. The solution is acidified with an excess of a concentrated nitric acid solution. The nitrate salt is filtered off and crystallized from a mixture of 4-methyl-2-pentanone and diisopropylether, yielding A-1-[4-(o-chlorophenoxymethyl)-2-(2,4-dichlorophenyl)-1,3-dioxolan-2-ylmethyl]imidazole nitrate; mp. 136.2° C.

The second fraction is evaporated and the residue of B-1-[4-(o-chlorophenoxymethyl)-2-(2,4-dichlorophenyl)-1,3-dioxolan-2-ylmethyl]imidazole is dissolved in a mixture of 4-methyl-2-pentanone and diisopropylether. The solution is acidified with an excess of oxalic acid. The oxalate salt is filtered off and crystallized from 4-methyl-2-pentanone, yielding 4 parts of B-1-[4-(o-chlorophenoxymethyl)-2-(2,4-dichlorophenyl)-1,3-dioxolan-2-ylmethyl]imidazole dioxalate; mp. 103.5° C.

EXAMPLE XCII

Following the procedure of Example XCI and using equivalent amounts of the appropriate starting materials, the following imidazoles and imidazole acid addition salts are prepared. Where only one isomer is listed, no second fraction was obtained from chromatography.

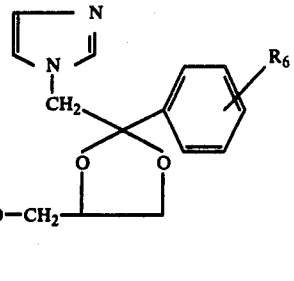

| Isomer | R_6 | R_7 | Acid Salt | Melting Point of Salt |
|---|---|---|---|---|
| A | 2,4-(Cl)_2 | 2,6-(Cl)_2 | HNO_3 | 159° |
| cis | 2,4-(Cl)_2 | 2-Br | HNO_3 | 142.2° |
| trans | 2,4-(Cl)_2 | 2-Br | 2(COOCH)_2 | 151.3° |
| A | 2,4-(Cl)_2 | 2,5-(CH_3)_2 | HNO_3 | 180.9° |
| B | 2,4-(Cl)_2 | 2,5-(CH_3)_2 | 1.5(COOH)_2 | 142.7° |
| A | 2,4-(Cl)_2 | 2,4,6-(Cl)_3 | HNO_3 | 181.6° |
| B | 2,4-(Cl)_2 | 2,4,6-(Cl)_3 | 2(COOH)_2 | 143.9° |
| A | 2,4-(Cl)_2 | 2-Cl,4-C(CH_3)_3 | HNO_3 | 141.2° |
| B | 2,4-(Cl)_2 | 2-Cl,4-C(CH_3)_3 | HNO_3 | 141.1° |
| A | 2,4-(Cl)_2 | 2,4,5-(Cl)_3 | HNO_3 | 196.1° |
| B | 2,4-(Cl)_2 | 2,4,5-(Cl)_3 | 1.5(COOH)_2 | 173.6° |
| cis | 2,4-(Cl)_2 | 2,5-(Br)_2, 4-CH_3 | HNO_3 | 175.4° |
| A | 2,4-(Cl)_2 | 2OC_2H_5 | HNO_3 | 117.7° |
| A + B | 2-Cl | 4-Br | HNO_3 | 145.3° |
| B | 2-Cl | 4-Br | HNO_3 | 152.7° |
| A | 2-Br | 4-Br | HNO_3 | 149.9° |
| B | 2-Br | 4-Br | HNO_3 | 169.3° |
| A | 2,4-(Cl)_2 | 2-Cl,6-CH_3 | HNO_3 | 154.2° |

EXAMPLE XCIII

A mixture of 13.6 parts of imidazole, 12 parts of A 2-(bromomethyl)-4-(6-bromo-2-naphthyloxymethyl)-2-(2,4-dichlorophenyl)-1,3-dioxolane, 4 parts of potassium iodide and 150 parts of dimethylformamide is stirred and refluxed for 3 days. The reaction mixture is allowed to cool to room temperature, poured into water and the product is extracted twice with benzene. The combined extracts are washed twice with water, dried, filtered and evaporated. The residue of A-1-[4-(6-bromo-2-naphthyloxymethyl)-2-(2,4-dichlorophenyl)-1,3-dioxolan-2-ylmethyl]imidazole is converted into the nitrate salt in 4-methyl-2-pentanone and diisopropylether. The salt is filtered off and crystallized from a mixture of methanol and diisopropylether, yielding A 1-[4-(6-bromo-2-naphthyloxymethyl)-2-(2,4-dichlorophenyl)-1,3-dioxolan-2-ylmethyl]imidazole nitrate; mp. 195.5° C.

EXAMPLE XCIV

A mixture of 6.8 parts of 1H-imidazole, 6 parts of A 2-(bromomethyl)-2-(2,4-dichlorophenyl)-4-[(2-naphthalenyloxy)methyl]-1,3-dioxolane, 4 parts of potassium iodide and 150 parts of N,N-dimethylformamide is stirred and refluxed for 3 days. The reaction mixture is poured into water and the product is extracted twice with 1,1'-oxybisethane. The combined extracts containing A-1-[2-(2,4-dichlorophenyl)-4-(2-naphthalenyloxymethyl)-1,3-dioxolan-2-ylmethyl]-1H-imidazole are washed twice with water and acidified with an excess of a concentrated nitric acid solution. The nitrate salt is filtered off and crystallized from a mixture of ethanol and 2,2'-oxybispropane, yielding cis-1-[2-(2,4-dichlorophenyl)-4-(2-naphthalenyloxymethyl)-1,3-dioxolan-2-ylmethyl]-1H-imidazole nitrate; mp. 156.3° C.

EXAMPLE XCV

A mixture of 9.7 parts of 1H-imidazole, 12.5 parts of A + B 2-(bromomethyl)-4-(4-bromophenoxymethyl)-2-(4-methylphenyl)-1,3-dioxolane, 3 parts of potassium iodide and 135 parts of N,N-dimethylformamide is stirred and refluxed for 72 hours. The reaction mixture is poured into water and the product is extracted twice with 1,1'-oxybisethane. The extract containing A-1-[4-(4-bromophenoxymethyl)-2-(4-methylphenyl)-1,3-dioxolan-2-ylmethyl]-1H-imidazole is washed twice with water, and an excess of a concentrated nitric acid solution and 2,2'-oxybispropane are added. The formed salt is filtered off and crystallized from a mixture of ethanol and 2,2'-oxybispropane, yielding 5.6 parts of A 1-[4-(4-bromophenoxymethyl)-2-(4-methylphenyl)-1,3-dioxolan-2-ylmethyl]-1H-imidazole nitrate; mp. 175.5° C.

EXAMPLE XCVI

Following the procedure of Example XCV but substituting for the A+B-2-(bromomethyl)-4-(4-bromophenoxymethyl)-2-(4-methylphenyl)-1,3-dioxolane used therein equivalent amounts of A+B-2-(bromomethyl)-4-(4-bromophenoxymethyl)-2-(4-chlorophenyl)-1,3-dioxolane and A+B-2-(bromomethyl)-4-(4-bromophenoxymethyl)-2-(4-bromophenyl)-1,3-dioxolane there are prepared A-1-[4-(4-bromophenoxymethyl)-2-(4-chlorophenyl)-1,3-dioxolan-2-ylmethyl]-1H-imidazole and its nitrate salt (mp. 158°) and A-1-[4-(4-bromophenoxymethyl)-2-(4-bromophenyl)-1,3-dioxolan-2-ylmethyl]-1H-imidazole and its nitrate salt (mp. 170.8°).

EXAMPLE XCVII

A mixture of 20.8 parts of 1H-imidazole, 21 parts of A + B 2-(bromomethyl)-4-(4-chloro-1-naphthalenyloxymethyl)-2-(2,4-dichlorophenyl)-1,3-dioxolane, 4 parts of potassium iodide and 135 parts of N,N-dimethylformamide is stirred and refluxed for 3 days. The reaction mixture is poured into water and the product is extracted twice with 2,2'-oxybispropane. The combined extracts containing A + B 1-[4-(4-chloro-1-naphthalenyloxymethyl)-2-(2,4-dichlorophenyl)-1,3-dioxolan-2-ylmethyl]-1H-imidazole are washed twice with water and an excess of a concentrated nitric acid solution is added. The nitrate salt is filtered off and crystallized from a mixture of ethanol and 2,2'-oxybispropane, yielding A + B 1-[4-(4-chloro-1-naphthalenyloxymethyl)-2-(2,4-dichlorophenyl)-1,3-dioxolan-2-ylmethyl]-1H-imidazole nitrate; mp. 136.7° C.

EXAMPLE XCVIII

A mixture of 20.4 parts of 1H-imidazole, 27.2 parts of A + B 2-(bromomethyl)-4-(4-bromophenylthiomethyl)-2(2,4-dichlorophenyl)-1,3-dioxolane, 4 parts of potassium iodide and 180 parts of N,N-dimethylformamide is stirred and refluxed for 3 days. The reaction mixture is poured into water and the product is extracted twice with 1,1'-oxybisethane. The combined extracts are washed twice with water, dried, filtered and evaporated. The residue is purified by column-chromatography over silica gel using trichloromethane as eluent. The pure fractions are collected and the eluent is evaporated. The residue of A +B-1-[4-(4-bromophenylthiomethyl)-2-(2,4-dichlorophenyl)-1,3-dioxolan-2-ylmethyl]-1H-imidazole is converted into the nitrate salt in 4-methyl-2-pentanone and 2,2'-oxybispropane. The salt is filtered off and crystallized from a mixture of ethanol and 2,2'-oxybispropane. The product is filtered off and dried, yielding A + B 1-[4-(4-bromophenylthiomethyl)-2-(2,4-dichlorophenyl)-1,3-dioxolan-2-ylmethyl]-1H-imidazole nitrate; mp. 170.0° C.

EXAMPLE IC

A mixture of 20.4 parts of 1H-imidazole, 20.5 parts of A + B 2-(bromomethyl)-2-(2,4-dichlorophenyl)-4-(phenylthiomethyl)-1,3-dioxolane, 4 parts of potassium iodide and 135 parts of N,N-dimethylformamide is stirred and refluxed for 3 days. The reaction mixture is poured into water and the product is extracted twice with 1,1'-oxybisethane. The combined extracts are washed twice with water, dried, filtered and evaporated. The residue is purified by column-chromatography over silica gel using trichloromethane as eluent. The pure fractions are collected and the eluent is evaporated. The residue of A + B 1-[2-(2,4-dichlorophenyl)-4-(phenylthiomethyl)-1,3-dioxolane-2-ylmethyl]-1H-imidazole is converted into the nitrate salt in 4-methyl-2-pentanone and 2,2'-oxybispropane. The salt is filtered off and crystallized from a mixture of ethanol and 2,2'-oxybispropane. The product is filtered off and dried, yielding A + B 1-[2-(2,4-dichlorophenyl)-4-(phenylthiomethyl)-1,3-dioxolane-2-ylmethyl]-1H-imidazole nitrate; mp. 122.3° C.

EXAMPLE C

A mixture of 7.9 parts of 1H-imidazole, 11.5 parts of A + B 2-(bromomethyl)-2-(2,4-dichlorophenyl)-4-(4-phenylphenoxymethyl)-1,3-dioxolane, 4 parts of potassium iodide and 135 parts of N,N-dimethylformamide is stirred and refluxed for 3 days. The reaction mixture is poured onto water and the product is extracted twice with 1,1'-oxybisethane. The combined extracts are washed with water, dried, filtered and evaporated. The residue is purified by column-chromatography over silica gel, using trichloromethane as eluent.

The first fraction is collected and the eluent is evaporated. The residue is converted into the nitrate salt in 4-methyl-2-pentanone and 2,2'-oxybispropane. The salt is filtered off and crystallized from a mixture of ethanol and 2,2'-oxybispropane, yielding A + B 1-[2-(2,4-dichlorophenyl)-4-(4-phenylphenoxymethyl)-1,3-dioxolan-2-ylmethyl]-1H-imidazole nitrate; mp. 187.9° C.

The second fraction is collected and the eluent is evaporated. The residue is crystallized from 4-methyl-2-pentanone, yielding trans-1-[2-(2,4-dichlorophenyl)-4-(4-phenylphenoxymethyl)-1,3-dioxolan-2-ylmethyl]-1H-imidazole; mp. 155.7° C.

EXAMPLE CI

To a stirred sodium methoxide solution, prepared starting from 2.3 parts of sodium in 48 parts of methanol, is added a mixture of 6.8 parts of 1H-imidazole and 180 parts of N,N-dimethylformamide. The methanol is distilled off at normal pressure till an internal temperature of 125° C. is reached. Then there are added 22.8 parts of A + B 2-(bromomethyl)-2-(2,4-dichlorophenyl)-4-(2,6-dimethylphenoxymethyl)-1,3-dioxolane and 3 parts of potassium iodide. The whole is stirred and refluxed for 24 hours. The reaction mixture is poured onto water and the product is extracted three times with 1,1'-oxybisethane. The combined extracts are washed twice with water, dried, filtered and evaporated. The residue is purified by column-chromatography over silica gel using trichloromethane as eluent.

The first fraction (A-isomer) is collected and the eluent is evaporated. The residue is converted into the nitrate salt in 4-methyl-2-pentanone and 2,2'-oxybispropane. The salt is filtered off and crystallized from a mixture of ethanol and 2,2'-oxybispropane, yielding A-1-[2-(2,4-dichlorophenyl)-4-(2,6-dimethylphenoxymethyl)-1,3-dioxolan-2-ylmethyl]-1H-imidazole nitrate; mp. 155.6° C.

The second fraction (B-isomer) is collected and the eluent is evaporated. The residue is converted into the nitrate salt in 4-methyl-2-pentanone and 2,2'-oxybispropane. The salt is filtered off and crystallized from a mixture of 2-propanol and 2,2'-oxybispropane, yielding A + B 1-[2-(2,4-dichlorophenyl)-4-(2,6-dimethylphenoxymethyl)-1,3-dioxolan-2-ylmethyl]-1H-imidazole nitrate; mp. 134.5° C.

EXAMPLE CII

A mixture of 8.6 parts of 1H-imidazole, 11.3 parts of A-2-(bromomethyl)-2-(2,4-dichlorophenyl)-4-(3,5-dimethylphenoxymethyl)-1,3-dioxolane, 4 parts of potassium iodide and 135 parts of N,N-dimethylacetamide is stirred and refluxed for 3 days. The reaction mixture is poured onto water and the product is extracted twice with 2,2'-oxybispropane. The combined extracts are washed twice with water and an excess of a concentrated nitric acid solution is added. The formed nitrate salt is filtered off and crystallized from a mixture of 2-propanol and 2,2'-oxybispropane. The product is filtered off again and recrystallized from 4-methyl-2-pentanone, yielding A-1-[2-(2,4-dichlorophenyl)-4-(3,5-dimethylphenoxymethyl)-1,3-dioxolan-2-ylmethyl]-1H-imidazole nitrate hydrate; mp. 122.6° C.

EXAMPLE CIII

A mixture of 5.4 parts of 1H-imidazole, 7.5 parts of A + B-2-(bromomethyl)-2-(2,4-dichlorophenyl)-4-[4-(1-methylethyl)-phenoxymethyl]-1,3-dioxolane, 3 parts of potassium iodide and 135 parts of N,N-dimethylacetamide is stirred and refluxed for 3 days. The reaction mixture is allowed to cool to room temperature, poured onto water and the product is extracted twice with 2,2'-oxybispropane. The combined extracts are washed twice with water and an excess of a concentrated nitric acid solution is added. The formed nitrate salt is filtered off and crystallized from a mixture of 2-propanol and 2,2'-oxybispropane, yielding A + B-1-{2-(2,4-dichlorophenyl)-4-[4-(1-methylethyl)phenoxymethyl]-1,3-dioxolan-2-ylmethyl}-1H-imidazole nitrate.

EXAMPLE CIV

Following the procedure of Example CIII and using equivalent amounts of the appropriate starting materials, the following imidazoles and imidazole acid addition salts were prepared:

A-1-{2-(2,4-dichlorophenyl)-4-[4-(1,1-dimethylethyl)-phenoxymethyl]-1,3-dioxolan-2-ylmethyl}-1H-imidazole nitrate; mp. 169.5° C.

A-1-[4-(3,5-dichlorophenoxymethyl)-2-(2,4-dichlorophenyl)-1,3-dioxolan-2-ylmethyl]-1H-imidazole nitrate hydrate; mp. 136.7° C.; and A-1-[4-(4-chloro-3-methylphenoxymethyl)-2-(2,4-dichlorophenyl)-1,3-dioxolan-2-ylmethyl]-1H-imidazole nitrate; mp. 142.8° C.

EXAMPLE CV

A mixture of 6.8 parts of 1H-imidazole, 8 parts of A-2-(bromomethyl)-4-(p-bromophenoxymethyl)-2-(2,4-dichlorophenyl)-1,3-dioxolane, 3 parts of sodium iodide and 90 parts of N,N-dimethylformamide is stirred and refluxed for 3 days. The reaction mixture is cooled and poured onto 500 parts of water. The product is extracted twice with 180 parts of methylbenzene. The combined extracts are washed twice with 200 parts of water, dried, filtered and evaporated. The residue is taken up in a mixture of methanol and 2,2'-oxybispropane, treated with activated charcoal and evaporated. The residue is converted into the nitrate salt in 4-methyl-2-pentanone. The salt is sucked off and the free base is liberated in the conventional manner. It is extracted with methylbenzene and the extract is dried, filtered and evaporated. The residue is triturated in 2,2'-oxybispropane. The product is filtered off and dried, yielding cis-1-[4-(4-bromophenoxymethyl)-2-(2,4-dichlorophenyl)-1,3-dioxolan-2-ylmethyl]-1H-imidazole; mp. 121.8° C.

EXAMPLE CVI

Following the procedure of Example CV and using equivalent amounts of the appropriate starting materials, the following imidazoles and imidazole acid additions salts are prepared:

1-{4-[2-(2-chlorophenyl)ethyl]-2-(2,4-dichlorophenyl)-1,3-dioxolan-2-ylmethyl}-1H-imidazole nitrate; mp. 98.8° C.;

1-{2-(2,4-dichlorophenyl)-4-[2-(2,4-dichlorophenyl)ethyl]-1,3-dioxolan-2-ylmethyl}-1H-imidazole nitrate; mp. 158.1° C.; and A + B 1-{2-(2,4-dichlorophenyl)-4-[2-(2,6-dichlorophenyl)ethyl]-1,3-dioxolan-2-ylmethyl}-1H-imidazole nitrate; mp. 140.1° C.

EXAMPLE CVII

A mixture of 14.4 parts of 1H-imidazole, 18.5 parts of A + B 2-(bromomethyl)-2-(2,4-dichlorophenyl)-4-[2-(4-methoxyphenyl)ethyl]-1,3-dioxolane, 5 parts of potassium iodide and 135 parts of N,N-dimethylacetamide is stirred and refluxed for 2 days. The reaction mixture is allowed to cool to room temperature and poured onto water. The product is extracted twice with 2,2'-oxybispropane. The combined extracts are washed with water, dried, filtered and evaporated. The residue is converted into the ethanedioate salt in 4-methyl-2-pentanone and 2,2'-oxybispropane. The salt is filtered off and crystallized from a mixture of 2,2'-oxybispropane and ethanol, yielding A + B 1-{2-(2,4-dichlorophenyl)-4-[2-(4-methoxyphenyl)ethyl]-1,3-dioxolan-2-ylmethyl}-1H-imidazole sesquiethanedioate; mp. 130.7° C.

EXAMPLE CVIII

Following the procedure of Example CVII and using equivalent amounts of the appropriate starting materials, the following imidazoles and imidazole acid addition salts are prepared:

1-{4-[2-(4-chlorophenyl)ethyl]-2-(2,4-dichlorophenyl)-1,3-dioxolan-2-ylmethyl}-1H-imidazole diethanedioate; mp. 131.9° C.;

1-[2-(2,4-dichlorophenyl)-4-(2-phenylethyl)-1,3-dioxolan-2-ylmethyl]-1H-imidazole sesquiethanedioate; mp. 117.8° C.; and A + B 1-{2-(2,4-dichlorophenyl)-4-[2-(4-methylphenyl)ethyl]-1,3-dioxolan-2-ylmethyl}-1H-imidazole sesquiethanedioate hydrate; mp. 123.8° C.

EXAMPLE CIX

A mixture of 10.6 parts of 1H-imidazole, 15.8 parts of A-2-(bromomethyl)-4-(4-bromophenoxymethyl)-2-(2,3,4-trichlorophenyl)-1,3-dioxolane, 3 parts of potassium iodide and 135 parts of N,N-dimethylacetamide is stirred and refluxed for 2 days. The reaction mixture is allowed to cool to room temperature and poured onto water. The product is extracted twice with 1,1'-oxybisethane. The combined extracts are washed twice with water and acidified with an excess of a concentrated nitric acid solution. Upon the addition of 2,2'-oxybispropane, the formed nitrate salt is precipitated. It is filtered off and crystallized from a mixture of ethanol and 2,2'-oxybispropane, yielding A-1-[4-(4-bromophenoxymethyl)-2-(2,3,4-trichlorophenyl)-1,3-dioxolan-2-ylmethyl]-1H-imidazole nitrate; mp. 174.4° C.

EXAMPLE CX

A mixture of 17 parts of 1H-imidazole, 33.5 parts of A + B-2-(bromomethyl)-4-(2,3-dichlorophenoxymethyl)-2-(2,4-dichlorophenyl)-1,3-dioxolane, 3 parts of potassium iodide and 135 parts of N,N-dimethylacetamide is stirred and refluxed for 2 days. The reaction mixture is allowed to cool to room temperature and poured onto water. The product is extracted twice with 1,1'-oxybisethane. The combined extracts are washed twice with water, dried, filtered and evaporated. The residue is purified by column-chromatography over silica gel, using trichloromethane as eluent.

The first fraction (A-isomer) is collected and the eluent is evaporated. The residue is converted into the ethanedioate salt in 4-methyl-2-pentanone and 2,2'-oxybispropane. The salt is filtered off and crystallized from 4-methyl-2-pentanone, yielding A-1-[4-(2,3-dichlorophenoxymethyl)-2-(2,4-dichlorophenyl)-1,3-dioxolan-2-ylmethyl]-1H-imidazole diethanedioate; mp. 151.1° C.

The second fraction (B-isomer) is collected and the eluent is evaporated. The residue is converted into the ethanedioate salt in 4-methyl-2-pentanone and 2,2'-oxybispropane. The salt is filtered off and crystallized from 4-methyl-2-pentanone, yielding B-1-[4-(2,3-dichlorophenoxymethyl)-2-(2,4-dichlorophenyl)-1,3-dioxolan-2-ylmethyl]-1H-imidazole sesquiethanedioate; mp. 156.3° C.

EXAMPLE CXI

A mixture of 6.8 parts of 1H-imidazole, 10.2 parts of A-2-(bromomethyl)-4-(2-bromo-4-methylphenoxymethyl)-2-(2,4-dichlorophenyl)-1,3-dioxolane, 3 parts of potassium iodide and 135 parts of N,N-dimethylacetamide is stirred and refluxed for 2 days. The reaction mixture is allowed to cool to room temperature and the product is extracted twice with 1,1'-oxybisethane. The combined extracts are washed twice with water and acidified with a concentrated nitric acid solution. The formed nitrate salt is filtered off and crystallized from a mixture of ethanol and 2,2'-oxybispropane, yielding 5.4 parts of A-1-[4-(2-bromo-4-methylphenoxymethyl)-2-(2,4-dichlorophenyl)-1,3-dioxolan-2-ylmethyl]-1H-imidazole nitrate; mp. 137.1° C.

EXAMPLE CXII

Following the procedure of Example CXI and using an equivalent amount of an appropriate 2-bromomethyl-1,3-dioxolane as a starting material, the following imidazole acid addition salts are obtained:

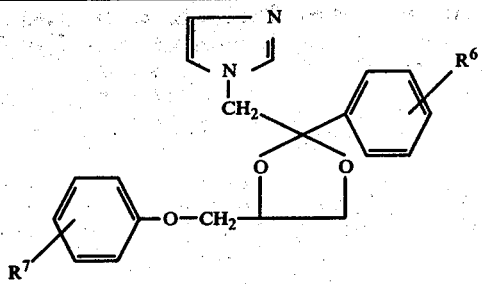

| Isomer | R⁶ | R⁷ | Acid Salt | Melting Point of Salt |
|---|---|---|---|---|
| A | 2-CH₃-4-Cl | 4-Br | HNO₃ | 159.3° C. |
| A=cis | 2-CH₃-4-Br | 4-Br | HNO₃ | 164.3° C. |
| A=cis | 3-Br | 4-Br | HNO₃ | 158.7° C. |
| A=cis | 3-Br-4-CH₃ | 4-Br | HNO₃ | 201.1° C. |
| A=cis | 4-CN | 4-Br | HNO₃ | 190.1° C. |
| A | 2,4-(Cl)₂ | 4-(C₆H₅-CH₂) | HNO₃ · H₂O | 110.3° C. |
| A=cis | 3,5-(Cl)₂ | 4-Br | HNO₃ | 167.1° C. |
| A=cis | 3-NO₂ | 4-Br | HNO₃ | 148.8° C. |
| A=cis | 2,4-(Cl)₂ | 2-NO₂ | 2(COOH)₂ | 95.2° C. |
| B=trans | 2,4-(Cl)₂ | 2-NO₂ | (COOH)₂ | 157.2° C. |
| B=trans | 2,4-(Cl)₂ | 4-(C₆H₅-CH₂) | (COOH)₂ | 137° C. |
| A+B | 2,4-(Cl)₂ | 2-(C₆H₅) | HNO₃ | 109.3° C. |

EXAMPLE CXIII

Following the procedure of Example CXI and using equivalent amounts of the appropriate starting materials and N,N-dimethylformamide as a solvent, there is prepared:

cis-1-[2-(2,4-dichlorophenyl)-4-(2-methoxyphenoxymethyl)-1,3-dioxolan-2-ylmethyl]-1H-imidazole ethanedioate hemihydrate; mp. 123.6° C.

EXAMPLE CXIV

A mixture of 13.6 parts of 1H-imidazole, 10 parts of A-2-(bromomethyl)-2-(2,4-dichlorophenyl)-4-(4-fluorophenoxymethyl)-1,3-dioxolane, 4 parts of sodium iodide and 90 parts of N,N-dimethylformamide is stirred and refluxed for 24 hours. After cooling, the reaction mixture is poured onto ice-water and the product is extracted twice with benzene. The combined extracts are washed with water, dried, filtered and evaporated. The residue is converted into the nitrate salt in 2-propanol. The salt is filtered off and the free base is liberated in the conventional manner. The product is extracted twice with trichloromethane. The extract is washed with water, dried, filtered and evaporated. The oily residue is crystallized from a mixture of benzene and petroleumether, yielding 3.94 parts of cis-1-[2-(2,4-dichlorophenyl)-4-(4-fluorophenoxymethyl)-1,3-dioxolan-2-ylmethyl]-1H-imidazole; mp. 106.7° C.

EXAMPLE CXV

A mixture of 42 parts of 1H-imidazole, 63 parts of A+B-4-([1,1'-biphenyl]-4-yloxymethyl)-2-(bromomethyl)-2-(2,4-dichlorophenyl)-1,3-dioxolane, 20 parts of potassium iodide and 675 parts of N,N-dimethylformamide is stirred and refluxed for 3 days. The reaction mixture is poured onto water and the product is extracted with 2,2'-oxybispropane. The extract is dried, filtered and evaporated. The residue is converted into the nitrate salt in 4-methyl-2-pentanone and 2,2'-oxybispropane. The product is separated as an oil. The supernatant phase is decanted and the residual oil solidifies on triturating in 4-methyl-2-pentanone. The nitrate salt is filtered off and crystallized from ethanol, yielding 5 parts of cis-1-[4-([1,1'-biphenyl]-4-yloxymethyl)-2-(2,4-dichlorophenyl)-1,3-dioxolan-2-ylmethyl]-1H-imidazole nitrate; mp. 186.5° C.

EXAMPLE CXVI

A mixture of 11.5 parts of 1H-imidazole, 17.5 parts of A+B 2-(bromomethyl)-2-(2,4-dichlorophenyl)-4-(3,4,5-trichlorophenoxymethyl)-1,3-dioxolane, 3 parts of potassium iodide and 180 parts of N,N-dimethylacetamide is stirred and refluxed over week-end. The reaction mixture is poured onto water and the product is extracted four times with 1,1'-oxybisethane. The combined extracts are washed a few times with water, dried, filtered and evaporated. The only residue is purified by column-chromatography over silica gel using trichloromethane as eluent. The first fraction (A-isomer) is collected and the eluent is evaporated. The oily residue is converted into the nitrate salt in 4-methyl-2-pentanone. The salt is filtered off and crystallized from a mixture of 4-methyl-2-pentanone and 2,2'-oxybispropane, yielding, after drying, 7.5 parts (40%) of cis-1-[2-(2,4-dichlorophenyl)-4-(3,4,5-trichlorophenoxymethyl)-1,3-dioxolan-2-ylmethyl]-1H-imidazole nitrate.hydrate; mp. 149.9° C. The second fraction (B-isomer) is collected and the eluent is evaporated. The oily residue is converted into the nitrate salt in 4-methyl-2-pentanone. The salt is filtered off and crystallized from a mixture of 4-methyl-2-pentanone and 2,2'-oxybispropane, yielding, after drying, 6.2 parts (27%) of trans-1-[2-(2,4-dichlorophenyl)-4-(3,4,5-trichlorophenoxymethyl)-1,3-dioxolan-2-ylmethyl]-1H-imidazole nitrate; mp. 169.3° C.

EXAMPLE CXVII

Following the procedure of Example CXVI and using equivalent amounts of the appropriate starting materials, the following imidazoles and imidazole acid addition salts are prepared. When only one isomer is listed, no second fraction was obtained from chromatography.
cis-1-[4-(2-chloro-5-methylphenoxymethyl)-2-(2,4-dichlorophenyl)-1,3-dioxolan-2-ylmethyl]-1H-imidazole; mp. 131.7° C.;
trans-1-[4-(2-chloro-5-methylphenoxymethyl)-2-(2,4-dichlorophenyl)-1,3-dioxolan-2-ylmethyl]-1H-imidazole sesquiethanedioate; mp. 148.7° C.; and
A-1-{4-[(1,6-dibromo-2-naphthalenyloxy)methyl]-2-(2,4-dichlorophenyl)-1,3-dioxolan-2-ylmethyl}-1H-imidazole nitrate; mp. 179.4° C.

EXAMPLE CXVIII

A mixture of 4.5 parts of 1H-imidazole, 6.5 parts of A-2-(bromomethyl)-4-(4-bromophenoxymethyl)-2-(2,3-dichlorophenyl)-1,3-dioxolane and 125 parts of N,N-dimethylacetamide is stirred and refluxed for 2 days. The reaction mixture is allowed to cool to room temperature, poured onto water and the product is extracted twice with 1,1'-oxybisethane. The combined extracts are washed twice with water and an excess of a concentrated nitric acid solution is added. The formed nitrate salt is filtered off and crystallized from 4-methyl-2-pentanone, yielding 5 parts (68%) of cis-1-[4-(4-bromophenoxymethyl)-2-(2,3-dichlorophenyl)-1,3-dioxolan-2-ylmethyl]-1H-imidazole nitrate; mp. 138.9° C.

EXAMPLE CXIX

Following the procedure of Example CXVIII and using equivalent amounts of the appropriate starting materials, the following imidazole acid addition salts are prepared:
cis-1-[4-(3-chloro-[1,1'-biphenyl]-4-yloxymethyl)-2-(2,4-dichlorophenyl)-1,3-dioxolan-2-ylmethyl]-1H-imidazole nitrate; mp. 171.1° C.;
cis-1-[4-([1,1'-biphenyl]-4-yloxymethyl)-2-(2-chloro-4-methoxyphenyl)-1,3-dioxolan-2-ylmethyl]-1H-imidazole nitrate; mp. 172.9° C.;
A+B-1-[2-(2,4-dichlorophenyl)-4-(phenylmethyl)-1,3-dioxolan-2-ylmethyl]-1H-imidazole diethanedioate; mp. 117.1° C.;
A+B-1-{2-(2,4-dichlorophenyl)-4-[(4-fluorophenyl)thiomethyl]-1,3-dioxolan-2-ylmethyl}-1H-imidazole diethanedioate; mp. 129.8° C.;
A+B-1-[4-(4-chlorophenylmethyl)-2-(2,4-dichlorophenyl)-1,3-dioxolan-2-ylmethyl]-1H-imidazole sesquiethanedioate; mp. 141.6° C.
A+B-1-[2-(2,4-dichlorophenyl-4-(4-methoxyphenylmethyl)-1,3-dioxolan-2-ylmethyl]-1H-imidazole diethanedioate; mp. 94.2° C.;
cis-2-[2-(2,4-dichlorophenyl)-2-(1H-imidazol-1-ylmethyl)-1,3-dioxolan-4-ylmethoxy]-benzonitrile nitrate; mp. 162.1° C.; and
cis-butyl 4-[2-(2,4-dichlorophenyl)-2-(1H-imidazol-1-ylmethyl)-1,3-dioxolan-4-ylmethoxy]benzoate nitrate; mp. 90.5° C.

EXAMPLE CXX

A mixture of 17 parts of 1H-imidazole, 27.4 parts of A+B-4-([1,1'-bisphenyl]-4-yloxymethyl)-2-(bromomethyl)-2-(3,4,5-trichlorophenyl)-1,3-dioxolane and 135 parts of N,N-dimethylacetamide is stirred and refluxed for 5 days. The reaction mixture is cooled and poured onto water. The product is extracted twice with 1,1'-oxybisethane. The combined extracts are washed with water, dried, filtered and evaporated. The residue is purified by column-chromatography over silica gel using trichloromethane as eluent. The first fraction is collected and the eluent is evaporated. The residue is converted into the nitrate salt in 4-methyl-2-pentanone and 2,2'-oxybispropane. The salt is filtered off and crystallized from a mixture of acetonitrile and 2,2'-oxybispropane, yielding 3 parts of cis-1-[4-([1,1'-biphenyl]-4-yloxymethyl)-2-(3,4,5-trichlorophenyl)-1,3-dioxolan-2-ylmethyl]-1H-imidazole nitrate; mp. 212.2° C. The second fraction is collected and the eluent is evaporated. The residue is converted into the nitrate salt in 4-methyl-2-pentanone and 2,2'-oxybispropane. The salt is filtered off and crystallized from a mixture of acetonitrile and 2,2'-oxybispropane, yielding 1.9 parts of trans-1-[4-([1,1'-biphenyl]-4-yloxymethyl)-2-(3,4,5-trichlorophenyl)-1,3-dioxolan-2-ylmethyl]-1H-imidazole nitrate; mp. 158° C.

EXAMPLE CXXI

Following the procedure of Example CXX and using equivalent amounts of the appropriate starting materials, the following imidazoles and imidazole acid addition salts are prepared:
cis-1-[4-([1,1'-biphenyl]-4-yloxymethyl)-2-(4-bromo-2-chlorophenyl)-1,3-dioxolan-2-ylmethyl]-1H-imidazole; mp. 161.8° C.;

trans-1-[4-([1,1'-biphenyl]-4-yloxymethyl)-2-(4-bromo-2-chlorophenyl)-1,3-dioxolan-2-ylmethyl]-1H-imidazole; mp. 164.6° C.;

cis-1-[4-([1,1'-biphenyl]-4-yloxymethyl)-2-(2-naphthalenyl)-1,3-dioxolan-2-ylmethyl]-1H-imidazole; mp. 152.6° C.;

trans-1-[4-([1,1'-biphenyl]-4-yloxymethyl)-2-(2-naphthalenyl)-1,3-dioxolan-2-ylmethyl]-1H-imidazole nitrate; mp. 230.6° C.;

cis-1-[4-([1,1'-biphenyl]-4-yloxymethyl)-2-(2,4,5-trichlorophenyl)-1,3-dioxolan-2-ylmethyl]-1H-imidazole nitrate; mp. 199.2° C.; and trans-1-[4-([1,1'-biphenyl]-4-yloxymethyl)-2-(2,4,5-trichlorophenyl)-1,3-dioxolan-2-ylmethyl]-1H-imidazole; mp. 139.2° C.

EXAMPLE CXXII

A mixture of 6.4 parts of 1H-imidazole, 10 parts of A+B-2-(bromomethyl)-4-(3-chloro-[1,1'-biphenyl]-4-yloxymethyl)-2-(2,4-dichlorophenyl)-1,3-dioxolane and 135 parts of N,N-dimethylacetamide is stirred and refluxed for 5 days. The reaction mixture is allowed to cool to room temperature and poured onto water. The product is extracted twice with 1,1'-oxybisethane. The combined extracts are washed with water, dried, filtered and evaporated. The residue is crystallized from 4-methyl-2-pentanone, yielding 2.2 parts (22%) of trans-1-[4-(3-chloro-[1,1'-biphenyl]-4-yloxymethyl)-2-(2,4-dichlorophenyl)-1,3-dioxolan-2-ylmethyl]-1H-imidazole; mp. 140.8° C.

EXAMPLE CXXIII

A mixture of 10.2 parts of 1H-imidazole and 26.8 parts of sodium methoxide solution 30% is stirred and refluxed for 15 minutes. Then there are added 90 parts of N,N-dimethylformamide. The methanol is distilled off till internal temperature of about 130° C. After the addition of another 90 parts of N,N-dimethylformamide, 50 parts of A+B-4-([1,1'-biphenyl]-4-yloxymethyl)-2-(bromomethyl)-2-(2,4-dichlorophenyl)-1,3-dioxolane are added portionwise at about 100° C. Upon completion, stirring is continued for 5 hours at reflux temperature. The reaction mixture is poured onto a mixture of water and methylbenzene. The organic phase is separated and stirred with activated charcoal. The latter is filtered off and the filtrate is evaporated. The residue is purified twice by column-chromatography over silica gel using a mixture of trichloromethane and 1% of methanol as eluent. The pure fractions are collected and the eluent is evaporated. The residue is crystallized from 2-propanol, yielding 9.3 parts of cis-1-[4-([1,1'-biphenyl]-4-yloxymethyl)-2-(2,4-dichlorophenyl)-1,3-dioxolan-2-ylmethyl]-1H-imidazole; mp. 150.7° C.

EXAMPLE CXXIV

To a stirred sodium methoxide solution, prepared starting from 3.8 parts of sodium in 40 parts of methanol, are added 11 parts of 1H-imidazole and 225 parts of N,N-dimethylformamide. The methanol is distilled off till internal temperature of 150° C. Then there are added 19 parts of A+B-2-(bromomethyl)-2-(2,4-dichlorophenyl)-4-ethyl-1,3-dioxolane and the whole is stirred and refluxed for 1 hour. The reaction mixture is allowed to cool to room temperature and poured onto water. The product is extracted three times with 1,1'-oxybisethane. The combined extracts are washed with water, dried, filtered and evaporated. The residue is purified by column-chromatography over silica gel using a mixture of trichloromethane and 1% of methanol as eluent. The first fraction is collected and the eluent is evaporated. The residue is is converted into the nitrate salt in 2,2'-oxybispropane. The salt is filtered off and crystallized from a mixture of 2-propanol and 2,2'-oxybispropane, yielding 12 parts (56%) of A+B-1-[2-(2,4-dichlorophenyl)-4-ethyl-1,3-dioxolan-2-ylmethyl]-1H-imidazole nitrate; mp. 149.1° C.

EXAMPLE CXXV

To a stirred sodium methoxide solution, prepared starting from 2.8 parts of sodium in 40 parts of methanol, are added 8 parts of 1H-imidazole and 225 parts of N,N-dimethylformamide. The methanol is distilled off till internal temperature of 150° C. Then there are added 30 parts of A+B-2-(4-bromo-2-chlorophenyl)-2-(bromomethyl)-4-ethyl-1,3-dioxolane and stirring is continued for 1 hour at reflux temperature. The reaction mixture is cooled and poured onto water. The product is extracted twice with 2,2'-oxybispropane. The combined extracts are washed with water, dried, filtered and evaporated. The residue is purified by column-chromatography over silica gel using a mixture of trichloromethane and 2% of methanol as eluent. The pure fractions are collected and the eluent is evaporated. The residue is converted into the nitrate salt in 2,2'-oxybispropane. The salt is filtered off and crystallized from a mixture of 4-methyl-2-pentanone and 2,2'-oxybispropane, yielding 8.5 parts (26%) of A+B-1-[2-(4-bromo-2-chlorophenyl)-4-ethyl-1,3-dioxolan-2-ylmethyl]-1H-imidazole nitrate; mp. 162.2° C.

EXAMPLE CXXVI

Following the procedure of Example CXXV and using equivalent amounts of the appropriate starting materials, the following imidazole acid addition salts are prepared:

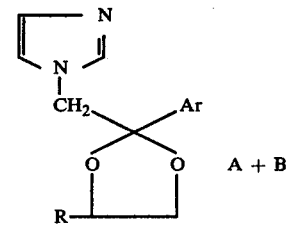

| Ar | R | Acid Salt | Melting Point |
|---|---|---|---|
| 2-Cl—$C_6H_4$ | $C_2H_5$ | $HNO_3$ | 147.6° C. |
| 2-$CH_3$—$C_6H_4$ | $C_2H_5$ | $HNO_3$ | 117.5° C. |
| 4-$CH_3$—$C_6H_4$ | $C_2H_5$ | $HNO_3$ | 172.7° C. |
| 2,3,4-$(Cl)_3$—$C_6H_2$ | $C_2H_5$ | $HNO_3$ | 176.4° C. |
| 2-Br—$C_6H_4$ | $C_2H_5$ | $HNO_3$ | 135.3° C. |
| 2,3-$(Cl)_2$—$C_6H_3$ | $C_2H_5$ | $HNO_3$ | 140.3° C. |
| 3-Cl—$C_6H_4$ | $C_2H_5$ | $HNO_3$ | 151.6° C. |
| 4-$OCH_3$—$C_6H_4$ | $C_2H_5$ | $HNO_3$ | 157.1° C. |
| 2-$CH_3$-4-Cl—$C_6H_3$ | $C_2H_5$ | $HNO_3$ | 126.8° C. |
| 2-Cl-4-$OCH_3$—$C_6H_3$ | $C_2H_5$ | $HNO_3$ | 117.7° C. |
| 3,4,5-$(Cl)_3$—$C_6H_2$ | $C_2H_5$ | $HNO_3$ | 195.8° C. |
| 2-naphthyl | $C_2H_5$ | $HNO_3$ | 195.1° C. |
| 2-$OCH_3$-4-Cl—$C_6H_3$ | $C_2H_5$ | $HNO_3$ | 131.8° C. |
| 2,4,5-$(Cl)_3$—$C_6H_2$ | $C_2H_5$ | $HNO_3$ | 180.1° C. |
| 2,4-$(Cl)_2$—$C_6H_3$ | $nC_3H_7$ | $HNO_3$ | 119.2° C. |
| 2,4-$(Cl)_2$—$C_6H_3$ | $nC_4H_9$ | $HNO_3$ | 113.1° C. |
| 2,4-$(Cl)_2$—$C_6H_3$ | $nC_5H_{11}$ | $HNO_3$ | 128.3° C. |
| 2,4-$(Cl)_2$—$C_6H_3$ | $nC_6H_{14}$ | $HNO_3$ | 99.4° C. |
| 2,4-$(Cl)_2$—$C_6H_3$ | $nC_7H_{15}$ | $2(COOH)_2$ | 131° C. |
| 2,4-$(Cl)_2$—$C_6H_3$ | $nC_8H_{17}$ | $2(COOH)_2$ | 132.8° C. |

EXAMPLE CXXVII

A mixture of 32 parts of 1-(2,4-dichlorophenyl)-2-(1H-imidazol-1-yl)ethanone, 55 parts of 1,2,3-propanetriol, 35 parts of 4-methylbenzenesulfonic acid, 96 parts of butanol and 360 parts of dimethylbenzene is stirred and refluxed for 5 days with water-separator. The reaction mixture is cooled, washed with a potassium carbonate solution and with water, dried, filtered and evaporated. The residue is dissolved in a diluted ethanedioic acid solution. The resulting solution is washed twice with 1,1'-oxybisethane. The aqueous phase is separated and neutralized with potassium carbonate. The product is extracted with trichloromethane. The extract is dried, filtered and evaporated. The residue is purified by column-chromatography over silica gel using a mixture of trichloromethane and 2% of methanol as eluent. The first fraction is collected and the eluent is evaporated. The residue is converted into the nitrate salt in 2,2'-oxybispropane. The salt is filtered off and crystallized from a mixture of 4-methyl-2-pentanone and 2,2'-oxybispropane, yielding 5.5 parts (9.8%) of A+B-1-[4-(butoxymethyl)-2-(2,4-dichlorophenyl)-1,3-dioxolan-2-ylmethyl]-1H-imidazole nitrate; mp. 101.8° C. The second fraction is collected and the eluent is evaporated. The residue is triturated in 1,1'-oxybisethane. The product is filtered off and crystallized from a mixture of 4-methyl-2-pentanone and petroleumether, yielding 9.75 parts of A+B-2-(2,4-dichlorophenyl)-2-(1H-imidazol-1-ylmethyl)-1,3-dioxolane-4-methanol; mp. 128.1° C.

EXAMPLE CXXVIII

A mixture of 7.7 parts of 1H-imidazole, 8 parts of cis-2-(bromomethyl)-2-(2,4-dichlorophenyl)-1,3-dioxolane-4-methanol, 1 part of potassium iodide and 180 parts of N,N-dimethylacetamide is stirred and reflux for 3 days. The reaction mixture is cooled and evaporated. Then there are added 50 parts of water and 300 parts of trichloromethane to the residue. The whole is washed three times with water, dried, filtered and evaporated. The residue is purified by column-chromatography over silica gel using a mixture of trichloromethane and 2% of methanol as eluent. The pure fractions are collected and the eluent is evaporated, yielding 9.2 parts of cis-2-(2,4-dichlorophenyl)-2-(1H-imidazol-1-ylmethyl)-1,3-dioxolane-4-methanol; mp. 140° C.

EXAMPLE CXXIX

Following the procedure of Example CXXVIII and using an equivalent amount of trans-2-(bromomethyl)-2-(2,4-dichlorophenyl)-1,3-dioxolane-4-methanol as a starting material, there is obtained:
trans-2-(2,4-dichlorophenyl)-2-(1H-imidazol-1-ylmethyl)-1,3-dioxolane-4-methanol; mp. 129° C.

EXAMPLE CXXX

To a stirred mixture of 4 parts of cis-2-(2,4-dichlorophenyl)-2-(1H-imidazol-1-ylmethyl)-1,3-dioxolane-4-methanol, 2.2 parts of iodomethane and 90 parts of N,N-dimethylformamide are added 0.5 parts of sodium hydride dispersion 78%. Stirring is continued for 2 hours at room temperature. The reaction mixture is poured onto water and the product is extracted three times with 1,1'-oxybisethane. The combined extracts are washed with water and acidified with a nitric acid solution in 1,1'-oxybisethane. The formed nitrate salt is filtered off and crystallized from 4-methyl-2-pentanone, yielding 2.2 parts (45%) of cis-1-[2-(2,4-dichlorophenyl)-4-(methoxymethyl)-1,3-dioxolane-2-ylmethyl]-1H-imidazole nitrate; mp. 140° C.

EXAMPLE CXXXI

To a stirred mixture of 4 parts of cis-2-(2,4-dichlorophenyl)-2-(1H-imidazol-1-ylmethyl)-1,3-dioxolane-4-methanol, 1.7 parts of bromoethane and 90 parts of N,N-dimethylformamide are added 0.5 parts of sodium hydride dispersion 78%. The whole is stirred for 1 hour at room temperature. The reaction mixture is poured onto water and the product is extracted three times with 2,2'-oxybispropane. The combined extracts are washed with water and acidified with a nitric acid solution in 2,2'-oxybispropane. The formed nitrate salt is filtered off and crystallized from a mixture of 4-methyl-2-pentanone and 2,2'-oxybispropane, yielding 4.7 parts (93%) of cis-1-[2-(2,4-dichlorophenyl)-4-(ethoxymethyl)-1,3-dioxolan-2-ylmethyl]-1H-imidazole nitrate; mp. 134.7° C.

EXAMPLE CXXXII

Following the procedure of Example CXXXI and using an equivalent amount of appropriate bromoalkane or bromoalkene in place of the bromoethane used therein, the following imidazole acid addition salts are prepared:
cis-1-[2-(2,4-dichlorophenyl)-4-(propoxymethyl)-1,3-dioxolan-2-ylmethyl)-1H-imidazole nitrate; mp. 131.7° C.;
cis-1-[2-(2,4-dichlorophenyl)-4-(pentyloxymethyl)-1,3-dioxolan-2-ylmethyl]-1H-imidazole nitrate; mp. 78.6° C.;
cis-1-[2-(2,4-dichlorophenyl)-4-(hexyloxymethyl)-1,3-dioxolan-2-ylmethyl]-1H-imidazole nitrate; mp. 87.1° C.;
cis-1-[2-(2,4-dichlorophenyl)-4-(heptyloxymethyl)-1,3-dioxolan-2-ylmethyl]-1H-imidazole nitrate; mp. 80.7° C.;
cis-1-[2-(2,4-dichlorophenyl)-4-(octyloxymethyl)-1,3-dioxolan-2-ylmethyl]-1H-imidazole nitrate; mp. 73.4° C.; and
cis-1-[2-(2,4-dichlorophenyl)-4-(2-propenyloxymethyl)-1,3-dioxolan-2-ylmethyl]-1H-imidazole nitrate; mp. 116.3° C.

EXAMPLE CXXXIII

To a mixture of 4 parts of trans-2-(2,4-dichlorophenyl)-2-(1H-imidazol-1-ylmethyl)-1,3-dioxolane-4-methanol, 1.7 parts of bromoethane and 90 parts of N,N-dimethylformamide are added 0.5 parts of sodium hydride dispersion 78% and the whole is stirred for 2 hours at room temperature. The reaction mixture is poured onto water and the product is extracted twice with 2,2'-oxybispropane. The combined extracts are washed with water and taken up in 2,2'-oxybispropane. The solution is acidified with nitric acid. The formed nitrate salt is filtered off and crystallized from 4-methyl-2-pentanone, yielding 3.5 parts (69%) of trans-1-[2-(2,4-dichlorophenyl)-4-(ethoxymethyl)-1,3-dioxolan-2-ylmethyl]-1H-imidazole nitrate; mp. 151.4° C.

EXAMPLE CXXXIV

To a stirred mixture of 2.5 parts of 1-chloro-4-(chloromethyl)-benzene, 4 parts of cis-2-(2,4-dichlorophenyl)-2-(1H-imidazol-1-ylmethyl)-1,3-dioxolane-4-methanol and 90 parts of N,N-dimethylformamide are added 0.5 parts of sodium hydride dispersion 78%. Stirring is continued for 5 hours at room temperature. The reaction mixture is poured onto water and the product is extracted twice with 2,2'-oxybispropane. The combined extracts are washed with water, dried, filtered and acidified with nitric acid. The formed nitrate salt is filtered off and crystallized from a mixture of 4-methyl-2-pentanone and 2,2'-oxybispropane. The product is filtered off and recrystallized from a mixture of 4-methyl-2-pentanone and 2,2'-oxybispropane, yielding 3.5 parts (56%) of cis-1-[4-(4-chlorophenylmethoxymethyl)-2-(2,4-dichlorophenyl)-1,3-dioxolan-2-ylmethyl]-1H-imidazole nitrate; mp. 131.7° C.

EXAMPLE CXXXV

By repeating the procedure of Example CXXXIV and using an equivalent amount of an appropriate (chloromethyl)benzene in place of the 1-chloro-4-(chloromethyl)benzene used therein, there are obtained:

cis-1-{4-[(4-bromophenyl)methoxymethyl]-2-(2,4-dichlorophenyl)-1,3-dioxolan-2-ylmethyl}-1H-imidazole nitrate; mp. 101.4° C.; and cis-1-{2-(2,4-dichlorophenyl)-4-[(4-fluorophenyl)methoxymethyl]-1,3-dioxolan-2-ylmethyl}-1H-imidazole nitrate; mp. 107° C.

EXAMPLE CXXXVI

To a stirred mixture of 3.3 parts of 2,4-dichloro-1-(chloromethyl)benzene, 5 parts of A+B-2-(2,4-dichlorophenyl)-2-(1H-imidazol-1-ylmethyl)-1,3-dioxolane-4-methanol and 90 parts of N,N-dimethylformamide are added 0.5 parts of sodium hydride dispersion 78% and stirring is continued for 3 hours at room temperature. The reaction mixture is poured onto water and the product is extracted three times with 2,2'-oxybispropane. The combined extracts are washed with water, dried, filtered and evaporated. The residue is purified by column-chromatography over silica gel using trichloromethane as eluent. The first fraction (A-isomer) is collected and the eluent is evaporated. The residue is converted into the nitrate salt in 4-methyl-2-pentanone and 2,2'-oxybispropane. The salt is filtered off and recrystallized from a mixture of 4-methyl-2-pentanone and 2,2'-oxybispropane at 0° C., yielding 2.9 parts (35%) of cis-1-{2-(2,4-dichlorophenyl)-4-[(2,4-dichlorophenyl)methoxymethyl]-1,3-dioxolan-2-ylmethyl}-1H-imidazole nitrate; mp. 96.9° C. The second fraction (B-isomer) is collected and the eluent is evaporated. The residue is converted into the nitrate salt in 4-methyl-2-pentanone and 1,1'-oxybisethane. The salt is filtered off and recrystallized from a mixture of 4-methyl-2-pentanone and 2,2'-oxybispropane, yielding 1.6 parts (19%) of trans-1-{2-(2,4-dichlorophenyl)-4-](2,4-dichlorophenyl)methoxymethyl]-1,3-dioxolan-2-ylmethyl}-1H-imidazole nitrate; mp. 131.9° C.

EXAMPLE CXXXVII

By repeating the procedure of Example CXXXVI and using an equivalent amount of 4-(chloromethyl)-1,1'-bisphenyl in place of the 2,4-dichloro-1-chloromethylbenzene used therin, there are obtained:

cis-1-[4-([1,1'-biphenyl]-4-ylmethoxymethyl)-2-(2,4-dichlorophenyl)-1,3-dioxolan-2-ylmethyl]-1H-imidazole diethanedioate; mp. 107.6° C.; and trans-1-[4-([1,1'-biphenyl]-4-ylmethoxymethyl)-2-(2,4-dichlorophenyl)-1,3-dioxolan-2-ylmethyl]-1H-imidazole nitrate; mp. 168° C.

EXAMPLE CXXXVIII

A mixture of 2.2 parts of (4-hydroxyphenyl) phenyl methanone, 4.2 parts of cis-2-(2,4-dichlorophenyl)-2-(1H-imidazol-1-ylmethyl)-1,3-dioxolan-4-ylmethyl methanesulfonate, 2 parts of potassium carbonate and 68 parts of N,N-dimethylformamide is stirred overnight at 100° C. The reaction mixture is cooled and poured onto water. The product is extracted twice with 1,1'-oxybisethane. The combined extracts are washed with water, dried, filtered and evaporated. The residue is converted into the nitrate salt in 4-methyl-2-pentanone and 2,2'-oxybispropane, yielding 4.5 parts (78%) of cis-{4-[2-(2,4-dichlorophenyl)-2-(1H-imidazol-1-ylmethyl)-1,3-dioxolan-4-ylmethoxy]phenyl} phenyl methanone nitrate; mp. 179° C.

EXAMPLE CXXXIX

Following the procedure of Example CXXXVIII and using an equivalent amount of an appropriate phenol in place of the (4-hydroxymethyl) phenyl methanone used therein, the following imidazoles and imidazole acid addition salts are prepared:

cis-5-chloro-2-[2-(2,4-dichlorophenyl)-2-(1H-imidazol-1-ylmethyl)-1,3-dioxolan-4-ylmethoxy]-4-methylphenyl phenyl methanone ethanedioate; mp. 170.8° C.;

cis-methyl 4-[2-(2,4-dichlorophenyl)-2-(1H-imidazol-1-ylmethyl)-1,3-dioxolan-4-ylmethoxy]benzoate nitrate; mp. 167.8° C.;

cis-{2-[2-(2,4-dichlorophenyl)-2-(1H-imidazol-1-ylmethyl)-1,3-dioxolan-4-ylmethoxy]-5-methylphenyl}•phenyl methanone nitrate; mp. 145.4° C.;

cis-(4-chlorophenyl){2-[2-(2,4-dichlorophenyl)-2-(1H-imidazol-1-ylmethyl)-1,3-dioxolan-4-ylmethoxy]-4-methoxyphenyl}methanone; mp. 168.3° C.;

cis-{2-[2-(2,4-dichlorophenyl)-2-(1H-imidazol-1-ylmethyl)-1,3-dioxolan-4ylmethoxy]-4-methoxyphenyl}•phenyl methanone; mp. 149.2° C.;

cis-1-{2-(2,4-dichlorophenyl)-4-[3-(trifluoromethyl)-phenoxymethyl]-1,3-dioxolan-2-ylmethyl}-1H-imidazole nitrate; mp. 152.6° C.;

cis-1-{4-[2-(2,4-dichlorophenyl)-2-(1H-imidazol-1-ylmethyl)-1,3-dioxolan-4-ylmethoxy]phenyl}ethanone nitrate; mp. 182.6° C.;

cis-methyl 2-[2-(2,4-dichlorophenyl)-2-(1H-imidazol-1-ylmethyl)-1,3-dioxolan-4-ylmethoxy]benzoate nitrate; mp. 140.5° C.; and cis-1-{4-[2-(2,4-dichlorophenyl)-2-(1H-imidazol-1-ylmethyl)-1,3-dioxolan-4-ylmethoxy]phenyl}-1-propanone nitrate; mp. 176.2° C.

EXAMPLE CXL

A mixture of 12.5 parts of 1,2-butanediol, 19 parts of 1-(2-chloro-4-fluorophenyl)-2-(1H-imidazol-1yl)ethanone hydrochloride, 16 parts of 4-methylbenzenesulfonic acid, 40 parts of 1-butanol and 225 parts of dimethylbenzene is stirred and refluxed for 6 days with water-separator. After cooling, the reaction mixture is filtered and the filtrate is washed with a diluted sodium hydroxide solution and with water. After the addition of 2,2'-oxybispropane, the whole is acidified with a nitric acid solution. The formed nitrate salt is filtered off and crystallized from a mixture of 4-methyl-2-pentanone and 2,2'-oxybispropane, yielding 5.7 parts (22%) of A+B-1-[2-(2-chloro-4-fluorophenyl)-4-ethyl-1,3-dioxolan-2-ylmethyl]-1H-imidazole nitrate; mp. 132.4° C.

EXAMPLE CXLI

Following the procedure of Example CXL and using equivalent amounts of the appropriate starting materials, the following imidazoles and imidazole acid addition salts are prepared:

A+B-1-[2-(4-bromophenyl)-4-ethyl-1,3-dioxolan-2-ylmethyl]-1H-imidazole nitrate; mp. 194.7° C.;

A+B-1-[2-(2,4-dibromophenyl)-4-ethyl-1,3-dioxolan-2-ylmethyl]-1H-imidazole nitrate; mp. 149.7° C.;

A+B-1-[4-ethyl-2-(2-thienyl)-1,3-dioxolan-2-ylmethyl]-1H-imidazole nitrate; mp. 135.4° C.;

A+B-1-[2-(5-chloro-2-thienyl)-4-ethyl-1,3-dioxolan-2-ylmethyl]-1H-imidazole nitrate; mp. 164.3° C.;

A+B-1-[4-(chloromethyl)-2-(2,4-dichlorophenyl)-1,3-dioxolan-2-ylmethyl]-1H-imidazole nitrate; mp. 166.1° C.;

A+B-1-[4-([1,1'-biphenyl]-4-ylmethyl)-2-(2,4-dichlorophenyl)-1,3-dioxolan-2-ylmethyl]-1Himidazole diethanedioate; mp. 116.8° C.;

A+B-1-[2-(2-(2,4-dichlorophenyl)-4-(4-fluorophenylmethyl)-1,3-dioxolan-2-ylmethyl]-1H-imidazole sesquiethanedioate; mp. 153.1° C.;

A+B-1-{2-(2,4-dichlorophenyl)-4-[(4-methylphenyl)methyl]-1,3-dioxolan-2-ylmethyl}-1H-imidazole sesquiethanedioate; mp. 123.1° C.

A+B-1-[4-(4-bromophenylmethyl)-2-(2,4-dichlorophenyl)-1,3-dioxolan-2-ylmethyl]-1H-imidazole diethanedioate; mp. 128.8° C.;

A+B-1-{4-[2-([1,1'-biphenyl]-4-yl)ethyl]-2-(2,4-dichlorophenyl)-1,3-dioxolan-2-ylmethyl}-1H-imidazole sequiethanedioate hemihydrate; mp. 143.9° C.; and A+B-1-{2-(2,4-dichlorophenyl)-4-[2-(phenylmethyl)phenoxymethyl]-1,3-dioxolan-2-ylmethyl}-1H-imidazole sesquiethanedioate. hemihydrate; mp. 113° C.

EXAMPLE CXLII

A mixture of 13.8 parts of 1-(2-chloro-4-fluorophenyl)-2-(1H-imidazol-1-yl)ethanone hydrochloride, 14.6 parts of 3-([1,1'-biphenyl]-4-yloxy)-1,2-propanediol, 16 parts of 4-methylbenzenesulfonic acid, 40 parts of butanol and 225 parts of dimethylbenzene is stirred and refluxed for one week with water-separator. After cooling, 1,1'-oxybisethane is added and the whole is washed successively with a diluted sodium hydroxide solution and with water, dried, filtered and evaporated. The residue is purified by column-chromatography over silica gel using trichloromethane as eluent. The first fraction (A-isomer) is collected and the eluent is evaporated. The residue is converted into the nitrate salt is 4-methyl-2-pentanone and 2,2'-oxybispropane. The product is filtered off and crystallized from a mixture of acetonitrile and 2,2'-oxybispropane, yielding 5 parts of cis-1-[4-([1,1'-bisphenyl]-4-yloxymethyl)-2-(2-chloro-4-fluorophenyl)-1,3-dioxolan-2-ylmethyl]-1H-imidazole nitrate; mp. 185.7° C. The second fraction (B-isomer) is collected and the eluent is evaporated. The residue is converted into the nitrate salt in 4-methyl-2-pentanone and 2,2'-oxybispropane. The salt is filtered off and crystallized from a mixture of acetonitrile and 2,2'-oxybispropane, yielding 5.9 parts of trans-1-[4-([1,1'-biphenyl]-4-yloxymethyl)-2-(2-chloro-4-fluorophenyl)-1,3-dioxolan-2-ylmethyl]-1H-imidazole nitrate; mp. 156.9° C.

EXAMPLE CXLIII

Following the procedure of Example CXLII and using equivalent amounts of the appropriate starting materials, the following imidazoles and imidazole acid addition salts are prepared. When only one isomer is listed, no second fraction was obtained from chromatography.

cis-1-[4-([1,1'-biphenyl]-4-yloxymethyl)-2-(2-thienyl)-1,3-dioxolan-2-ylmethyl]-1H-imidazole; mp. 149.5° C.;

trans-1-[4-([1,1'-biphenyl]-4-yloxymethyl)-2-(2-thienyl)-1,3-dioxolan-2-ylmethyl]-1H-imidazole; mp.>300° C.;

cis-1-([1,1'-biphenyl]-4-yloxymethyl)-2-(2,4-dibromophenyl)-1,3-dioxolan-2-ylmethyl]-1H-imidazole nitrate; mp. 174.4° C.;

trans-1-[4-([1,1'-biphenyl]-4-yloxymethyl)-2-(2,4-dibromophenyl)-1,3-dioxolan-2-ylmethyl]-1H-imidazole nitrate; mp. 141.8° C.; and cis-1-[4-([1,1'-biphenyl]-4-yloxymethyl)-2-(5-chloro-2-thienyl)-1,3-dioxolan-2-ylmethyl]-1H-imidazole nitrate; mp. 170° C.

EXAMPLE CXLIV

To a stirred mixture of 1.1 parts of 3-chloro-1-propyne, 4 parts of cis-2-(2,4-dichlorophenyl)-2-(1H-imidazol-1-ylmethyl)-1,3-dioxolane-4-methanol and 90 parts of N,N-dimethylformamide are added 0.5 parts of sodium hydride dispersion 78%. Stirring is continued for 3 hours at room temperature. The reaction mixture is poured onto water and the product is extracted twice with 1,1'-oxybisethane. The combined extracts are washed with water, dried, filtered and evaporated. The residue is purified by column-chromatography over silica gel using a mixture of trichloromethane and methanol (98:2) as eluent. The pure fractions are collected and the eluent is evaporated. The residue is converted into the ethanedioate salt in 4-methyl-2-pentanone and 2,2'-oxybispropane. The salt is filtered off and crystallized from 4-methyl-2-pentanone, yielding 3.6 parts (55%) of cis-1-[2-(2,4-dichlorophenyl)-4-(2-propynyloxymethyl)-1,3-dioxolan-2-ylmethyl]-1H-imidazole diethanedioate; mp. 145.6° C.

EXAMPLE CXLV

A mixture of 17 parts of 1H-imidazole, 16 parts of A+B-2-(bromomethyl)-2-(2,4-dichlorophenyl)-4-ethenyl-1,3-dioxolane and 225 parts of N,N-dimethylformamide is stirred and refluxed for 3 days. The reaction mixture is cooled, poured onto water and the product is extracted twice with 1,1'-oxybisethane. The combined extracts are washed with water, dried, filtered and evaporated. The residue is purified by column-chromatography over silica gel using trichloromethane as eluent. The pure fractions are collected and the eluent is evaporated. The residue is converted into the nitrate salt in 4-methyl-2-pentanone and 2,2'-oxybispropane. The salt is filtered off and crystallized from 4-methyl-2-pentanone, yielding 2.4 parts (13%) of A+B-1-[2-(2,4-dichlorophenyl)-4-ethenyl-1,3-dioxolan-2-ylmethyl]-1H-imidazole nitrate; mp. 150.9° C.

I claim:

1. A chemical compound having the formula:

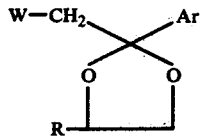

wherein:
W is halo;
Ar is a member selected from the group consisting of phenyl and substituted phenyl, wherein said substituted phenyl is phenyl having from 1 to 3 substituents independently selected from the group consisting of halo, loweralkyl, loweralkyloxy, nitro and cyano; and
R is alkenyl, wherein said alkenyl has from 2 to 10 carbon atoms.

2. The compound of claim 1 wherein said W is bromo, said Ar is 2,4-dichlorophenyl and said R is ethenyl.

* * * * *